United States Patent
Chen et al.

(10) Patent No.: US 11,753,476 B2
(45) Date of Patent: *Sep. 12, 2023

(54) COMBINATION THERAPY FOR CANCERS WITH BRAF MUTATION

(71) Applicant: COTHERA BIOSCIENCES, INC., Grand Cayman (KY)

(72) Inventors: Yiyou Chen, Beijing (CN); Chun Jiang, Hillsborough, CA (US)

(73) Assignee: Cothera BioScience, Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/045,982

(22) PCT Filed: Apr. 8, 2019

(86) PCT No.: PCT/CN2019/081674
§ 371 (c)(1),
(2) Date: Oct. 7, 2020

(87) PCT Pub. No.: WO2019/196764
PCT Pub. Date: Oct. 17, 2019

(65) Prior Publication Data
US 2021/0179718 A1 Jun. 17, 2021

(30) Foreign Application Priority Data
Apr. 8, 2018 (WO) ............... PCT/CN2018/082191

(51) Int. Cl.
| C07K 16/28 | (2006.01) |
| A61K 31/4523 | (2006.01) |
| A61K 31/519 | (2006.01) |
| A61K 39/00 | (2006.01) |
| A61K 31/506 | (2006.01) |
| A61K 45/06 | (2006.01) |

(52) U.S. Cl.
CPC ...... C07K 16/2863 (2013.01); A61K 31/4523 (2013.01); A61K 31/506 (2013.01); A61K 31/519 (2013.01); A61K 45/06 (2013.01); A61K 2039/505 (2013.01); C07K 2317/24 (2013.01); C07K 2317/76 (2013.01)

(58) Field of Classification Search
CPC .............. A61K 31/4523; A61K 31/506; A61K 31/519; A61K 39/3955; A61K 39/39558; A61K 2039/505; A61K 2039/545; A61K 2039/55; A61K 2039/585; A61P 35/00; C07K 16/2863; C07K 2317/24; C07K 2317/76
See application file for complete search history.

(56) References Cited

U.S. PATENT DOCUMENTS

| 5,844,093 A | 12/1998 | Kettleborough et al. |
| 6,734,203 B2 | 5/2004 | Matsuhisa et al. |
| 7,132,511 B2 | 11/2006 | Carr et al. |
| 7,247,301 B2 | 7/2007 | van de Winkel et al. |
| 7,595,378 B2 | 9/2009 | van de Winkel et al. |
| 7,618,992 B2 | 11/2009 | Nakahara et al. |
| 7,723,484 B2 | 5/2010 | Beidler et al. |
| 7,939,072 B2 | 5/2011 | Yarden et al. |
| 7,960,516 B2 | 6/2011 | Matheus et al. |
| 8,003,105 B2 | 8/2011 | Nakahara et al. |
| 9,662,329 B2 | 5/2017 | Chang et al. |
| 9,737,535 B2 | 8/2017 | Fultz et al. |
| 10,004,735 B2 | 6/2018 | Fultz et al. |
| 2003/0114508 A1 | 6/2003 | Matsuhisa et al. |
| 2005/0222163 A1 | 10/2005 | Eck et al. |
| 2006/0223831 A1 | 10/2006 | Kinoyama et al. |
| 2006/0257895 A1 | 11/2006 | Pinkel et al. |
| 2008/0166344 A1 | 7/2008 | Nakahara et al. |
| 2009/0124595 A1 | 5/2009 | Adams et al. |
| 2009/0246198 A1 | 10/2009 | Dong et al. |
| 2009/0263390 A1 | 10/2009 | Nakahara et al. |
| 2010/0004234 A1 | 1/2010 | Santi et al. |
| 2010/0249413 A1 | 9/2010 | Murai et al. |
| 2012/0028907 A1 | 2/2012 | Shackney |
| 2012/0122910 A1 | 5/2012 | Berezov et al. |
| 2013/0035336 A1 | 2/2013 | Borland et al. |
| 2014/0199236 A1 | 7/2014 | Chen et al. |
| 2014/0271634 A1 | 9/2014 | Sliwkowski et al. |
| 2014/0314749 A1 | 10/2014 | French et al. |

(Continued)

FOREIGN PATENT DOCUMENTS

| CA | 2943402 A1 | 10/2015 |
| CN | 101910167 A | 12/2010 |

(Continued)

OTHER PUBLICATIONS

Morikawa et. al., Oncology Lett., vol. 15, pp. 2195-2201, publ. online Dec. 8, 2017 (Year: 2017).*
Barras, (2015). "BRAF Mutation in Colorectal Cancer: An Update: Supplementary Issue: Biomarkers for Colon Cancer," Biomarkers in Cancer, 7:9-12.
Berge et al., (1977). "Pharmaceutical Salts," J. Pharm. Sci. 66(1):1-19.
Cantwell-Dorris et al., (2011). "BRAFV600E: Implications for Carcinogenesis and Molecular Therapy," Mol. Cancer Ther., 10:385-394.
Chapman et al., (2011). "Improved survival with vemurafenib in melanoma with BRAF V600E mutation," N. Engl. J. Med., 364:2507-16.

(Continued)

*Primary Examiner* — Sarah Pihonak
(74) *Attorney, Agent, or Firm* — MORRISON & FOERSTER LLP

(57) ABSTRACT

The present disclosure provides a combination therapy for treating cancer with BRAF mutations comprising administrating to a subject an effective amount of (a) an epidermal growth factor receptor (EGFR) inhibitor; (b) a mitogen-activated protein kinase (MEK) 1/2 inhibitor; and (c) a cyclin dependent kinase (CDK) 4/6 inhibitor. Also provided are compositions and kits related to the combination therapy.

23 Claims, 9 Drawing Sheets

(56) References Cited

U.S. PATENT DOCUMENTS

| | | | |
|---|---|---|---|
| 2016/0024591 | A1 | 1/2016 | Xu et al. |
| 2016/0095942 | A1 | 4/2016 | Markovic et al. |
| 2016/0228457 | A1 | 8/2016 | Chigaev et al. |
| 2016/0317538 | A1 | 11/2016 | Saha et al. |
| 2016/0367663 | A1 | 12/2016 | Doshi et al. |
| 2017/0027951 | A1* | 2/2017 | Klampfer ........... A61K 31/5025 |
| 2017/0080093 | A1 | 3/2017 | Hoffman |
| 2017/0114098 | A1 | 4/2017 | Aivado et al. |
| 2019/0046529 | A1 | 2/2019 | Quayle et al. |
| 2019/0292602 | A1 | 9/2019 | Chapuy et al. |
| 2020/0147211 | A1 | 5/2020 | Zhang et al. |
| 2021/0179718 | A1 | 6/2021 | Chen |
| 2021/0180141 | A1 | 6/2021 | Li et al. |

FOREIGN PATENT DOCUMENTS

| | | |
|---|---|---|
| CN | 106822905 A | 6/2017 |
| CN | 107708734 A | 2/2018 |
| EP | 1747784 A1 | 1/2007 |
| EP | 2127652 A1 | 12/2009 |
| JP | 2017502013 A | 1/2017 |
| JP | 2017511341 A | 4/2017 |
| KR | 20140131827 A | 11/2014 |
| WO | WO-2001060803 A1 | 8/2001 |
| WO | WO-2004092160 A1 | 10/2004 |
| WO | WO-2005052005 A1 | 6/2005 |
| WO | WO-2007086342 A1 | 8/2007 |
| WO | WO-2007140222 A2 | 12/2007 |
| WO | WO-2008054701 A1 | 5/2008 |
| WO | WO-2008023807 A1 | 1/2010 |
| WO | WO-2010020675 A1 | 2/2010 |
| WO | WO-2008081927 A1 | 4/2010 |
| WO | WO-2011106298 A1 | 9/2011 |
| WO | WO-2012022724 A1 | 2/2012 |
| WO | WO-2012095505 A1 | 7/2012 |
| WO | WO-2012161177 A1 | 11/2012 |
| WO | WO-2012167099 A1 | 12/2012 |
| WO | WO-2013034806 A1 | 3/2013 |
| WO | WO-2013060872 A1 | 5/2013 |
| WO | WO-2013074596 A1 | 5/2013 |
| WO | WO-2013148649 A1 | 10/2013 |
| WO | WO-2014018725 A1 | 1/2014 |
| WO | WO-2014147573 A3 | 12/2014 |
| WO | WO-2015095840 A1 | 6/2015 |
| WO | WO-2015150826 A1 | 10/2015 |
| WO | WO-2015193212 A1 | 12/2015 |
| WO | WO-2016191296 A1 | 12/2016 |
| WO | WO-2016201370 A1 | 12/2016 |
| WO | WO-2017019279 A1 | 2/2017 |
| WO | WO-2017037576 A1 | 3/2017 |
| WO | WO-2017048800 A1 | 3/2017 |
| WO | WO-2017070475 A1 | 4/2017 |
| WO | WO-2017120439 A1 | 7/2017 |
| WO | WO-2018054348 A1 | 3/2018 |
| WO | WO-2018127786 A1 | 7/2018 |
| WO | WO-2018218633 A1 | 12/2018 |
| WO | WO-2018223022 A1 | 12/2018 |
| WO | WO-2019195959 A1 | 10/2019 |
| WO | WO-2020034061 A1 | 2/2020 |
| WO | WO-2020036852 A1 | 2/2020 |
| WO | WO-2020097901 A1 | 5/2020 |

OTHER PUBLICATIONS

Cheng et al., (2017). "Current Development Status of MEK Inhibitors," Molecules, 22:1551.
Davies et al., (2002). "Mutations of the BRAF gene in human cancer," Nature, 417:949-54.
Hall et al., (2014). "BRAF mutations: signaling, epidemiology, and clinical experience in multiple malignancies," Cancer Control, 21:221-30.
Hyman et al., (2015). "Vemurafenib in Multiple Nonmelanoma Cancers with BRAF V600 Mutations," N. Engl. J. Med., 373:726-736.
International Search Report and Written Opinion dated Jan. 11, 2021, for PCT Patent Application No. PCT/CN2020/119873, 13 pages.
International Search Report and Written Opinion dated Jan. 8, 2019, for PCT Patent Application No. PCT/CN2018/082191, 11 pages.
International Search Report and Written Opinion dated Jan. 8, 2021, for PCT Patent Application No. PCT/CN2020/119874, 18 pages.
International Search Report and Written Opinion dated Sep. 5, 2019, for PCT Patent Application No. PCT/CN2019/081674, 9 pages.
Larkin et al., (2014). "Combined Vemurafenib and Cobimetinib in BRAF-Mutated Melanoma," N. Engl. J. Med., 371:1867-1876.
Lasota et al., (2015). "Detection of the BRAF V600E mutation in colon carcinoma: critical evaluation of the imunohistochemical approach," Am J Surg Pathol., 38(9):1235-41, 16 pages.
Lee et al., (2016). "Efficacy of the combination of MEK and CDK4/6 inhibitors in vitro and in vivo in KRAS mutant colorectal cancer models," Oncotarget, 26(7):39595-39608.
Loupakis et al., (2014). "Initial Therapy with FOLFOXIRI and Bevacizumab for Metastatic Colorectal Cancer," N Engl J Med., 371:1609-1618.
Luke et al., (2014). "The Biology and Clinical Development of MEK Inhibitors for Cancer," Drugs, 74(18):2111-2128.
Manzano et al., (2016). "Resistant mechanisms to BRAF inhibitors in melanoma," Ann. Transl Med, 4:237, 9 pages.
Martini et al., (2017). "Present and future of metastatic colorectal cancer treatment: A review of new candidate targets," World Journal of Gastroenterology, 23(26):4675-4688.
Morris et al., (2013). "BRAF inhibitors in clinical oncology," F1000Prime Rep., 5:11, 6 pages.
Oikonornou et al., (2014). "BRAF vs RAS oncogenes: Are mutations of the same pathway equal? Differential signaling and therapeutic implications," Oncotarget, 5:11752-11777.
Pek et al., (2017). "Oncogenic KRAS-associated gene signature defines co-targeting of CDK4/6 and MEK as a viable therapeutic strategy in colorectal cancer," Oncogene, 36:4975-4986.
Robert et al., (2011). "RAF inhibition and induction of cutaneous squamous cell carcinoma," Curr. Opin. Oncol., 23:177-182.
Robert et al., (2015). "Improved Overall Survival in Melanoma with Combined Dabrafenib and Trametinib," N. Engl. J. Med., 372:30-39.
Roskoski, (2014). "The ErbB/HER family of protein-tyrosine kinases and cancer," Pharmacological Research, 79:34-74.
Roskoski, (2019). "Small molecule inhibitors targeting the EGFR/ErbB family of proteintyrosine kinases in human cancers," Pharmacological Research, 139:395-411.
Thomas et al., (2015). "Refining the treatment of NSCLC according to histological and molecular subtypes," Nature Reviews Clinical Oncology, 12(9):511-526.
Wang et al., (2020). "Conditionally reprogrammed colorectal cancer cells combined with mouse avatars identify synergy between EGFR and MEK or CDK4/6 inhibitors," American Journal of Cancer Research, 1(10):249-262.
Xing et al., (2005). "BRAF mutation in thyroid cancer," Endocr. Relat. Cancer, 12:245-62.
Xu et al., (2016). "Advances in small molecule kinase inhibitors for cancer treatment," Chinese Bulletin of Life Sciences, 28(7):786-792, 15 pages (English translation pp. 1-8, Original pp. 9-15).
Zhou et al., (2017). "CDK4/6 or MAPK blockade enhances efficacy of EGFR inhibition in oesophageal squamous cell carcinoma," Nature Communications, 8:31.
Ziemke et al., (2015). "Sensitivity of KRAS-Mutant Colorectal Cancers to Combination Therapy That Cotargets MEK and CDK4/6," Clinical Cancer Research, 2(22):405-414.
Extended European Search Report and Written Opinion dated Jan. 22, 2021, for European Patent Application No. 18810472.3, 6 pages.
International Search Report and Written Opinion dated Aug. 31, 2018, for PCT Patent Application No. PCT/US2018/035641, 9 pages.
International Search Report and Written Opinion dated Mar. 9, 2018, for PCT Patent Application No. PCT/CN2017/086911, 12 pages.

(56) References Cited

OTHER PUBLICATIONS

Adderley et al., (2019). "KRAS-mutant non-small cell lung cancer: Converging small molecules and immune checkpoint inhibition," EBioMedicine, 41:711-716.
Cox et al., (2014). "Drugging the undruggable RAS: Mission possible?," Nat Rev Drug Discov., 13(11):828-851.
Extended European Search Report and Written Opinion dated Jan. 28, 2022, for European Patent Application No. 19784395.6, 8 pages.
Ferrer et al., (2018). "KRAS-Mutant non-small cell lung cancer: From biology to therapy," Lung Cancer, 124:53-64.
Jia et al., (2017). "Characterization of distinct types of KRAS mutation and its impact on first-line platinum-based chemotherapy in Chinese patients with advanced non-small cell lung cancer," Oncol. Lett., 14:6525-6532.
Misale et al., (2014). "Blockade of EGFR and MEK intercepts heterogeneous mechanisms of acquired resistance to anti-EGFR therapies in colorectal cancer," Science Translational Medicine, 6(224):224ra26-1.
Molina et al., (2008). "Non-small cell lung cancer: epidemiology, risk factors, treatment, and survivorship," Mayo Clin Proc., 83(5):584-594, 19 pages.
Mullard, (2019). "Cracking KRAS," Nature Reviews Drug Discovery, 18:887-891.
Porru et al., (2018). "Targeting KRAS in metastatic colorectal cancer: current strategies and emerging opportunities," J Exp Clin Cancer Res., 37(1):57, 10 pages.
Riely et al., (2009). "KRAS mutations in non-small cell lung cancer," Proc Am Thorac Soc, 6:201-205.
Roman et al., (2018). "KRAS oncogene in non-small cell lung cancer: clinical perspectives on the treatment of an old target," Mol Cancer, 17:33, 14 pages.
Troiani et al., (2014). "Primary and acquired resistance of colorectal cancer cells to anti-EGFR antibodies converge on MEK/ERK pathway activation and can be overcome by combined MEK/EGFR inhibition," Clinical Cancer Research, 20(14):3775-3786.
Wu et al., (2020). "Effects of avitinib on the pharmacokinetics of osimertinib in vitro and in vivo in rats," Thoracic Cancer, 11(10):2775-2781.
Maiello et al., (2015). "EGFR and MEK Blockade in Triple Negative Breast Cancer Cells," Journal of Cellular Biochemistry, 116(12):2778-2785.
Masuishi et al., (2016). "Current Progress and Feasibility of Using Molecular-Targeted Agent Combinations for Metastatic Colorectal Cancer," Gan To Kagaku Ryoho, 43(4):408-412. Abstract Only.
Aburjania et al., (2018). "The Role of Notch3 in Cancer," The Oncologist, 23:900-911.
Aoyama et al., (2012). "Pharmacokinetics of sepantronium bromide (YM155), a small-molecule suppressor of survivin, in Japanese patients with advanced solid tumors: dose proportionality and influence of renal impairment," Cancer Chemother Pharmacol, 70:373-380.
Asahi et al., (2016). "YM155 suppresses proliferation and survival of multiple myeloma cells via proteasomal degradation of c-Myc.," J Mec Oncl Ther, 1(2):62-71.
Asahi et al., (2015) "Survivin suppressant YM155 induces cell death via proteasomal degradation of c-Myc in multiple myeloma cells," 15th International Myeloma Workshop, e237, Sep. 23-26, 1 page.
Ashworth et al., (2010). "Deletion-based mechanisms of Notch1 activation in T-ALL: key roles for RAG recombinase and a conserved internal translational start site in Notch1," Blood, 116(25):5455-5464.
Beltran, (2014). "The N-myc Oncogene: Maximizing its Targets, Regulation, and Therapeutic Potential," Mol Cancer Res, 12(6):815-822.
Boskovski et al., (2013). "The heterotaxy gene GALNT11 glycosylates Notch to orchestrate cilia type and laterality," Nature, 504:456-459, including Methods and Extended Data, 16 pages.
Bundgaard, (1985). "Design of Prodrugs," pp. 7-9; 21-24, Elsevier Science Publishers, Amsterdam, 10 pages.

CAS Registry No. 781661-94-7, Nov. 16, 2004, 2 pages.
Cheng et al., (2016). "Survivin inhibitor YM155 suppresses gastric cancer xenograft growth in mice without affecting normal tissues," Oncotarget, 7(6):7096-7109.
Cheson et al., (2009). "Abstract 8502. Safety and efficacy of YM155 in diffuse large B-cell lymphoma (DLBCL)," Journal of Clinical Oncology, 15(27), 3 pages.
Chico et al., (2009). "Targeting protein kinases in central nervous system disorders," Nat Rev Drug Discov., 8(11):892-909, 39 pages.
Coiffier et al., (2016). "Diffuse large B-cell lymphoma: R-CHOP failure—what to do?" Hematology Am Soc Hematol Educ Program, (1):366-378.
Darzynkiewicz et al., (2001). "Flow Cytometry in Analysis of Cell Cycle and Apoptosis," Semin Hematol, 38:179-193.
Ellisen et al., (1991). "TAN-1, the Human Homolog of the *Drosophila* Notch Gene, Is Broken by Chromosomal Translocations in T Lymphoblastic Neoplasms," Cell, 66:649-661.
Extended European Search Report dated Jun. 27, 2022 for European Application No. 19849633.3, 6 pages.
Ferrarotto et al., (2016). "Activating NOTCH1 Mutations Define a Distinct Subgroup of Patients With Adenoid Cystic Carcinoma Who Have Poor Prognosis, Propensity to Bone and Liver Metastasis, and Potential Responsiveness to Notch1 Inhibitors," Journal of Clinical Oncology, 35(3):352-360.
Gall et al., (1969). "Formation and Detection of RNA-DNA Hybrid Molecules in Cytological Preparations," Proc Natl Acad Sci USA, 63(2):378-383.
Gautam et al., (2016). "Identification of selective cytotoxic and synthetic lethal drug responses in triple negative breast cancer cells," Molecular Cancer, 15:34, 16 pages.
Haydu et al., (2012). "An activating intragenic deletion in NOTCH1 in human T-ALL," Blood, 119(22):5211-5214.
Hidehiro et al., (2009). "Low-level copy gain versus amplification of myc oncogenes in medulloblastoma: utility in predicting prognosis and survival. Laboratory investigation," J Neurosurg Pediatr, 3(1):61-5. Abstract Only.
International Search Report and Written Opinion dated Apr. 22, 2021 for International Application No. PCT/US2021/016863, 11 pages.
International Search Report and Written Opinion dated Apr. 27, 2021 for International Application No. PCT/US2021/016861, 9 pages.
International Search Report and Written Opinion dated Dec. 13, 2021 for International Application No. PCT/US2021/050657, 12 pages.
International Search Report and Written Opinion dated Jun. 21, 2021 for International Application No. PCT/CN2020/117167, 12 pages.
International Search Report and Written Opinion dated Nov. 10, 2020 for International Application No. PCT/CN2020/074516, 10 pages.
International Search Report and Written Opinion dated Nov. 12, 2020 for International Application No. PCT/CN2020/074515, 9 pages.
Kallioniemi et al., (1992). "Comparative Genomic Hybridization for Molecular Cytogenetic Analysis of Solid Tumors," Science, 258:818-821, 5 pages.
Kawazu et al., (2017). "Integrative analysis of genomic alterations in triple-negative breast cancer in association with homologous recombination deficiency," PLoS Genet, 13(6):e1006853, 23 pages.
Liu et al., (2015). "Prognostic and biological significance of survivin expression in patients with diffuse large B-cell lymphoma treated with rituximab-CHOP therapy," Mod Pathol, (10):1297-1314.
Minematsu et al., (2009). "Carrier-Mediated Uptake of 1-(2-Methoxyethyl)-2-methyl-4,9-dioxo-3-(pyrazin-2-ylmethyl)-4,9-dihydro-1H-naphtho[2,3-d]imidazolium Bromide (YM155 Monobromide), a Novel Small-Molecule Survivin Suppressant, into Human Solid Tumor and Lymphoma Cells," Drug Metabolism and Disposition, 37(3):619-628.
Na et al., (2012). "YM155 Induces EGFR Suppression in Pancreatic Cancer," PLoS One, 7(6):e38625, 10 pages.

(56) References Cited

OTHER PUBLICATIONS

Nakahara et al., (2007). "YM155, a Novel Small-Molecule Survivin Suppressant, Induces Regression of Established Human Hormone-Refractory Prostate Tumor Xenografts," Cancer Res, 67(17):8014-8021.

Ohshima et al., (2017). "Integrated analysis of gene expression and copy number identified potential cancer driver genes with amplification dependent overexpression in 1,454 solid tumors," Scientific Reports, 7:641, 13 pages.

O'Neil et al., (2007). "FBW7 mutations in leukemic cells mediate NOTCH pathway activation and resistance to γ-secretase inhibitors," JEM, 204(8):1813-1824.

Parra et al., (1993). "High resolution visual mapping of stretched DNA by fluorescent hybridization," Nature Genetics, 5:17-21.

Pinkel et al., (2005). "Comparative Genomic Hybridization," Annu. Rev. Genomics Hum. Genet., 6:331-354.

Puente et al., (2015). "Non-coding recurrent mutations in chronic lymphocytic leukaemia," Nature, 526:519-524, including Methods, 6 pages.

Radic-Sarikas et al., (2017). "Lapatinib potentiates cytotoxicity of YM155 in neuroblastoma via inhibition of the ABCB1 efflux transporter," Scientific Reports, 7:3091, 8 pages.

Rosati et al., (2018). "NOTCH1 Aberrations in Chronic Lymphocytic Leukemia," Front. Oncol., 8:229, 20 pages.

Schouten et al., (2002). "Relative quantification of 40 nucleic acid sequences by multiplex ligation-dependent probe amplification," Nucleic Acids Research, 30(12):e57, 13 pages.

Sulis et al., (2008). "NOTCH1 extracellular juxtamembrane expansion mutations in T-ALL," Blood, 112:733-740.

Tao et al., (2012). "Survivin selective inhibitor YM155 induce apoptosis in SK-NEP-1 Wilms tumor cells," BMC Cancer, 12:619, 13 pages.

Thompson et al., (2007). "The SCFFBW7 ubiquitin ligase complex as a tumor suppressor in T cell leukemia," JEM, 204(8):1825-1835.

UnitProt, (2021). "UniProtKB No. P46531: Neurogenic locus notch homolog protein 1," available online at <https://www.uniprot.org/uniprotkb/P46531/entry>, 22 pages.

Van Agthoven et al., (2003). "A review of recruitment criteria, patient characteristics and results of CHOP chemotherapy in prospective randomized phase III clinical trials for aggressive non-Hodgkin's lymphoma," The Hematology Journal, 4:399-409.

Voges et al., (2016). "Effects of YM155 on survivin levels and viability in neuroblastoma cells with acquired drug resistance," Cell Death and Disease, 6:e2410, 11 pages.

Wang et al., (2015). "PEST Domain Mutations in Notch Receptors Comprise an Oncogenic Driver Segment in Triple-Negative Breast Cancer Sensitive to a γ-Secretase Inhibitor," Clin Cancer Res, 21(6):1487-1496.

Warrier et al., (2020). "Emerging Importance of Survivin in Stem Cells and Cancer: the Development of New Cancer Therapeutics," Stem Cell Reviews and Reports, 16:828-852.

Weng et al., (2004). "Activating Mutations of NOTCH 1 in Human T Cell Acute Lymphoblastic Leukemia," Science, 306:269-271.

Westhoff et al., (2009). "Alterations of the Notch pathway in lung cancer," PNAS, 106(52):22293-22298.

Woo et al., (2017). "YM155 enhances ABT-737-mediated apoptosis through Mcl-1 downregulation in Mcl-1-overexpressed cancer cells," Mol Cell Biochem, 429:91-102.

Yamanaka et al., (2011). "YM155, a selective survivin suppressant, inhibits tumor spread and prolongs survival in a spontaneous metastatic model of human triple negative breast cancer," International Journal of Oncology, 39:569-575.

Ye et al., (1993). "Alterations of a Zinc Finger-Encoding Gene, BCL-6, in Diffuse Large-Cell Lymphoma," Science, 262:747-750.

Zhao et al., (2011). "Survivin Inhibition Is Critical for Bcl-2 Inhibitor-Induced Apoptosis in Hepatocellular Carcinoma Cells," PLoS One, 6(8):e21980, 9 pages.

Zhao et al., (2013). "Computational tools for copy number variation (CNV) detection using next-generation sequencing data: features and perspectives," BMC Bioinformatics, 14(Suppl 11):S1, 16 pages.

Zhong et al., (2016). "NOTCH 1 is a poor prognostic factor for breast cancer and is associated with breast cancer stem cells," Oncotargets and Therapy, 9:6865-6871.

Berenbaum et al., (1977). "Synergy, additivism and antagonism in immunosuppression—critical review," Clin Exp Immunol., 28:1-18.

Weisenthal, (2012). "Synergy analysis of "classic" and newer drug combinations.," Human Tumor Assay Journal, available online at (http://weisenthal.org/synergy1.htm), Yetrieved on Mar. 14, 2012.

* cited by examiner

COMBINATION THERAPY FOR CANCERS WITH BRAF MUTATION

CROSS REFERENCE TO RELATED APPLICATION

This application is a national stage application under 35 U.S.C. § 371 of International Application No. PCT/CN2019/081674, filed internationally on Apr. 8, 2019, which claims the benefit of International Application No. PCT/CN2018/082191, filed Apr. 8, 2018, which is hereby incorporated by reference in its entirety.

FIELD OF INVENTION

The present disclosure relates generally to combination therapies for treating or delaying progression of cancers with a BRAF mutation and related compositions and kits.

BACKGROUND

The v-raf murine sarcoma viral oncogenes homolog B1 (BRAF) is a patent activator of the mitogen-activated protein kinase (MAPK)/extracellular signal-regulated kinase (ERK) signaling pathway, which is involved in the regulation of cell proliferation, differentiation, and survival in response to extracellular signaling. Cantwell-Dorris et al. (2011) *Mol. Cancer Ther.* 10, 385. This pathway can be activated when extracellular ligands bind epidermal growth factor receptor (EGFR), initiating the cascade of ERK signaling through RAS GTPase. Once RAS is engaged, it recruits and activates RAF (such as ARAF, BRAF, and CRAF), which phosphorylates MAPK/ERK kinase (MEK), triggering downstream ERK pathway. Oikonomou et al. (2014) *Oncotarget* 5, 11752.

BRAF mutation has been detected in a wide range of cancers including ~59% of malignant melanomas, ~45% of papillary thyroid cancer, ~18% of colorectal cancers (CRC), ~4% of ovarian cancer, ~2% of breast cancer, and ~3% of lung cancer, making it a potential therapeutic target. Davies et al. (2002) *Nature* 417, 949; Xing et al. (2005) *Endocr. Relat. Cancer* 12, 245. Mutations in BRAF occur most frequently at nucleotide 1976, leading to a change at a valine residue (V600). Davies et al. (2002) *Nature* 417, 949. Mutated BRAF can cause constitutive activation of MAPK/ERK kinase (MEK), which in turn phosphorylates ERK and leads to target gene transcription that promotes tumor cell growth and survival in absence of any extracellular stimuli. Hall et al. (2014) *Cancer Control* 21, 221; Cantwell-Dorris et al. (2011) *Mol. Cancer Ther.* 10, 385.

Chemotherapy, even highly aggressive regimen, has poor response in treating cancers with BRAF mutation. For example, in a clinical trial, patients with metastatic CRC received FOLFOXIRI plus bevacizumab, a highly aggressive regimen, but the survival for patients with BRAF mutant CRC was less than half compared to that of patients with wild-type tumors (median overall survival, 19.0 months vs. 41.7 months). Loupakis F, et al. (2014) *N Engl J Med.* 371, 1609.

BRAF inhibitors alone and in combination with MEK inhibitors are approved by the U.S. Food and Drug Administration (FDA) in treating metastatic melanoma cancers with BRAF mutations. Larkin et al. (2014) *N. Engl. J. Med.* 371, 1867; Robert et al. (2015) *N. Engl. J. Med.* 372, 30. To date, melanoma cancer with BRAF mutation V600K or V600E is the only cancer type with a BRAF mutation that has approved target therapy. However, the duration of response is limited due to the development of acquired and adaptive resistance. Manzano et al. (2016) *Ann. Transl. Med.* 4, 237; Barras (2015) *Biomarkers in Cancer* 7, 9. Study has shown that ERK can be reactivated through EGFR-mediated activation of RAS and CRAF, contributing to the resistance of cancer cells to BRAF inhibitors. Barras (2015) *Biomarkers in Cancer* 7, 9. In addition, it has been reported that the use of BRAF inhibitors may result in the development of secondary skin tumors, originating from a paradoxical activation of the MAPK pathway in cells without a BRAF mutation, although combining a BRAF inhibitor with a MEK inhibitor may decrease the incidence of BRAF-inhibitor-induced skin tumors. Chapman et al (2011) *N. Engl. J. Med.* 364, 2507; Robert et al. (2011) *Curr. Opin. Oncol.* 23, 177; Larkin et al. (2014) *N. Engl. J. Med.* 371, 1867. Recent and present clinical trials in cancers with BRAF mutation usually involve the combination of a BRAF inhibitor and other therapeutic drugs or candidates targeting different pathways such as EGFR, MEK, PI3K, as well as cytotoxic chemotherapy. Morris et al. (2013) *F1000Prime Rep.* 5, 11; Hyman D M, et al. (2015) *N. Engl. J. Med.* 373, 726.

Therefore, there remains a need for a robust therapy for treating cancer with BRAF mutations.

The disclosures of all publications, patents, patent applications and published patent applications referred to herein are hereby incorporated herein b reference in their entirety.

BRIEF SUMMARY

Provided herein are compositions comprising (a) an epidermal growth factor receptor (EGFR) inhibitor; (b) a mitogen-activated protein kinase (MEK) 1/2 inhibitor; and (c) a cyclin dependent kinase (CDK) 4/6 inhibitor; wherein the composition does not comprise a BRAF inhibitor. In some embodiments, the composition consists of (a) an epidermal growth factor receptor (EGFR) inhibitor; (b) a mitogen-activated protein kinase (MEK) 1/2 inhibitor; and (c) a cyclin dependent kinase (CDK) 4/6 inhibitor.

Also provided here are methods for treating or delaying progression of cancer in a subject comprising administering to the subject an effective amount of (a) an epidermal growth factor receptor (EGFR) inhibitor; (b) a mitogen-activated protein kinase (MEK) 1/2 inhibitor; and (c) a cyclin dependent kinase (CDK) 4/6 inhibitor, wherein the subject has cancer or is at risk of developing cancer that has a BRAF mutation. In some embodiments, the method does not comprise administering a BRAF inhibitor to the subject during the administrations of (a) an epidermal growth factor receptor (EGFR) inhibitor; (b) a mitogen-activated protein kinase (MEK) 1/2 inhibitor; and (c) a cyclin dependent kinase (CDK) 4/6 inhibitor. In some embodiments, the method does not comprise administering an additional therapeutic agent to the subject during the administrations of (a) an epidermal growth factor receptor (EGFR) inhibitor; (b) a mitogen-activated protein kinase (MEK) 1/2 inhibitor; and (c) a cyclin dependent kinase (CDK) 4/6 inhibitor.

Also provided here are methods for treating or delaying progression of cancer in a subject comprising administering to the subject an effective amount of osimertinib or a salt thereof, cobimetinib or a salt thereof, and palbociclib or a salt thereof, wherein the subject has cancer or is at risk of developing cancer that has a BRAF mutation. In some embodiments, the method does not comprise administering to the subject a BRAF inhibitor during the administrations of osimertinib or a salt thereof, cobimetinib or a salt thereof, and palbociclib or a salt thereof. In some embodiments, the method does not comprise administering to the subject an additional therapeutic agent during the administrations of osimertinib or a salt thereof, cobimetinib or a salt thereof, and palbociclib or a salt thereof. In some embodiments, osimertinib or a salt thereof, cobimetinib or a salt thereof, and palbociclib or a salt thereof are administered in one composition. In some embodiments, osimertinib or a salt thereof, cobimetinib or a salt thereof, and palbociclib or a salt thereof are administered continuously to the subject. In some embodiments, osimertibin or a salt thereof, cobimetinib or a salt thereof, and palbociclib or a salt thereof are administered intermittently to the subject.

In some embodiments, osimertinib or a salt thereof is administered to the subject in a daily dose of about 20-160 mg of osimertinib. In some embodiments, cobimetinib or a salt thereof is administered to the subject in a daily dose of about 20-60 mg of cobimetinib. In some embodiments, palbociclib or a salt thereof is administered to the subject in a daily dose of about 75-125 mg of palbociclib. In some embodiments, the subject is a human. In some embodiments, osimertinib or a salt thereof is administered to the subject in a daily dose of about 0.5-3 mg/kg of osimertinib. In some embodiments, cobimetinib or a salt thereof is administered to the subject in a daily dose of about 0.25-1 mg/kg of cobimetinib, in some embodiments, palbociclib or a salt thereof is administered to the subject in a daily dose of about 1-2.5 mg/kg of palbociclib.

Also provided here are methods for treating or delaying progression of cancer in a subject comprising administering to the subject an effective amount of cetuximab, cobimetinib or a salt thereof, and palbociclib or a salt thereof, wherein the subject has cancer or is at risk of developing cancer that has a BRAF mutation. In some embodiments, the method does not comprise administering to the subject a BRAF inhibitor during the administrations of cetuximab, cobimetinib or a salt thereof, and palbociclib or a salt thereof. In some embodiments, the method does not comprise administering to the subject an additional therapeutic agent during the administrations of cetuximab, cobimetinib or a salt thereof, and palbociclib or a salt thereof. In some embodiments, cetuximab, cobimetinib or a salt thereof, and palbociclib or a salt thereof are administered in one composition. In some embodiments, cetuximab, cobimetinib or a salt thereof, and palbociclib or a salt thereof are administered continuously to the subject. In some embodiments, cetuximab, cobimetinib or a salt thereof, and palbociclib or a salt thereof are administered intermittently to the subject.

In some embodiments, cetuximab is administered to the subject in 400 mg/m$^2$ infused over 120 minutes followed by 250 rug/m$^2$ weekly infused over 60 minutes. In some embodiments, the maximum infusion rate is about 10 mL/min. In some embodiments, cobimetinib or a salt thereof is administered to the subject in a daily dose of about 20-60 mg of cobimetinib. In some embodiments, palbociclib or a salt thereof is administered to the subject in a daily dose of about 75-125 mg of palbociclib. In some embodiments, cetuximab is administered to the subject in a weekly dose of about 150-400 mg/m$^2$ per subject. In some embodiments, the subject is a human. In some embodiments, cobimetinib or a salt thereof is administered to the subject in a daily dose of about 0.25-10 mg/kg of cobimetinib. In some embodiments, palbociclib or a salt thereof is administered to the subject in a daily dose of about 5-30 mg/kg of palbociclib.

In some embodiments, the cancer has a BRAF V600 mutation or a BRAF D581D mutation. In some embodiments, the BRAF V600 mutation is BRAF V600E, V600D, or V600K mutation. In some embodiments, the cancer is a malignant epithelial tumor or carcinoma. In some embodiments, the cancer is a carcinoma selected from one or more of a colon cancer, a gastric cancer, a lung cancer, a breast cancer, a pancreatic cancer, an oral cancer, a prostate cancer, a germline cancer, a rectal cancer, a liver cancer, a kidney cancer, a papillary thyroid cancer, and an ovarian cancer. In some embodiments, the cancer is a colorectal cancer. In some embodiments, the colorectal cancer is a stage IV colorectal cancer. In some embodiments, the colorectal cancer has a BRAF V600E or D581V mutation.

In some embodiments, the subject had received a BRAF inhibitor in a previous treatment cycle. In some embodiments, the subject has not received a BRAF inhibitor in a previous treatment cycle.

In some embodiments, the method provided herein reduces mean tumor volume. In some embodiments, the method provided herein reduces cancer cell growth and/or increase cancer cell-killing by about 20-99% more than administration of (a) an epidermal growth factor receptor (EGFR) inhibitor; (b) a mitogen-activated protein kinase (MSK) 1/2 inhibitor; or (c) a cyclin dependent kinase (CDK) 4/6 inhibitor alone. In some embodiments, the method provided herein reduces cancer cell growth and/or increase cancer cell-killing by about 20-99% more than administration of osimertinib or a salt thereof, cobimetinib or a salt thereof, or palbociclib or a salt thereof alone. In some embodiments, the method provided herein reduces cancer cell growth and/or increase cancer cell-killing by about 20-99% more than administration of cetuximab, cobimetinib or a salt thereof, or palbociclib or a salt thereof alone. In some embodiments, the method reduces tumor volume by about 20-95%. The method may comprise administering any compositions or kits described herein.

In another aspect, provided herein are compositions comprising (a) an epidermal growth factor receptor (EGFR) inhibitor; (b) a mitogen-activated protein kinase (MEK) 1/2 inhibitor; and (c) a cyclin dependent kinase (CDK) 4/6 inhibitor. In some embodiments, the composition comprises osimertinib or a salt thereof, cobimetinib or a salt thereof, and palbociclib or a salt thereof in some embodiments, the composition does not comprise a BRAF inhibitor. In some embodiments, the composition consists of osimertinib or a salt thereof, cobimetinib or a salt thereof, and palbociclib or a salt thereof. In some embodiments, the composition further comprises a pharmaceutically acceptable carrier, excipient, binder, or diluent, in some embodiments, the composition is formulated for oral administration to a subject. In some embodiments, the subject has cancer or is at or is at risk of developing cancer that has a BRAF mutation.

In another aspect, provided herein are kits comprising (a) an epidermal growth factor receptor (EGFR) inhibitor; (b) a mitogen-activated protein kinase (MEK) 1/2 inhibitor; and (c) cyclin dependent kinase (CDK) 4/6 inhibitor; wherein the kit does not comprises a BRAF inhibitor. In some embodiments, the kit consists of (a) an epidermal growth factor receptor (EGFR) inhibitor; (b) a mitogen-activated protein kinase (MEK) 1/2 inhibitor; and (c) a cyclin dependent kinase (CDK) 4/6 inhibitor.

In some embodiments, the kit comprises osimertinib or a salt thereof, cobimetinib or a salt thereof, and palbociclib or a salt thereof. In some embodiments, the kit does not comprise a BRAF inhibitor. In some embodiments, the kit consists of osimertinib or a salt thereof, cobimetinib or a salt thereof, and palbociclib or a salt thereof. In some embodiments, the kit comprises a pharmaceutical composition comprising osimertinib or a salt thereof and a pharmaceutically acceptable carrier, excipient, binder, or diluent. In some embodiments, the kit comprises a pharmaceutical composition comprising cobimetinib or a salt thereof and a pharmaceutically acceptable carrier, excipient, binder, or diluent. In some embodiments, the kit comprises a pharmaceutical composition comprising palbociclib or a salt thereof and a pharmaceutically acceptable carrier, excipient, binder, or diluent. In some embodiments, the osimertinib or a salt thereof is formulated for oral administration to a subject. In some embodiments, the cobimetinib or a salt thereof is formulated for oral administration to a subject. In some embodiments, the palbociclib or a salt thereof is formulated for oral administration to a subject. In some embodiments, the subject has cancer or is at or is at risk of developing cancer that has a BRAF mutation. In some embodiments, the osimertinib or a salt thereof, cobimetinib or a salt thereof, and palbociclib or a salt thereof are formulated in one composition. In some embodiments, osimertibin or a salt thereof, cobimetinib or a salt thereof, and palbociclib or a salt thereof are administered continuously to the subject. In some embodiments, osimertinib or a salt thereof, cobimetinib or a salt thereof, and palbociclib or a salt thereof are administered intermittently to the subject.

In some embodiments, osimertinib or a salt thereof, cobimetinib or a salt thereof, and palbociclib or a salt thereof are formulated as one composition. In some embodiments, osimertinib or a salt thereof, cobimetinib or a salt thereof, and palbociclib or a salt thereof are formulated as individual compositions. In some embodiments, osimertinib or a salt thereof and cobimetinib or a salt thereof are formulated as one composition. In some embodiments, osimertinib or a salt thereof and palbociclib or a salt thereof are formulated as one composition. In some embodiments, cobimetinib or a salt thereof and palbociclib or a salt thereof are formulated as one composition. In some embodiments, osimertinib or a salt thereof, cobimetinib or a salt thereof, and palbociclib or a salt thereof are formulated in liquid forms. In some embodiments, osimertinib or a salt thereof, cobimetinib or a salt thereof, and palbociclib or a salt thereof are formulated in solid forms.

In some embodiments, osimertinib or a salt thereof, cobimetinib or a salt thereof, and palbociclib or a salt thereof are administered as one composition. In some embodiments, osimertinib or a salt thereof, cobimetinib or a salt thereof, and palbociclib or a salt thereof are administered separately. In some embodiments, osimertinib or a salt thereof, cobimetinib or a salt thereof, and palbociclib or a salt thereof are administered simultaneously. In some embodiments, osimertinib or a salt thereof, cobimetinib or a salt thereof, and palbociclib or a salt thereof are administered continuously. In some embodiments, osimertinib or a salt thereof, cobimetinib or a salt thereof, and palbociclib or a salt thereof are administered intermittently.

In some embodiments, the kit comprises cetuximab, cobimetinib or a salt thereof, and palbociclib or a salt thereof. In some embodiments, the kit does not comprise a BRAF inhibitor. In some embodiments, the kit consists of cetuximab, cobimetinib or a salt thereof, and palbociclib or a salt thereof. In some embodiments, the kit comprises a pharmaceutical composition comprising cetuximab and a pharmaceutically acceptable carrier, excipient, binder, or diluent. In some embodiments, the kit comprises a pharmaceutical composition comprising cobimetinib or a salt thereof and a pharmaceutically acceptable carrier, excipient, binder, or diluent. In some embodiments, the kit comprises a pharmaceutical composition comprising palbociclib or a salt thereof and a pharmaceutically acceptable carrier, excipient, binder, or diluent. In some embodiments, cetuximab is formulated for administration to a subject via intravenous infusion. In some embodiments, cobimetinib or a salt thereof is formulated for oral administration to a subject. In some embodiments, palbociclib or a salt thereof is formulated for oral administration to a subject. In some embodiments, the subject has cancer or is at or is at risk of developing cancer that has a BRAF mutation. In some embodiments, cetuximab, cobimetinib or a salt thereof, and palbociclib or a salt thereof are formulated in different compositions. In some embodiments, cobimetinib or a salt thereof, and palbociclib or a salt thereof are formulated in one composition. In some embodiments, cetuximab, cobimetinib or a salt thereof, and palbociclib or a salt thereof are administered continuously to the subject. In some embodiments, cetuximab, cobimetinib or a salt thereof, and palbociclib or a salt thereof are administered intermittently to the subject. In some embodiments, cetuximab, cobimetinib or a salt thereof, and palbociclib or a salt thereof are administered to the subject with different dosing frequencies.

In some embodiments, cetuximab, cobimetinib or a salt thereof, and palbociclib or a salt thereof are formulated as one composition. In some embodiments, cetuximab, cobimetinib or a salt thereof, and palbociclib or a salt thereof are formulated as individual compositions. In some embodiments, cetuximab and cobimetinib or a salt thereof are formulated as one composition. In some embodiments, cetuximab and palbociclib or a salt thereof are formulated as one composition. In some embodiments, cobimetinib or a salt thereof and palbociclib or a salt thereof are formulated as one composition. In some embodiments, cetuximab, cobimetinib or a salt thereof, and palbociclib or a salt thereof are formulated in liquid forms. In some embodiments, cetuximab, cobimetinib or a salt thereof, and palbociclib or a salt thereof are formulated in solid forms.

In some embodiments, cetuximab, cobimetinib or a salt thereof, and palbociclib or a salt thereof are administered as one composition. In some embodiments, cetuximab, cobimetinib or a salt thereof, and palbociclib or a salt thereof are administered separately. In some embodiments, cetuximab, cobimetinib or a salt thereof, and palbociclib or a salt thereof are administered simultaneously. In some embodiments, cetuximab, cobimetinib or a salt thereof, and palbociclib or a salt thereof are administered continuously. In some embodiments, cetuximab, cobimetinib or a salt thereof, and palbociclib or a salt thereof are administered intermittently. In some embodiments, cetuximab, cobimetinib or a salt thereof, and palbociclib or a salt thereof are administered with different dosing frequencies.

In some embodiments, the kit comprises a package insert containing instructions regarding indications, usage, dosage, administration, contraindications, other medicaments to be combined with the packaged product, and/or warnings concerning the use of such medicaments.

DETAILED DESCRIPTION

Figure 1:
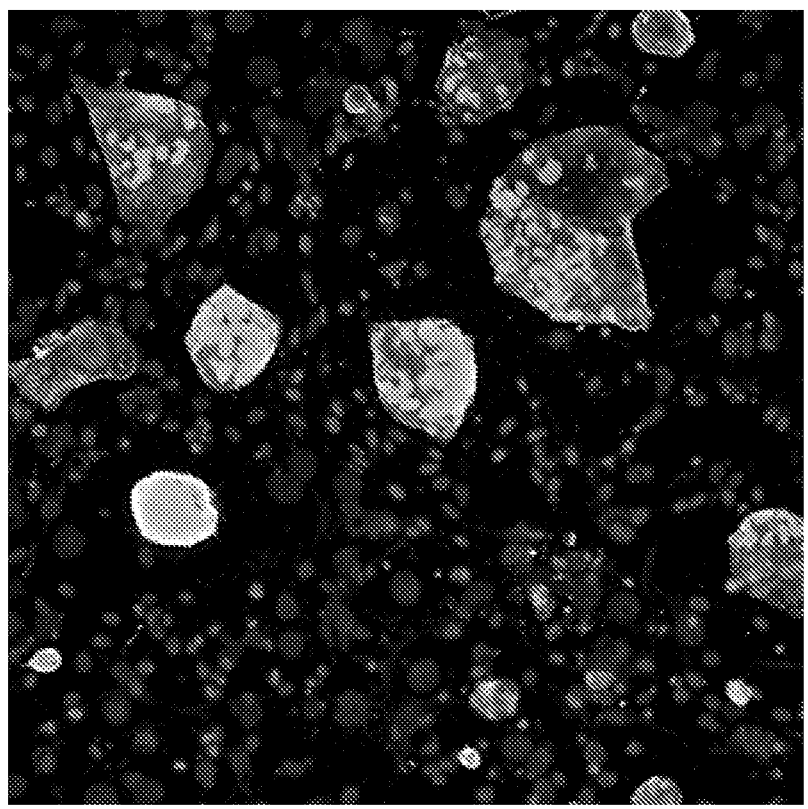
FIG. 1 shows a representative image of stained tumor cells obtained by a high-content screening (HCS) platform.

The present description is based on the inventor's data showing that a combination of an epidermal growth factor receptor inhibitor (such as osimertinib or cetuximab), a mitogen-activated protein kinase 1/2 inhibitor (such as cobimetinib, trametinib or TAK-733) and a cyclin dependent kinase 4/6 inhibitor (such as palbociclib) provides a robust therapy for a method of treating or delaying progression of cancer with a BRAF mutation. Particularly, such a combination therapy does not require a BRAF inhibitor. The combination therapy described herein has surprisingly demonstrated a synergistic effect toward cancers with a BRAF mutation and a robust efficacy in reducing the tumor volumes by up to about 95% in well-established animal models, despite the fact that none of the compounds in the combination is an inhibitor of the mutant BRAF The description also provides compositions and kits that can be used for carrying out this combination therapy.

I. Definitions

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to particular method steps, reagents, or conditions are specifically embraced by the present disclosure and are disclosed herein just as if each and every combination was individually and explicitly disclosed.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense. It is also understood that aspects and embodiments of the invention described herein may include "consisting" and/or "consisting essentially of" aspects and embodiments.

It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

As used herein, a subject "at risk" of developing a disease may or may not have detectable disease, or symptoms of disease, and may or may not have displayed detectable disease or symptoms of disease prior to the treatment methods described herein. A subject "at risk" has one or more risk factors, which are measurable parameters that correlate with development of a disease (such as cancer), as described herein and known in the art. A subject "at risk" may have one or more risk factors. A subject having one or more risk factors has higher probability of developing the disease than a subject without one or more risk factors.

As used herein, "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include but are not limited to squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Examples of cancer may include primary tumors of any of the above types of cancer or metastatic tumors at a second site derived from any of the above types of cancer. Included in this definition are benign and malignant cancers as well as dormant tumors or micrometastases.

The terms "neoplastic cell", "tumor cell" or "cancer cell", used either in the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

As used herein, a "carrier" includes pharmaceutically acceptable carriers, excipients, or stabilizers that are non-toxic to the cell or mammal being exposed thereto at the dosages and concentrations employed. Often the physiologically acceptable carrier is an aqueous pH buffered solution. Non-limiting examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, "delaying progression" of a disease means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed. A method that "delays" development of cancer is a method that reduces probability of disease development in a given time frame and/or reduces the extent of the disease in a given time frame, when compared to not using the method. Such comparisons are typically based on clinical studies, using a statistically significant number of subjects. Cancer development can be detectable using standard methods, including, but not limited to, computerized axial tomography (CAT scan), Magnetic Resonance Imaging (MRI), ultrasound, clotting tests, arteriography, biopsy, urine cytology, and cystoscopy. Development may also refer to cancer progression that may be initially undetectable and includes occurrence, recurrence, and onset.

As used herein, the term "effective amount" or "therapeutically effective amount" of a substance is at least the minimum concentration required to effect a measurable improvement or prevention of a particular disorder. An effective amount herein may vary according to factors such as the disease state, age, sex, and weight of the patient, and the ability of the substance to elicit a desired response in the individual. An effective amount is also one in which any toxic or detrimental effects of the treatment are outweighed by the therapeutically beneficial effects. In reference to cancer, an effective amount comprises an amount sufficient to cause a tumor to shrink and/or to decrease the growth rate of the tumor (such as to suppress tumor growth) or to prevent or delay other unwanted cell proliferation in cancer. In some embodiments, an effective amount is an amount sufficient to delay development of cancer. In some embodiments, an effective amount is an amount sufficient to prevent or delay recurrence. In some embodiments, an effective amount is an amount sufficient to reduce recurrence rate in the individual. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit slow to some extent and preferably stop) tumor metastasis; (v) inhibit tumor growth; (vi) prevent or delay occurrence and/or recurrence of tumor; (vii) reduce recurrence rate of tumor, and/or (viii) relieve to some extent one or more of the symptoms associated with the cancer. An effective amount can be administered in one or more administrations. For purposes of this disclosure, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, the term "inhibitor" or "antagonist" refers to biological or chemical substance that interferes with or otherwise reduces the physiological and/or biochemical action of another biological or chemical molecule. In some embodiments, the inhibitor or antagonist specifically binds to the other molecule.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

A "pharmaceutically acceptable salt" is a salt form that is non-toxic, biologically tolerable, or otherwise biologically suitable for administration to the subject. See generally Berge et al. (1977) *J. Pharm. Sci.* 66, 1. Particular pharmaceutically acceptable salts are those that are pharmacologically effective and suitable for contact with the tissues of subjects without undue toxicity, irritation, or allergic response. Pharmaceutically acceptable salts include, without limitation, acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like. These salts may be derived from inorganic or organic acids. Non-limiting examples of pharmaceutically acceptable salts include, without limitation, sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfbnates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. In some embodiments, pharmaceutically acceptable salts are formed when an acidic proton present in the parent compound either is replaced by a metal ion, e.g., an alkali metal ion, an alkaline earth ion, or an aluminum ion; or coordinates with an organic base. Salts derived from pharmaceutically acceptable organic non-toxic bases include, without limitation, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, trimethamine, dicyclohexylamine, caffeine, procaine, hydrabamine, choline, betaine, ethylenediamine, glucosamine, N-ethylglucamine, N-methylglucamine, theobromine, purines, piperazine, piperidine, N-ethylpiperidine, polyamine resins, amino acids such as lysine, arginine, histidine, and the like. Examples of pharmaceutically acceptable base addition salts include those derived from inorganic bases such as sodium, potassium, lithium, ammonium, calcium, magnesium, iron, zinc, copper, manganese, aluminum salts and the like. In some embodiments, the organic non-toxic bases are L-amino acids, such as L-lysine and L-arginine, tromethamine, N-ethylglucamine and N-methylglucamine. Acceptable inorganic bases include, without limitation, aluminum hydroxide, calcium hydroxide, potassium hydroxide, sodium carbonate, sodium hydroxide, and the like. Lists of other suitable pharmaceutically acceptable salts are found in *Remington's Pharmaceutical Sciences*, 17th Edition, Mack Publishing Company, Easton, Pa., 1985.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

A "subject," "patient" or "individual" includes a mammal, such as a human or other animal, and typically is human. In some embodiments, the subject, e.g., patient, to whom the therapeutic agents and compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent, a dog, a cat, a farm animal, such as a cow or a horse, etc.

As used herein, a "tissue sample" or "cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ, such as a cancer or tumor tissue. The tissue sample may contain compounds which are not naturally intermixed with the tissue in nature such as preservatives, anticoagulants, buffers, fixatives, nutrients, antibiotics, or the like.

As used herein, the term "treatment" refers to clinical intervention designed to have beneficial and desired effects to the natural course of the individual or cell being treated during the course of clinical pathology. For the purpose of this disclosure, desirable effects of treatment include, without limitation, decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, increasing cancer cell-killing, decreasing symptoms resulting from the disease, preventing spread of diseases, preventing recurrence of disease, increasing the quality of life of those suffering from the disease, decreasing the dose of other medications required to treat the disease, delaying the progression of the disease, and/or prolonging survival of individuals.

II. Methods of Treating and Delaying Progression of Cancer with BRAF Mutation

Provided herein are methods for treating or delaying progression of cancer in a subject comprising administering to the subject an effective amount of (a) an epidermal growth factor receptor (EGFR) inhibitor; (b) a mitogen-activated protein kinase (MEK) 1/2 inhibitor; and (c) a cyclin dependent kinase (CDK) 4/6 inhibitor; wherein the subject has cancer or is at risk of developing cancer that has a BRAF mutation.

In some embodiments, (a) is a small molecule or antibody (or antigen-binding fragment thereof) which specifically binds to EGFR or a ligand thereof, and is optionally selected from one or more of cetuximab, panitumumab, zalutumumab, nimotuzumab, matuzumab, erlotinib, gefitinib, afatinib, lapatinib, osimertinib, brigatinib, and icotinib. In some embodiments, (b) is a small molecule or antibody (or antigen-binding fragment thereof; which specifically binds to a MEK 1/2 or a ligand thereof, and is optionally selected from one or more of trametinib, selumetinib, TAK-733, CI-1040, PD0325901, MEK162, AZD8330, GDC-0623, refametinib, pimasertib, RO4987655, RO5126766, WX-554, HL-085 and cobimetinib. See Chen et al. (2017) *Molecules* 22, 1551. In some embodiments, (c) is a small molecule or antibody (or antigen-binding fragment thereof) which specifically binds to a CDK 4/6 or a ligand thereof, and is optionally selected from one or more of palbociclib, ribociclib, and abemaciclib. In some embodiments, the method does not comprise administering a BRAF inhibitor to the subject during the administrations of (a) an epidermal growth factor receptor (EGFR) inhibitor; (b) a mitogen-activated protein kinase (MEK) 1/2 inhibitor; and (c) a cyclin dependent kinase (CDK) 4/6 inhibitor. In some embodiments, the method does not comprise administering an additional therapeutic agent during the administrations of (a) an epidermal growth factor receptor (EGFR) inhibitor; (b) a mitogen-activated protein kinase (MEK) 1/2 inhibitor; and (c) a cyclin dependent kinase (CDK) 4/6 inhibitor. In some embodiments, the subject had received a BRAF inhibitor during a previous treatment cycle. In some embodiments, the subject has not received a BRAF inhibitor during a previous treatment cycle. In some embodiments, the subject is a human.

In one aspect, the method disclosed here can be used to treat or delay progression of a cancer that has a BRAF mutation. BRAF is a serine-threonine kinase and BRAF mutations have been found in 28 primary cancers, including 6 primary melanomas, 12 melanoma short-term cultures, colorectal cancer, ovarian cancer, gliomas, lung cancer, breast cancer, sarcoma, etc. Without wishing to be bound to theory, it is proposed that BRAF mutations lead to constitutive BRAF kinase activity, phosphorylation of MEK and ERK kinases, and sustained MAPK pathway signaling, leading to tumor cell proliferation and survival. BRAF has been reported to be mutated at several sites, but the vast majority of mutated BRAF are V600E, corresponding to a T to A transversion mutation at nucleotide 1796. BRAF mutation V600K, V600D, and D581V have also been observed. Detection of these mutations can be performed using conventional methods, such as the non-limiting example reported in Lasota et al. (2015) *Am. J. Surg. Pathol.* 38, 1235. In some embodiments, BRAF mutation is detected in tissue or cell samples containing cancer cells from a subject. In some embodiments, the BRAF mutation is a somatic mutation. In some embodiments, the method is used to treat or delay progression of a cancer that has a BRAF V600E mutation. In some embodiments, the method is used to treat or delay progression of a cancer that has a BRAF V600D mutation. In some embodiments, the method is used to treat or delay progression of a cancer that has a BRAF V600K mutation. In some embodiments, the method is used to treat or delay progression of a cancer that has a BRAF D581V mutation. In some embodiments, the method does not comprise administering a BRAF inhibitor to the subject during the administrations of osimertinib or a salt thereof, cobimetinib or a salt thereof, and palbociclib or a salt thereof. In some embodiments, the method does not comprise administering an additional therapeutic agent during the administrations of osimertinib or a salt thereof, cobimetinib or a salt thereof, and palbociclib or a salt thereof. In some embodiments, the subject had received a BRAF inhibitor during a previous treatment cycle. In some embodiments, the subject has not received a BRAF inhibitor during a previous treatment cycle.

In some embodiments, the cancer is an adenocarcinoma, a squamous cell carcinoma, an adenosquamous carcinoma, arranaplastic carcinoma, a large cell carcinoma, and a small cell carcinoma. In some embodiments, the cancer is melanoma and carcinoma, such as an epithelial neoplasm, a squamous cell neoplasm, a basal cell neoplasm, a transitional cell carcinoma, an adenocarcinoma, an adnexal or skin appendage neoplasm, a mucoepidermoid neoplasm, a cystic, mucinous, or Serous neoplasm, a ductal, lobular, or medullary neoplasm, an acinar cell neoplasm, and a complex epithelial neoplasm. In some embodiments, the carcinoma is a colon cancer, a gastric cancer, a lung cancer, a breast cancer, a pancreatic cancer, an oral cancer, a prostate cancer, a germline cancer, a rectal cancer, a liver cancer, a kidney cancer, and an ovarian cancer. In some embodiments, the cancer is a late stage cancer, such as stage IV colorectal cancer. In some embodiments, the cancer is an advanced colorectal cancer.

Also provided here are methods for treating or delaying progression of cancer in a subject comprising administering to the subject an effective amount of osimertinib or a salt thereof, cobimetinib or a salt thereof, and palbociclib or a salt thereof, wherein the subject has cancer or is at risk of developing cancer that has a BRAF mutation. In another aspect, provided here are methods for treating or delaying progression of cancer in a subject comprising administering to the subject an effective amount of cetuximab, cobimetinib or a salt thereof, and palbociclib or a salt thereof, wherein the subject has cancer or is at risk of developing cancer that has a BRAF mutation. In another aspect, provided here are methods for treating or delaying progression of cancer in a subject comprising administering to the subject an effective amount of cetuximab, TAK-733 or a salt thereof and palbociclib or a salt thereof, wherein the subject has cancer or is at risk of developing cancer that has a BRAF mutation. In another aspect, provided here are methods for treating or delaying progression of cancer in a subject comprising administering to the subject an effective amount of osimertinib or a salt thereof, TAK-733 or a salt thereof and palbociclib or a salt thereof, wherein the subject has cancer or is at risk of developing cancer that has a BRAF mutation. In another aspect, provided here are methods for treating or delaying progression of cancer in a subject comprising administering to the subject an effective amount of cetuximab, trametinib or a salt thereof and palbociclib or a salt thereof, wherein the subject has cancer or is at risk of developing cancer that has a BRAF mutation. In another aspect, provided here are methods for treating or delaying progression of cancer in a subject comprising administering to the subject an effective amount of osimertinib or a salt thereof, trametinib or a salt thereof and palbociclib or a salt thereof, wherein the subject has cancer or is at risk of developing cancer that has a BRAF mutation.

Osimertinib is an oral, third-generation EGFR inhibitor approved for treating non-small cell lung cancer harboring EGFR mutations by U.S. FDA and European Commission (EC). Osimertinib targets EGFR tyrosine kinase inhibitor (TKI)-sensitizing mutations and particularly T790M that often contributes to acquired resistance to EGER TKI therapy. Cobimetinib is a MEK inhibitor approved by U.S. FDA to be used in combination with vemurafenib, a BRAF inhibitor, for treating metastatic melanoma with BRAF V600E or V600K mutation. Cobimetinib and vemurafenib target different components of the MAPK/ERK pathway: MEK and BRAF respectively. Palbociclib is a CDK4/6 inhibitor approved by U.S. FDA for treating hormone receptor (FIR) positive, human epidermal growth factor receptor 2 (HER2) negative advanced or metastatic breast cancer in combination with an aromatase inhibitor as initial endocrine based therapy in postmenopausal women. Cetuximab is a chimeric monoclonal antibody given by intravenous infusion and an EGFR inhibitor approved by U.S. FDA in 2009 for treatment of colon cancer with wild-type KRAS. TAK-733 is an orally bioavailable, non-ATP-competitive small-molecule MEK1/2 inhibitor that completed a Phase I clinical study. Trametinib is a MEK inhibitor approved by U.S. FDA to be used as a single agent or in combination with debrafebnib, a BRAF inhibitor, for treating, melanoma with BRAF V600E or V600K mutation. The structures of osimertinib, TAK-733, cobimetinib, trametinib and palbociclib are shown below.

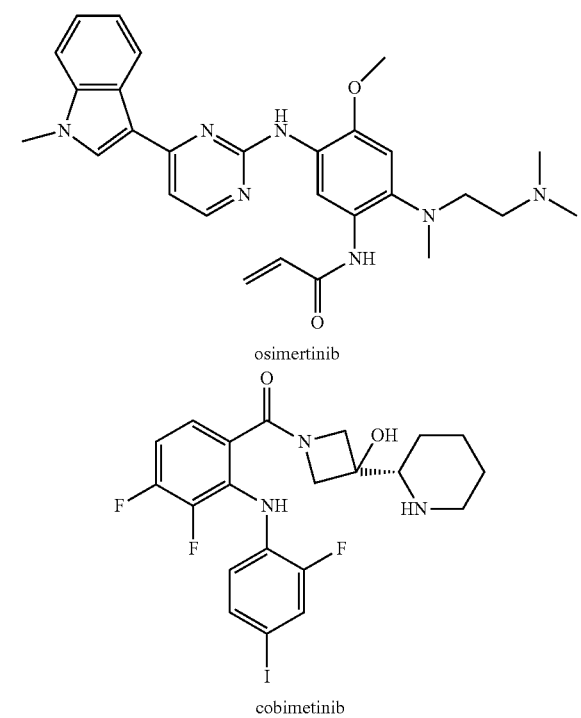

osimertinib cobimetinib

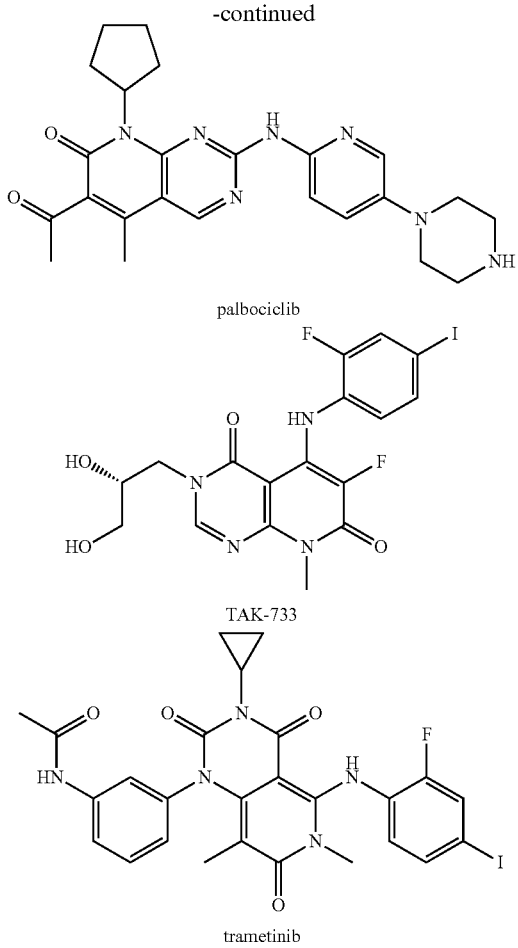

palbociclib

TAK-733 trametinib

In some embodiments, the method comprises administering salts of osimertinib, cobimetinib, and palbociclib. In some embodiments, the salts are pharmaceutically acceptable salts. Non-limiting examples of pharmaceutically acceptable salts include, without limitation, sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, mesylates propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. In some embodiments, the pharmaceutically acceptable salts are fumarates. In some embodiments, the pharmaceutically acceptable salts are mesylates. In some embodiments, the method comprises administering osimertinib, cobimetinib, and fumarate salt of palbociclib. In some embodiments, the method comprises administering osimertinib, fumarate salt of cobimetinib, and palbociclib. In some embodiments, the method comprises administering osimertinib and fumarate salts of cobimetinib and palbociclib. In some embodiments, the method comprises administering mesylate salt of osimertinib and fumarate salts of cobimetinib and palbociclib. In some embodiments, the method comprises administration of osimertinib, cobimetinib, and palbociclib or a solvate or a salt of any of the foregoing.

The method may comprise administering any compositions or kits described herein.

In another aspect, the method comprises administering an effective amount of osimertinib or a salt thereof, cobimetinib or a salt thereof, and palbociclib or a salt thereof. In some embodiments, the daily dosage of osimertinib or a salt thereof is in the amount of about 0.25-0.5 mg/kg, about 0.5-1 mg/kg, about 1-1.5 mg/kg, about 1.5-2 mg/kg, about 2-2.5 mg/kg, about 2.5-3 mg/kg, about 3-3.5 mg/kg, about 3.5-4 mg/kg, or about 0.5-3 mg/kg of osimertinib. In some embodiments, the daily dosage of osimertinib or a salt thereof is in the amount of about 20 mg, about 40 mg, about 80 mg, or about 160 mg of osimertinib. In some embodiments, the daily dosage of osimertinib or a salt thereof is in the amount of less than about 20 mg, about 40 mg, about 80 mg, or about 160 mg of osimertinib. In some embodiments, the dosage of osimertinib or a salt thereof is in the amount of about 20-240 mg, about 20-40 mg, about 40-80 mg, about 80-160 mg, about 160-240 mg or about 40-160 mg of osimertinib. In some embodiments, the daily dosage of osimertinib or a salt thereof is in the amount of about 0.6-2.7 mg/kg of osimertinib. In some embodiments, osimertinib is in its mesylate salt form. The amounts of the inhibitor described herein and throughout the specification refer to the amount of the inhibitor without taking into consideration of the weight of the counterions if the inhibitor exists in a salt form. For example, the term "80 mg of osimertinib" could include, without limitation, 80 mg of osimertinib in a salt-free form or 95.4 mg of osimertinib mesylate.

In some embodiments, the daily dosage of cobimetinib or a salt thereof is in the amount of about 0.1-0.25 mg/kg, about 0.25-0.5 mg/kg, about 0.5-0.75 mg/kg, about 0.75-1 mg/kg, about 1-1.25 mg/kg, about 1.25-1.5 mg/kg, about 1.5-1.75 mg/kg, about 1.75-mg/kg, or about 0.25-1 mg/kg of cobimetinib. In some embodiments, the daily dosage of cobimetinib or a salt thereof is in the amount of about 10 mg, about 20 mg, about 40 mg, or about 60 mg of cobimetinib. In some embodiments, the daily dosage of cobimetinib or a salt thereof is in the amount of less than about 10 mg, about 20 mg, about 40 mg, or about 60 mg of cobimetinib. In some embodiments, the daily dosage of cobimetinib or a salt thereof is in the amount of about 3.5-100 mg, about 3.5-10 mg, about 10-20 mg, about 20-40 mg, about 40-60 mg, about 20-60 mg, or about 60-100 mg of cobimetinib. In some embodiments, the daily dosage of cobimetinib or a salt thereof is in the amount of about 0.3-1 mg/kg of cobimetinib. In some embodiments, the cobimetinib is in its hemifumarate salt form.

In some embodiments, the daily dosage of palbociclib or a salt thereof is in the amount of about 0.5-1 mg/kg, about 1.5-2 mg/kg, about 2-2.5 mg/kg, about 2.5-3 mg/kg, about 3-3.5 mg/kg, about 1-2.5 mg/kg, about 1-3 mg/kg, or about 3-5 mg/kg of palbociclib. In some embodiments, the daily dosage of palbociclib or a salt thereof is in the amount of about 50 mg, about 75 mg, about 100 mg, or about 125 mg of palbociclib. In some embodiments, the daily dosage of palbociclib or a salt thereof is in the amount of less than about 50 trig, about 75 mg, about 100 mg, or about 125 mg of palbociclib. In some embodiments, the daily dosage of palbociclib or a salt thereof is in the amount of about 25-225 mg, about 25-50 mg, about 50-75 mg, about 75-125 mg, about 125-150 mg about 150-200 mg, or about 200-225 mg of palbociclib. In some embodiments, the daily dosage of palbociclib or a salt thereof is in the amount of about 1.25-2.1 mg/kg of palbociclib. In some embodiments, the method comprises administration of osimertinib or a solvate or a salt thereof, cobimetinib or a solvate or a salt thereof, and palbociclib or a solvate or a salt thereof.

In some embodiments, the daily dosage of osimertinib or a salt thereof is in the amount that is about at greater than about 20%, or greater than about 25%, or greater than about 30%, or greater than about 35%, or greater than about 40%, or greater than about 43%, or greater than about 50%, or greater than about 55%, or greater than about 60%, or greater than about 65%, or greater than about 70%, or greater than about 75%, or greater than about 80%, or greater than about 85%, or greater than about 90%, or greater than 95% by weight of the combined daily dosage of osimertinib, cobimetinib, and palbociclib or salts of the foregoing. In some embodiments, the daily dosage of osimertinib or a salt thereof is in the amount that is about at less than 20%, or less than about 25%, or less than about 30%, or less than about 35%, or less than about 40%, or less than about 45%, or less than about 50%, or less than about 55%, or less than about 60%, or less than about 65%, or less than about 70%, or less than about 75%, or less than about 80%, or less than about 85%, or less than about 90%, or less than 95% by weight of the combined daily dosage of osimertinib, cobimetinib, and palbociclib or salts of the foregoing.

In some embodiments, the daily dosage of cobimetinib or a salt thereof is in the amount that is about at greater than about 20%, or greater than about 25%, or greater than about 30%, or greater than about 35%, or greater than about 40%, or greater than about 45%, or greater than about 50%, or greater than about 55%, or greater than about 60%, or greater than about 65%, or greater than about 70%, or greater than about 75%, or greater than about 80%, or greater than about 85%, or greater than about 90%, or greater than 95% by weight of the combined daily dosage of osimertinib, cobimetinib, and palbociclib or salts of the foregoing. In some embodiments, the daily dosage of cobimetinib or a salt thereof in the amount that is about at less than 20%, or less than about 25%, or less than about 30%, or less than about 35%, or less than about 40%, or less than about 45%, or less than about 50%, or less than about 55%, or less than about 60%, or less than about 65%, or less than about 70%, or less than about 75%, or less than about 80%, or less than about 85%, or less than about 90%, or less than 95% by weight of the combined daily dosage of osimertinib, cobimetinib, and palbociclib or salts of the foregoing.

In some embodiments, the daily dosage of palbociclib or a salt thereof is in the amount that is about at greater than about 20%, or greater than about 25%, or greater than about 30%, or greater than about 35%, or greater than about 40%, or greater than about 45%, or greater than about 50%, or greater than about 55%, or greater than about 60%, or greater than about 65%, or greater than about 70%, or greater than about 75%, or greater than about 80%, or greater than about 85%, or greater than about 90%, or greater than 95% by weight of the combined daily dosage of osimertinib, cobimetinib, and palbociclib or salts of the foregoing. In some embodiments, the daily dosage of palbociclib or a salt thereof is in the amount that is about at less than 20%, or less than about 25%, or less than about 30%, or less than about 35%, or less than about 40%, or less than about 45%, or less than about 50%, or less than about 55%, or less than about 60%, or less than about 65%, or less than about 70%, or less than about 75%, or less than about 80%, or less than about 85%, or less than about 90%, or less than 95% by weight of the combined daily dosage of osimertinib, cobimetinib, and palbociclib or salts of the foregoing.

In another aspect, the method comprises administering an effective amount of cetuximab, cobimetinib or a salt thereof, and palbociclib or a salt thereof. In some embodiments, the dosage of cetuximab is in the amount of about 0.1-20 mg/kg, about 0.1-0.5 mg/kg, about 0.5-1 mg/kg, about 1-2 mg/kg, about 2-3 mg/kg, about 3-S mg/kg, about 5-7.5 mg/kg, about 7.5-10 mg/kg, about 10-15 mg/kg, about 15-20 mg/kg, or about 0.1-10 mg/kg. In some embodiments, the dosage of cetuximab is about 150-200 mg/m$^2$, about 200-250 mg/m$^2$, about 250-300 mg/m$^2$, about 300-400 mg/m$^2$, about 400-500 mg/m$^2$, about 500-750 mg/m$^2$, about 150-250 mg/m$^2$, about 250-400 mg/m$^2$, or about 400-750 mg/m$^2$, In some embodiments, cetuximab is infused over 30-180 minutes, about 30-60 minutes, about 60-120 minutes, or about 120-180 minutes. In some embodiments, the maximum infusion rate is about 5 mL/min or about 10 mL/min. In some embodiments, cetuximab is administered about every day, about every week, about every two weeks, about every three week, or about every four weeks. In some embodiments, the dosage of cetuximab is about 500 mg/m$^2$ infused over 60-120 minutes every two weeks. In some embodiments, cetuximab is administered in accordance with a schedule comprising an initial dose followed by several subsequent doses. In some embodiments, the initial dose is about 250-500 mg/m$^2$, about 250-300 mg/m$^2$, about 300-400 mg/m$^2$ or about 400-500 mg/m$^2$. In some embodiments, the initial dose is about 250 mg/m$^2$, about 400 mg/m$^2$ or about 500 mg/m$^2$. In some embodiments, the subsequent dose is about 50-300 mg/m$^2$, about 50-150 mg/m$^2$, about 150-200 mg/m$^2$ or about 200-300 mg/m$^2$. In some embodiments, the subsequent dose is about 50 mg/m$^2$, about 150 mg/m$^2$ or about 250 mg/m$^2$. In some embodiments, cetuximab is administered in 400 mg/m$^2$ infused over 120 minutes followed by 250 mg/m$^2$ weekly infused over 60 minutes. In some embodiments, cetuximab is administered in 400 mg/m$^2$ infused over 120 minutes followed by 150 mg/m$^2$ weekly infused over 60 minutes.

In some embodiments, the daily dosage of cobimetinib or a salt thereof is in the amount of about 0.1-0.25 mg/kg, about 0.25-0.5 mg/kg, about 0.5-0.75 mg/kg, about 0.75-1 mg/kg, about 1-1.25 mg/kg, about 1.25-1.5 mg/kg, about 1.5-1.75 mg/kg, about 1.75-2 mg/kg, or about 0.25-1 mg/kg of cobimetinib. In some embodiments, the daily dosage of cobimetinib or a salt thereof is in the amount of about 10 mg, about 20 mg, about 40 mg, or about 60 mg of cobimetinib. In some embodiments, the daily dosage of cobimetinib or a salt thereof is in the amount of less than about 10 mg, about 20 mg, about 40 mg, or about 60 mg of cobimetinib. In some embodiments, the daily dosage of cobimetinib or a salt thereof is in the amount of about 3.5-100 mg, about 3.5-10 mg, about 10-20 mg, about 20-40 mg, about 40-60 mg, about 20-60 mg, or about 60-100 mg of cobimetinib. In some embodiments, the daily dosage of cobimetinib or a salt thereof is in the amount of about 0.3-1 mg/kg of cobimetinib. In some embodiments, the cobimetinib is in its hemifumarate salt form.

In some embodiments, the daily dosage of palbociclib or a salt thereof is in the amount of about 0.5-1 mg/kg, about 1.5-2 mg/kg, about 2-2.5 mg/kg, about 2.5-3 mg/kg, about 3-3.5 mg/kg, about 1-2.5 mg/kg, about 1-3 mg/kg, or about 3-5 mg/kg of palbociclib. In some embodiments, the daily dosage of palbociclib or a salt thereof is in the amount of about 50 mg, about 75 mg, about 100 mg, or about 125 mg of palbociclib. In some embodiments, the daily dosage of palbociclib or a salt thereof is in the amount of less than about 50 mg, about 75 mg, about 100 mg, or about 125 mg of palbociclib. In some embodiments, the daily dosage of palbociclib or a salt thereof is in the amount of about 25-225 mg, about 25-50 mg, about 50-75 mg, about 75-125 mg, about 125-150 mg about 150-200 mg, or about 200-225 mg of palbociclib. In some embodiments, the daily dosage of palbociclib or a salt thereof is in the amount of about 1.25-2.1 mg/kg of palbociclib. In some embodiments, the method comprises administration of cetuximab, cobimetinib or a solvate or a salt thereof, and palbociclib or a solvate or a salt thereof.

In another aspect, the method comprises administering an effective amount of cetuximab, TAK-733 or a salt thereof and palbociclib or a salt thereof. In some embodiments, the daily dosage of TAK-733 or a salt thereof is in the amount of in the amount of about 0.001-1 mg/kg, about 0.001-0.002 mg/kg, about 0.002-0.005 mg/kg, about 0.005-0.01 mg/kg, about 0.01-0.05 mg/kg, about 0.05-0.1 mg/kg, about 0.1-0.2 mg/kg, about 0.2-0.3 mg/kg, about 0.3-0.4 mg/kg, about 0.4-0.5 mg/kg, about 0.5-0.6 mg/kg, about 0.6-0.7 mg/kg, about 0.7-0.8 mg/kg, about 0.8-0.9 mg/kg, or about 0.9-1 mg/kg of TAK-733. In some embodiments, the daily dosage of TAK-733 or a salt thereof is in the amount of about 10 mg, about 15 mg, about 20 mg, or about 25 mg of TAK-733. In some embodiments, the daily dosage of TAK-733 or a salt thereof is in the amount of less than about 10 mg, about 15 mg, about 20 mg, or about 25 mg of TAK-733. In some embodiments, the daily dosage of TAK-733 or a salt thereof is in the amount of about 0.1-25 mg, about 0.1-1 mg, about 1-5 mg, about 5-10 mg, about 8-16 mg, about 10-15 mg, about 15-20 mg, or about 20-25 mg of TAK-733.

In some embodiments, the dosage of cetuximab is in the amount of about 0.1-20 mg/kg, about 0.1-0.5 mg/kg, about 0.5-1 mg/kg, about 1-2 mg/kg, about 2-3 mg/kg, about 3-5 mg/kg, about 5-7.5 mg/kg, about 7.5-10 mg/kg, about 10-15 mg/kg, about 15-20 mg/kg, or about 0.1-10 mg/kg. In some embodiments, the dosage of cetuximab is about 150-200 mg/m$^2$, about 200-250 mg/m$^2$, about 250-300 mg/m$^2$, about 300-400 mg/m$^2$, about 400-500 mg/m$^2$, about 500-750 mg/m$^2$, about 150-250 mg/m$^2$, about 250-400 mg/m$^2$, or about 400-750 mg/m$^2$. In some embodiments, cetuximab is infused over 30-180 minutes, about 30-60 minutes, about 60-120 minutes, or about 120-180 minutes. In some embodiments, the maximum infusion rate is about 5 mL/min or about 10 mL/min. In some embodiments, cetuximab is administered about every day, about every week, about every two weeks, about every three week, or about every four weeks. In some embodiments, the dosage of cetuximab is about 500 mg/m$^2$ infused over 60-120 minutes every two weeks. In some embodiments, cetuximab is administered in accordance with a schedule comprising an initial dose followed by several subsequent doses. In some embodiments, the initial dose is about 250-500 mg/m$^2$, about 250-300 mg/m$^2$, about 300-400 mg/m$^2$ or about 400-500 mg/m$^2$. In some embodiments, the initial dose is about 250 mg/m$^2$, about 400 mg/m$^2$ or about 500 mg/m$^2$. In some embodiments, the subsequent dose is about 50-300 mg/m$^2$, about 50-150 mg/m$^2$, about 150-200 mg/m$^2$ or about 200-300 mg/m$^2$. In some embodiments, the subsequent dose is about 50 mg/m$^2$, about 150 mg/m$^2$ or about 250 mg/m$^2$. In some embodiments, cetuximab is administered in 400 mg/m$^2$ infused over 120 minutes followed by 250 mg/m$^2$ weekly infused over 60 minutes. In some embodiments, cetuximab is administered in 400 mg/m$^2$ infused over 120 minutes followed by 150 mg/m$^2$ weekly infused over 60 minutes.

In some embodiments, the daily dosage of palbociclib or a salt thereof is in the amount of about 0.5-1 mg/kg, about 1.5-2 nag/kg, about 2-2.5 mg/kg, about 2.5-3 mg/kg, about 3-3.5 mg/kg, about 1-2.5 mg/kg, about 1-3 mg/kg, or about 3-5 mg/kg of palbociclib. In some embodiments, the daily dosage of palbociclib or a salt thereof is in the amount of about 50 mg, about 75 mg, about 100 mg, or about 125 mg of palbociclib. In some embodiments, the daily dosage of palbociclib or a salt thereof is in the amount of less than about 50 mg, about 75 mg, about 100 mg, or about 125 mg of palbociclib. In some embodiments, the daily dosage of palbociclib or a salt thereof is in the amount of about 25-225 mg, about 25-50 mg, about 50-75 mg, about 75-125 mg, about 125-150 mg about 150-200 mg, or about 200-225 mg of palbociclib. In some embodiments, the daily dosage of palbociclib or a salt thereof is in the amount of about 1.25-2.1 mg/kg of palbociclib. In some embodiments, the method comprises administration of cetuximab, TAK-733 or a solvate or a salt thereof, and palbociclib or a solvate or a salt thereof.

In another aspect, the method comprises administering an effective amount of osimertinib or a salt thereof, TAK-733 or a salt thereof, and palbociclib or a salt thereof. In some embodiments, the daily dosage of osimertinib or a salt thereof is in the amount of about 0.25-0.5 mg/kg, about 0.5-1 mg/kg, about 1-1.5 mg/kg, about 1.5-2 mg/kg, about 2-2.5 mg/kg, about 2.5-3 mg/kg, about 3-3.5 mg/kg, about 3.5-4 mg/kg, or about 0.5-3 mg/kg of osimertinib. In some embodiments, the daily dosage of osimertinib or a salt thereof is in the amount of about 20 mg, about 40 mg, about 80 mg, or about 160 mg of osimertinib. In some embodiments, the daily dosage of osimertinib or a salt thereof is in the amount of less than about 20 mg, about 40 mg, about 80 mg, or about 160 mg of osimertinib. In some embodiments, the dosage of osimertinib or a salt thereof is in the amount of about 20-240 mg, about 20-40 mg, about 40-80 mg, about 80-160 mg, about 160-240 mg or about 40-160 mg of osimertinib. In some embodiments, the daily dosage of osimertinib or a salt thereof is in the amount of about 0.6-2.7 mg/kg of osimertinib. In some embodiments, osimertinib is in its mesylate salt form.

In some embodiments, the daily dosage of TAK-733 or a salt thereof is in the amount of in the amount of about 0.001-1 mg/kg, about 0.001-0.002 mg/kg, about 0.002-0.005 mg/kg, about 0.005-0.01 mg/kg, about 0.01-0.05 mg/kg, about 0.05-0.1 mg/kg, about 0.1-0.2 mg/kg, about 0.2-0.3 mg/kg, about 0.3-0.4 mg/kg, about 0.4-0.5 mg/kg, about 0.5-0.6 mg/kg, about 0.6-0.7 mg/kg, about 0.7-0.8 mg/kg, about 0.8-0.9 mg/kg, or about 0.9-1 mg/kg of TAK-733. In some embodiments, the daily dosage of TAK-733 or a salt thereof is in the amount of about 10 mg, about 15 mg, about 20 mg, or about 25 mg of TAK-733. In some embodiments, the daily-dosage of TAK-733 or a salt thereof is in the amount of less than about 10 mg, about 15 mg, about 20 mg, or about 25 mg of TAK-733. In some embodiments, the daily dosage of TAK-733 or a salt thereof is in the amount of about 0.1-25 mg, about 0.1-1 mg, about 1-5 mg, about 5-10 mg, about 8-16 mg, about 10-15 mg, about 15-20 mg, or about 20-25 mg of TAK-733.

In some embodiments, the daily dosage of palbociclib or a salt thereof is in the amount of about 0.5-1 mg/kg, about 1.5-2 mg/kg, about 2-2.5 mg/kg, about 2.5-3 mg/kg, about 3-3.5 mg/kg, about 1-2.5 mg/kg, about 1-3 mg/kg, or about 3-5 mg/kg of palbociclib. In some embodiments, the daily dosage of palbociclib or a salt thereof is in the amount of about 50 mg, about 75 mg, about 100 mg, or about 125 mg of palbociclib. In some embodiments, the daily dosage of palbociclib or a salt thereof is in the amount of less than about 50 mg, about 75 mg, about 100 mg, or about 125 mg of palbociclib. In some embodiments, the daily dosage of palbociclib or a salt thereof is in the amount of about 25-225 mg, about 25-50 mg, about 50-75 mg, about 75-125 mg, about 125-150 mg about 150-200 mg, or about 200-225 mg of palbociclib. In some embodiments, the daily dosage of palbociclib or a salt thereof is in the amount of about 1.25-2.1 mg/kg of palbociclib. In some embodiments, the method comprises administration of osimertinib or a solvate or a salt thereof, TAK-733 or a solvate or a salt thereof, and palbociclib or a solvate or a salt thereof.

In another aspect, the method comprises administering an effective amount of cetuximab, trametinib or a salt thereof and palbociclib or a salt thereof. In some embodiments, the daily dosage of trametinib or a salt thereof is in the amount of in the amount of about 0.01-1 mg/kg, about 0.01-0.02 mg/kg, about 0.02-0.03 mg/kg, about 0.03-0.05 mg/kg, about 0.05-0.08 mg/kg, about 0.08-0.1 mg/kg, about 0.1-0.2 mg/kg, about 0.2-0.3 mg/kg, about 0.3-0.4 mg/kg, about 0.4-0.5 mg/kg, about 0.5-0.6 mg/kg, about 0.6-0.7 mg/kg, about 0.7-0.8 mg/kg, about 0.8-0.9 mg/kg, or about 0.9-1 mg/kg of trametinib. In some embodiments, the daily dosage of trametinib or a salt thereof is in the amount of about 0.5 mg, about 1 mg, about 2 mg, or about 4 mg of trametinib. In some embodiments, the daily dosage of trametinib or a salt thereof is in the amount of less than about 0.5 mg, about 1 mg, about 2 mg, or about 4 mg of trametinib. In some embodiments, the daily dosage of trametinib or a salt thereof is in the amount of about 0.1-25 mg, about 0.1-0.5 mg, about 0.5-1 mg, about 1-2 mg, about 2-4 mg, about 4-10 trig or about 0.5-2 mg of trametinib.

In some embodiments, the dosage of cetuximab is in the amount of about 0.1-20 mg/kg, about 0.1-0.5 mg/kg, about 0.5-1 mg/kg, about 1-2 mg/kg, about 2-3 mg/kg, about 3-5 mg/kg, about 5-7.5 mg/kg, about 7.5-10 mg/kg, about 10-15 mg/kg, about 15-20 mg/kg, or about 0.1-10 mg/kg. In some embodiments, the dosage of cetuximab is about 150-200 mg/m², about 200-250 mg/m², about 250-300 mg/m², about 300-400 mg/m², about 400-500 mg/m², about 500-750 mg/m², about 150-250 mg/m², about 250-400 mg/m², or about 400-750 mg/m². In some embodiments, cetuximab is infused over 30-180 minutes, about 30-60 minutes, about 60-120 minutes, or about 120-180 minutes. In some embodiments, the maximum infusion rate is about 5 mL/min or about 10 mL/rain. In some embodiments, cetuximab is administered about every day, about every week, about every two weeks, about every three week, or about every four weeks. In some embodiments, the dosage of cetuximab is about 500 mg/m² infused over 60-120 minutes every two weeks. In some embodiments, cetuximab is administered in accordance with a schedule comprising an initial dose followed by several subsequent doses. In some embodiments, the initial dose is about 250-500 mg/m², about 250-300 mg/m², about 300-400 mg/m² or about 400-500 mg/m². In some embodiments, the initial dose is about 250 mg/m², about 400 mg/m² or about 500 mg/m². In some embodiments, the subsequent dose is about 50-300 mg/m², about 50-150 mg/m², about 150-200 mg/m² or about 200-300 mg/m². In some embodiments, the subsequent dose is about 50 mg/m², about 150 mg/m² or about 250 mg/m². In some embodiments, cetuximab is administered in 400 mg/m² infused over 120 minutes followed by 250 mg/m² weekly infused over 60 minutes. In some embodiments, cetuximab is administered in 400 mg/m² infused over 120 minutes followed by 150 mg/m² weekly infused over 60 minutes.

In some embodiments, the daily dosage of palbociclib or a salt thereof is in the amount of about 0.5-1 mg/kg, about 1.52 mg/kg, about 2-2.5 mg/kg, about 2.5-3 mg/kg, about 3-3.5 mg/kg, about 1-2.5 mg/kg, about 1-3 mg/kg, or about 3-5 mg/kg of palbociclib. In some embodiments, the daily dosage of palbociclib or a salt thereof is in the amount of about 50 mg, about 75 mg, about 100 mg, or about 125 mg of palbociclib. In some embodiments, the daily dosage of palbociclib or a salt thereof is in the amount of less than about 50 mg, about 75 mg, about 100 mg, or about 125 mg of palbociclib. In some embodiments, the daily dosage of palbociclib or a salt thereof is in the amount of about 25-225 mg, about 25-50 mg, about 50-75 mg, about 75-12.5 mg, about 125-150 mg about 150-200 mg, or about 200-225 mg of palbociclib. In some embodiments, the daily dosage of palbociclib or a salt thereof is in the amount of about 1.25-2.1 mg/kg of palbociclib. In some embodiments, the method comprises administration of cetuximab, TAK-733 or a solvate or a salt thereof, and palbociclib or a solvate or a salt thereof.

In another aspect, the method comprises administering an effective amount of osimertinib or a salt thereof, trametinib or a salt thereof, and palbociclib or a salt thereof. In some embodiments, the daily dosage of osimertinib or a salt thereof is in the amount of about mg/kg, about 0.5-1 mg/kg, about 1-1.5 mg/kg, about 1.52 mg/kg, about 2-2.5 mg/kg, about 2.5-3 mg/kg, about 3-3.5 mg/kg, about 3.5-4 mg/kg, or about 0.5-3 mg/kg of osimertinib. In some embodiments, the daily dosage of osimertinib or a salt thereof is in the amount of about 2.0 mg, about 40 mg, about 80 mg, or about 160 mg of osimertinib. In some embodiments, the daily dosage of osimertinib or a salt thereof is in the amount of less than about 20 mg, about 40 mg, about 80 mg, or about 160 mg of osimertinib. In some embodiments, the dosage of osimertinib or a salt thereof is in the amount of about 20-240 mg, about 20-40 mg, about 40-80 mg, about 80-160 mg, about 160-240 mg or about 40-160 mg of osimertinib. In some embodiments, the daily dosage of osimertinib or a salt thereof is in the amount of about 0.6-2.7 mg/kg of osimertinib. In some embodiments, osimertinib is in its mesylate salt form.

In some embodiments, the daily dosage of trametinib or a salt thereof is in the amount of in the amount of about 0.01-1 mg/kg, about 0.01-0.02 mg/kg, about 0.02-0.03 mg/kg, about 0.03-0.05 mg/kg, about 0.05-0.08 mg/kg, about 0.08-0.1 mg/kg, about 0.1-0.2 mg/kg, about 0.2-0.3 mg/kg, about 0.3-0.4 mg/kg, about 0.4-0.5 mg/kg, about 0.5-0.6 mg/kg, about 0.6-0.7 mg/kg, about 0.7-0.8 mg/kg, about 0.8-0.9 mg/kg, or about 0.9-1 mg/kg of trametinib. In some embodiments, the daily dosage of trametinib or a salt thereof is in the amount of about 0.5 mg, about 1 mg, about 2 mg, or about 4 mg of trametinib. In some embodiments, the daily dosage of trametinib or a salt thereof is in the amount of less than about 0.5 mg, about 1 mg, about 2 mg, or about 4 mg of trametinib. In some embodiments, the daily dosage of trametinib or a salt thereof is in the amount of about 0.1-25 mg, about 0.1-0.5 mg, about 0.5-1 mg, about 1-2 mg, about 2-4 mg, about 4-10 mg or about 0.5-2 mg of trametinib.

In some embodiments, the daily dosage of palbociclib or a salt thereof is in the amount of about 0.5-1 mg/kg, about 1.5-2 mg/kg, about 2-2.5 mg/kg, about mg/kg, about 3-3.5 mg/kg, about 1-2.5 mg/kg, about 1-3 mg/kg, or about 3-5 mg/kg of palbociclib. In some embodiments, the daily dosage of palbociclib or a salt thereof is in the amount of about 50 mg, about 75 mg, about 100 mg, or about 125 mg of palbociclib. In some embodiments, the daily dosage of palbociclib or a salt thereof is in the amount of less than about 50 mg, about 75 mg, about 100 mg, or about 125 mg of palbociclib. In some embodiments, the daily dosage of palbociclib or a salt thereof is in the amount of about 25-225 mg, about 25-50 mg, about 50-75 mg, about 75-125 mg, about 125-150 mg about 150-200 mg, or about 200-225 mg of palbociclib. In some embodiments, the daily dosage of palbociclib or a salt thereof is in the amount of about 1.25-2.1 mg/kg of palbociclib. In some embodiments, the method comprises administration of osimertinib or a solvate or a salt thereof, trametinib or a solvate or a salt thereof, and palbociclib or a solvate or a salt thereof.

In another aspect, the method provides administering an effective amount of an EGFR inhibitor (e.g., osimertinib or cetuximab), a MEK 1/2 inhibitor (e.g., cobimetinib, trametinib or TAK-733) and a CDK 4/6 inhibitor (e.g., palbociclib) until disease progression or unacceptable toxicity. In some embodiments, the method provides administering an effective amount of an EGFR inhibitor (e.g., osimertinib or cetuximab), a MEK 1/2 inhibitor (e.g., cobimetinib, trametinib or TAK-733) and a CDK 4/6 inhibitor (e.g., palbociclib) for at least about 1-2 weeks, about 2-3 weeks, about 3-4 weeks, about 4-5 weeks, about 5-6 weeks, about 6-7 weeks, about 7-8 weeks, about 8-9 weeks, about 9-10 weeks, about 2-3 months, about 3-4 months, about 4-5 months, about 5-6 months, about 6-12 months, or about 12-24 months. In some embodiments, the effective amount of an EGER inhibitor (e.g., osimertinib or cetuximab), a MEK 1/2 inhibitor (e.g., cobimetinib, trametinib or TAK-733) and a CDK 4/6 inhibitor (e.g., palbociclib) is administered for 21 consecutive days followed by 7 days off to comprise a complete cycle of 28 days. In some embodiments, the subject is administered an effective amount of an EGFR inhibitor (e.g., osimertinib or cetuximab), a MEK 1/2 inhibitor (e.g., cobimetinib, trametinib or TAK-733) and a CDK 4/6 inhibitor (e.g., palbociclib) for one, two, three, four, five, six, seven, eight, nine, ten or more cycles of 28 days. In some embodiments, the EGFR inhibitor (e.g., osimertinib or cetuximab), the MEK 1/2 inhibitor (e.g., cobimetinib, trametinib or TAK-733) and the CDK 4/6 inhibitor (e.g., palbociclib) are administered for different durations.

In another aspect, the effective amount of an EGFR inhibitor (e.g., osimertinib or cetuximab), a MEK 1/2 inhibitor (e.g., cobimetinib, trametinib or TAK-733) and a CDK 4/6 inhibitor (e.g., palbociclib) are formulated as one composition. In another aspect, the effective amount of an EGFR inhibitor (e.g., osimertinib or cetuximab), a MEK 1/2 inhibitor (e.g., cobimetinib, trametinib or TAK-733) and a CDK 4/6 inhibitor (e.g., palbociclib) are formulated separately. In some embodiments, osimertinib or a salt thereof, cobimetinib or a salt thereof, and palbociclib or a salt thereof are formulated as one composition or separate compositions for oral administration. In some embodiments, osimertinib or a salt thereof, TAK-733 or a salt thereof, and palbociclib or a salt thereof are formulated as one composition or separate compositions for oral administration. In some embodiments, osimertinib or a salt thereof, trametinib or a salt thereof, and palbociclib or a salt thereof are formulated as one composition or separate compositions for oral administration. In some embodiments, cobimetinib or a salt thereof and palbociclib or a salt thereof are formulated as one composition or separate compositions for oral administration. In some embodiments, TAK-733 or a salt thereof and palbociclib or a salt thereof are formulated as one composition or separate compositions for oral administration. In some embodiments, trametinib or a salt thereof and palbociclib or a salt thereof are formulated as one composition or separate compositions for oral administration. For oral administration, the method may comprise formulating the compounds in a solid than, such as a tablet or capsule, or as a solution, emulsion, or suspension. To prepare the oral compositions, the compounds may be formulated to yield a daily dosage described herein. In some embodiments, cetuximab is formulated for intravenous infusion.

In some embodiments, the EGFR inhibitor (e.g., osimertinib or cetuximab), the MEK 1/2 inhibitor cobimetinib, trametinib or TAK-733) and the CDK 4/6 inhibitor (e.g., palbociclib) are formulated in the same form. In some embodiments, osimertinib or a salt thereof, cobimetinib or a salt thereof, and/or palbociclib or a salt thereof are formulated in a solid form, such as a tablet or capsule. In some embodiments, osimertinib or a salt thereof, TAK-733 or a salt thereof, and/or palbociclib or a salt thereof are formulated in a solid form, such as a tablet or capsule. In some embodiments, osimertinib or a salt thereof, trametinib or a salt thereof, and/or palbociclib or a salt thereof are formulated in a solid form, such as a tablet or capsule. In some embodiments, cetuximab, cobimetinib or a salt thereof, and/or palbociclib or a salt thereof are formulated in a liquid form, such as suspensions, solutions, emulsions, or syrups, or may be lyophilized. In some embodiments, cetuximab, TAK-733 or a salt thereof, and/or palbociclib or a salt thereof are formulated in a liquid form, such as suspensions, solutions, emulsions, or syrups, or may be lyophilized. In some embodiments, cetuximab, trametinib or a salt thereof, and/or palbociclib or a salt thereof are formulated in a liquid form, such as suspensions, solutions, emulsions, or syrups, or may be lyophilized.

In another aspect, the EGFR inhibitor (e.g., osimertinib or cetuximab), the MEK 1/2 inhibitor (e.g., cobimetinib, trametinib or TAK-733) and the CDK 4/6 inhibitor (e.g., palbociclib) are administered simultaneously or intermittently. In some embodiments, the EGFR inhibitor (e.g., osimertinib or cetuximab), the MEK 1/2 inhibitor (e.g., cobimetinib, trametinib or TAK-733) and the CDK 4/6 inhibitor (e.g., palbociclib) are formulated as one composition and administered as one composition. In some embodiments, the EGFR inhibitor (e.g., osimertinib or cetuximab), the MEK 1/2 inhibitor (e.g., cobimetinib, trametinib or TAK-733) and the CDK 4/6 inhibitor (e.g., palbociclib) are formulated separately and administered simultaneously. In some embodiments, the EGFR inhibitor (e.g., osimertinib or cetuximab), the MEK 1/2 inhibitor cobimetinib, trametinib or TAK-733) and the CDK 4/6 inhibitor (e.g., palbociclib) are formulated separately and administered intermittently. In some embodiments, the EGFR inhibitor (e.g., osimertinib or cetuximab), the MEK 1/2 inhibitor (e.g., cobimetinib, trametinib or TAK-733) and the CDK 4/6 inhibitor (e.g., palbociclib) are formulated separately and administered with different dosing frequencies.

In another aspect, the method comprises administering an effective amount of osimertinib or a salt thereof, cobimetinib or a salt thereof, and palbociclib or a salt thereof. In some embodiments, osimertinib or a salt thereof is administered before cobimetinib or a salt thereof and palbociclib or a salt thereof. In some embodiments, cobimetinib or a salt thereof is administered before osimertinib or a salt thereof and palbociclib or a salt thereof. In some embodiments, palbociclib or a salt thereof is administered before osimertinib or a salt thereof and cobimetinib or a salt thereof in some embodiments, osimertinib or a salt thereof and cobimetinib or a salt thereof are administered together in the same or separate compositions. In some embodiments, osimertinib or a salt thereof and palbociclib or a salt thereof are administered together in the same or separate compositions. In some embodiments, cobimetinib or a salt thereof and palbociclib or a salt thereof are administered together in the same or separate compositions.

In another aspect, the method comprises administering an effective amount of cetuximab, cobimetinib or a salt thereof, and palbociclib or a salt thereof. In some embodiments, cetuximab is administered before cobimetinib or a salt thereof and palbociclib or a salt thereof. In some embodiments, cobimetinib or a salt thereof is administered before cetuximab and palbociclib or a salt thereof in some embodiments, palbociclib or a salt thereof is administered before cetuximab and cobimetinib or a salt thereof. In some embodiments, cetuximab and cobimetinib or a salt thereof are administered together in the same or separate compositions. In some embodiments, cetuximab and palbociclib or a salt thereof are administered together in the same or separate compositions. In some embodiments, cobimetinib or a salt thereof and palbociclib or a salt thereof are administered together in the same or separate compositions. In some embodiments, cetuximab is administered in a separate composition from cobimetinib or a salt thereof, and palbociclib or a salt thereof. In some embodiments, cetuximab is administered every week or every two weeks, while cobimetinib or a salt thereof and palbociclib or a salt thereof are administered on a daily basis.

In another aspect, the method comprises administering an effective amount of cetuximab, TAK-733 or a salt thereof, and palbociclib or a salt thereof. In some embodiments, cetuximab is administered before TAK-733 or a salt thereof and palbociclib or a salt thereof. In some embodiments, TAK-733 or a salt thereof is administered before cetuximab and palbociclib or a salt thereof. In some embodiments, palbociclib or a salt thereof is administered before cetuximab and TAK-733 or a salt thereof. In some embodiments, cetuximab and TAK-733 or a salt thereof are administered together in the same or separate compositions. In some embodiments, cetuximab and palbociclib or a salt thereof are administered together in the same or separate compositions. In some embodiments, TAK-733 or a salt thereof and palbociclib or a salt thereof are administered together in the same or separate compositions. In some embodiments, cetuximab is administered in a separate composition from TAK-733 or a salt thereof and palbociclib or a salt thereof in some embodiments, cetuximab is administered every week or every two weeks, while TAK-733 or a salt thereof and palbociclib or a salt thereof are administered on a daily basis.

In another aspect, the method comprises administering an effective amount of osimertinib or a salt thereof, TAK-733 or a salt thereof, and palbociclib or a salt thereof. In some embodiments, osimertinib or a salt thereof is administered before TAK-733 or a salt thereof and palbociclib or a salt thereof. In some embodiments, TAK-733 or a salt thereof is administered before osimertinib or a salt thereof and palbociclib or a salt thereof. In some embodiments, palbociclib or a salt thereof is administered before osimertinib or a salt thereof and TAK-733 or a salt thereof. In some embodiments, osimertinib or a salt thereof and TAK-733 or a salt thereof are administered together in the same or separate compositions. In some embodiments, osimertinib or a salt thereof and palbociclib or a salt thereof are administered together in the same or separate compositions. In some embodiments, TAK-733 or a salt thereof and palbociclib or a salt thereof are administered together in the same or separate compositions.

In another aspect, the method comprises administering an effective amount of cetuximab, trametinib or a salt thereof, and palbociclib or a salt thereof. In some embodiments, cetuximab is administered before trametinib or a salt thereof and palbociclib or a salt thereof. In some embodiments, trametinib or a salt thereof is administered before cetuximab and palbociclib or a salt thereof. In some embodiments, palbociclib or a salt thereof is administered before cetuximab and trametinib or a salt thereof. In some embodiments, cetuximab and trametinib or a salt thereof are administered together in the same or separate compositions. In some embodiments, cetuximab and palbociclib or a salt thereof are administered together in the same or separate compositions. In some embodiments, trametinib or a salt thereof and palbociclib or a salt thereof are administered together in the same or separate compositions. In some embodiments, cetuximab is administered in a separate composition from trametinib or a salt thereof and palbociclib or a salt thereof. In some embodiments, cetuximab is administered every week or every two weeks, while trametinib or a salt thereof and palbociclib or a salt thereof are administered on a daily basis.

In another aspect, the method comprises administering an effective amount of osimertinib or a salt thereof, trametinib or a salt thereof, and palbociclib or a salt thereof. In some embodiments, osimertinib or a salt thereof is administered before trametinib or a salt thereof and palbociclib or a salt thereof. In some embodiments, trametinib or a salt thereof is administered before osimertinib or a salt thereof and palbociclib or a salt thereof. In some embodiments, palbociclib or a salt thereof is administered before osimertinib or a salt thereof and trametinib or a salt thereof. In some embodiments, osimertinib or a salt thereof and trametinib or a salt thereof are administered together in the same or separate compositions. In some embodiments, osimertinib or a salt thereof and palbociclib or a salt thereof are administered together in the same or separate compositions. In some embodiments, trametinib or a salt thereof and palbociclib or a salt thereof are administered together in the same or separate compositions.

In some embodiments, intermittent administrations are about 1-30 minutes apart, about 30-60 minutes apart, about 60-120 minutes apart, about 120-240 minutes apart, about 240-480 minutes apart, about 480-720 minutes apart, about 720-960 minutes apart or about 960-1440 minutes apart. In some embodiments, intermittent administrations are about 1-2 days apart, 2-3 days apart, 3-4 days apart, 4-5 days apart, 5-6 days apart, or 6-7 days apart.

In another aspect, the subject has been previously treated with a BRAF inhibitor. In another aspect, the subject has not been previously treated with a BRAF inhibitor. In another aspect, the subject has been previously treated with a combination of BRAF inhibitor and MEK inhibitor. In another aspect, the subject has not been previously treated with a combination of BRAF inhibitor and MEK inhibitor. In some embodiments, the subject has developed acquired or adaptive resistance to a BRAF inhibitor or a MEK inhibitor. In some embodiments, the subject has not developed acquired or adaptive resistance to a BRAF inhibitor or a MEK inhibitor. MEK inhibitors include, without limitation, a small molecule or antibody that specifically binds to a MEK 1/2 or a ligand thereof, such as t trametinib, selumetinib, TAK-733, CI-1040, PD0325901, MEK162, AZD8330, GDC-0623, refametinib, pimasertib, RO4987655, RO5126766, WX-554, HL-085 and cobimetinib. BRAF inhibitors include, without limitation, a small molecule or antibody that specifically binds to wild or mutated BRAF or a ligand thereof, such as vemurafenib and dabrafenib.

In another aspect, the method described herein reduces cancer cell growth and/or increase cancer cell-killing by at least about 5%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 2000% or more than administration of one or two of osimertinib or a salt thereof, cobimetinib or a salt thereof, and palbociclib or a salt thereof only. In another aspect, the method described herein reduces cancer cell growth and/or increase cancer cell-killing by at least about 5%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 2000% or more than administration of one or two of cetuximab, cobimetinib or a salt thereof, and palbociclib or a salt thereof only. In another aspect, the method described herein reduces cancer cell growth and/or increase cancer cell-killing by at least about 5%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 2000% or more than administration of one or two of cetuximab, TAK-733 and palbociclib or a salt thereof only. In another aspect, the method described herein reduces cancer cell growth and/or increase cancer cell-killing by at least about 5%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 2000% or more than administration of one or two of osimertinib or a salt thereof, TAK-733 and palbociclib or a salt thereof only. In another aspect, the method described herein reduces cancer cell growth and/or increase cancer cell-killing by at least about 5%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 2000% or more than administration of one or two of cetuximab, trametinib and palbociclib or a salt thereof only. In another aspect, the method described herein reduces cancer cell growth and/or increase cancer cell-killing by at least about 5%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 2000% or more than administration of one or two of osimertinib or a salt thereof, trametinib and palbociclib or a salt thereof only.

And the method described herein has demonstrated a synergistic effect upon treatment of cancer with a BRAF mutation. In some embodiments, the efficacy of the method described herein is at least about 5%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 2000% or more than the additive efficacy of the individual administration of osimertinib or a salt thereof, cobimetinib or a salt thereof, and palbociclib or a salt thereof. In some embodiments, the efficacy of the method described herein is at least about 5%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 2000% or more than the additive efficacy of the individual administration of cetuximab, cobimetinib or a salt thereof, and palbociclib or a salt thereof. In some embodiments, the efficacy of the method described herein is at least about 5%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 2000% or more than the additive efficacy of the individual administration of cetuximab, TAK-733 or a salt thereof and palbociclib or a salt thereof. In some embodiments, the efficacy of the method described herein is at least about 5%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 2000% or more than the additive efficacy of the individual administration of osimertinib or a salt thereof, TAK-733 or a salt thereof and palbociclib or a salt thereof. In some embodiments, the efficacy of the method described herein is at least about 5%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 2000% or more than the additive efficacy of the individual administration of cetuximab, trametinib or a salt thereof and palbociclib or a salt thereof. In some embodiments, the efficacy of the method described herein is at least about 5%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 2000% or more than the additive efficacy of the individual administration of osimertinib or a salt thereof, trametinib or a salt thereof and palbociclib or a salt thereof.

In another aspect, the method described herein reduces mean tumor volume, in some embodiments, the method described herein reduces mean tumor volume by about 20-95%. In some embodiments, the mean tumor volume is reduced by at least about 10%, 15%, 20%, 25%, 30%, 35%, 40%, 45%, 50%, 55%, 60%, 65%, 70%, 75%, 80%, 85%, 90%, 95% or 99%.

In another aspect, the method described herein causes body weight changes in the subject at less than about 25%, less than about 20%, less than about 15%, or less than about 5%. In some embodiments, the method does not cause body weight change.

In yet another aspect, the method described herein comprises administration of a loading dose of the combination of (a) an epidermal growth factor receptor (EGFR) inhibitor (e.g., osimertinib or cetuximab); (b) a mitogen-activated protein kinase (MEK) 1/2 inhibitor (e.g., cobimetinib, trametinib or TAK-733); and (c) a cyclin dependent kinase (CDK) 4/6 inhibitor (e.g., palbociclib) followed by multiple separate maintenance doses of the combination. In some embodiments, each loading dose of the three inhibitors is higher than each maintenance doses. In some embodiments, the method described herein provides lower dosages, safety and/or tolerability for long-term administrations and/or treatments.

III. Compositions

Also provided herein are compositions comprising (a) an epidermal growth factor receptor (EGFR) inhibitor (e.g., osimertinib or cetuximab); (b) a mitogen-activated protein kinase (MEK) 1/2 inhibitor (e.g., cobimetinib, trametinib or TAK-733); and (c) a cyclin dependent kinase (CDK) 4/6 inhibitor (e.g., palbociclib); wherein the composition does not comprises a BRAF inhibitor. In some embodiments the composition consists of (a) an epidermal growth factor receptor (EGFR) inhibitor (e.g., osimertinib or cetuximab); (h) a mitogen-activated protein kinase (MEK) 1/2 inhibitor (e.g., cobimetinib, trametinib or TAK-733); and (c) a cyclin dependent kinase (CDK) 4/6 inhibitor (e.g., palbociclib).

Also provided herein is a composition comprising osimertinib or a salt thereof, cobimetinib or a salt thereof, and palbociclib or a salt thereof. Also provided herein is a composition comprising osimertinib or a salt thereof, TAK-733 or a salt thereof and palbociclib or a salt thereof. Also provided herein is a composition comprising osimertinib or a salt thereof, trametinib or a salt thereof and palbociclib or a salt thereof. These compositions may be used for treating and delaying progression of cancer with a BRAF mutation in a method described herein. In some embodiments, the composition does not comprise a BRAF inhibitor.

In one aspect, the composition may further comprise a pharmaceutically acceptable carrier, excipient, binder, or diluent. A pharmaceutically-acceptable excipient is a substance that is non-toxic and otherwise biologically suitable for administration to a subject. Such excipients facilitate administration of the compounds described herein and are compatible with the active ingredient, Examples of pharmaceutically-acceptable excipients include stabilizers, lubricants, surfactants, diluents, anti-oxidants, binders, coloring agents, bulking agents, emulsifiers, or taste-modifying agents. In some embodiments, pharmaceutical compositions according to the embodiments are sterile compositions. Pharmaceutical compositions may be prepared using compounding techniques known or that become available to those skilled in the art. Sterile compositions are also contemplated by the embodiments, including compositions that are in accord with national and local regulations governing such compositions.

The pharmaceutical compositions and compounds described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions provided herein may be administered by a suitable route of delivery, such as oral, parenteral, rectal, nasal, or topical route, or by inhalation. In some embodiments, the compositions are formulated for intravenous or oral administration.

In another aspect, the composition is formulated for oral administration. For oral administration, composition may be formulated in a solid form, such as a tablet or capsule, or as a solution, emulsion, or suspension. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

In another aspect, the composition comprises osimertinib or a salt thereof, cobimetinib or a salt thereof, and palbociclib or a salt thereof. In some embodiments, the composition comprises osimertinib or a salt thereof at greater than about 20%, or greater than about 25%, or greater than about 30%, or greater than about 35%, or greater than about 40%, or greater than about 45%, or greater than about 50%, or greater than about 55%, or greater than about 60%, or greater than about 65%, or greater than about 70% by weight.

In some embodiments, the composition comprises cobimetinib or a salt thereof at greater than about 20%, or greater than about 25%, or greater than about 30%, or greater than about 35%, or greater than about 40%, or greater than about 45%, or greater than about 50% by weight.

In some embodiments, the composition comprises palbociclib or a salt thereof at greater than about 30%, or greater than about 35%, or greater than about 40%, or greater than about 45%, or greater than about 50%, or greater than about 55%, or greater than about 60%, or greater than about 65%, or greater than about 70%, or greater than about 75%, or greater than about 80%, or greater than about 85%, or greater than about 90% by weight.

In some embodiments, the ratios of osimertinib or a salt thereof, cobimetinib or a salt thereof, and palbociclib or a salt thereof by weight in the compositions are about 1:1:1, 2:1:1, 3:1:1, 4:1:1, 1:2:1, 1:1:2, 1:1:3, 1:1:4, 1:1:5, 1:1:6, 1:1:7, 1:1:8, 1:1:9, 1:1:10, 2:1:2, 2:1:3, 2:1:4, 2:1:5, 2:1:6, 2:1:7, 2:1:8, 2:1:9, 2:1:10, 3:1:1, 3:1:2, 3:1:3, 3:1:4, 3:1:5, 3:1:6, 3:1:7, 3:1:8, 3:1:9, or 3:1:10. In some embodiments, the ratio of osimertinib or a salt thereof, cobimetinib or a salt thereof, and palbociclib or a salt thereof by weight in the compositions is about 2:1:4. In some embodiments, the ratio of osimertinib or a salt thereof and cobimetinib or a salt thereof by weight is in the range of about 2:3 to 4:1. In some embodiments, the ratio of osimertinib or a salt thereof and palbociclib or a salt thereof by weight is in the range of about 40:125 to 80:75. In some embodiments, the ratio of cobimetinib or a salt thereof and palbociclib or a salt thereof by weight is in the range of about 20:125 to 60:75.

In another aspect, the composition comprises salts of osimertinib, cobimetinib, TAK-733, trametinib or palbociclib. In some embodiments, the salts are pharmaceutically acceptable salts. Non-limiting examples of pharmaceutically acceptable salts include, without limitation, sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, mesylates phenylpropionates, phenylbutyrates, citrates, lactates, γ-hydroxybutyrates, glycolates, tartrates, and mandelates. In some embodiments, the composition comprises mesylate salts of osimertinib, cobimetinib, and palbociclib. In some embodiments, the composition comprises fumarate salts of osimertinib, cobimetinib, and palbociclib. In another aspect, the composition comprises solvates of osimertinib, cobimetinib, TAK-722 or palbociclib.

In another aspect, the composition comprises osimertinib or a salt thereof, TAK-733 or a salt thereof, and palbociclib or a salt thereof. In some embodiments, the composition comprises osimertinib or a salt thereof at greater than about 20%, or greater than about 25%, or greater than about 30%, or greater than about 35%, or greater than about 40%, or greater than about 45%, or greater than about 50%, or greater than about 55%, or greater than about 60%, or greater than about 65%, or greater than about 70% by weight.

In some embodiments, the composition comprises TAK-733 or a salt thereof at greater than about 20%, or greater than about 25%, or greater than about 30%, or greater than about 35%, or greater than about 40%, or greater than about 45%, or greater than about 50% by weight.

In some embodiments, the composition comprises palbociclib or a salt thereof at greater than about 30%, or greater than about 35%, or greater than about 40%, or greater than about 45%, or greater than about 50%, or greater than about 55%, or greater than about 60%, or greater than about 65%, or greater than about 70%, or greater than about 75%, or greater than about 80%, or greater than about 85%, or greater than about 90% by weight.

In some embodiments, the ratios of osimertinib or a salt thereof, TAK-733 or a salt thereof and palbociclib or a salt thereof by weight in the compositions are about 1:1:1, 2:1:1, 3:1:1, 4:1:1, 1:2:1, 1:1:2, 1:1:3, 1:1:4, 1:1:5, 1:1:6, 1:1:7, 1:1:8, 1:1:9, 1:1:10, 2:1:2, 2:1:3, 2:1:4, 2:1:5, 2:1:6, 2:1:7, 2:1:8, 2:1:9, 2:1:10, 3:1:1, 3:1:2, 3:1:3, 3:1:4, 3:1:5, 3:1:6, 3:1:7, 3:1:8, 3:1:9, or 3:1:10. In some embodiments, the ratio of osimertinib or a salt thereof and TAK-733 or a salt thereof by weight in the compositions is in the range of about 5:2 to 10:1. In some embodiments, the ratio of osimertinib or a salt thereof and palbociclib or a salt thereof by weight in the compositions is in the range of about 40:125 to 80:75. In some embodiments, the ratio of TAK-733 or a salt thereof and palbociclib or a salt thereof by weight in the compositions is in the range of about 8:125 to 16:75.

In another aspect, the composition comprises osimertinib or a salt thereof, trametinib or a salt thereof, and palbociclib or a salt thereof. In some embodiments, the composition comprises osimertinib or a salt thereof at greater than about 20%, or greater than about 25%, or greater than about 30%, or greater than about 35%, or greater than about 40%, or greater than about 45%, or greater than about 50%, or greater than about 55%, or greater than about 60%, or greater than about 65%, or greater than about 70% by weight.

In some embodiments, the composition comprises trametinib or a salt thereof at greater than about 20%, or greater than about 25%, or greater than about 30%, or greater than about 35%, or greater than about 40%, or greater than about 45%, or greater than about 50% by weight.

In some embodiments, the composition comprises palbociclib or a salt thereof at greater than about 30%, or greater than about 35%, or greater than about 40%, or greater than about 45%, or greater than about 50%, or greater than about 55%, or greater than about 60%, or greater than about 65%, or greater than about 70%, or greater than about 75%, or greater than about 80%, or greater than about 85%, or greater than about 90% by weight.

In some embodiments, the ratios of osimertinib or a salt thereof, trametinib or a salt thereof and palbociclib or a salt thereof by weight in the compositions are about 15:1:10, 20:1:10, 25:1:10, 30:1:10, 35:1:10, 40:1:10, 50:1:10, 15:1:20, 20:1:20, 25:1:20, 30:1:20, 35:1:20, 40:1:20, 50:1:20, 15:1:30, 20:1:30, 25:1:30, 30:1:30, 35:1:30, 40:1:30, 50:1:30 or 40:1:50. In some embodiments, the ratio of osimertinib or a salt thereof, trametinib or a salt thereof and palbociclib or a salt thereof by weight in the compositions is about 15:1:12. In some embodiments, the ratio of osimertinib or a salt thereof and trametinib or a salt thereof by weight in the compositions is the range of about 20:1 to 160:1. In some embodiments, the ratio of osimertinib or a salt thereof and palbociclib or a salt thereof by weight in the compositions is the range of about 40: 125 Co 80:75. In some embodiments, the ratio of trametinib or a salt thereof and palbociclib or a salt thereof by weight in the compositions is the range of about 1:250 to 2:75.

IV. Kits

Also provided herein are kits comprising (a) an epidermal growth factor receptor (EGFR) inhibitor (e.g., osimertinib or cetuximab); (b) a mitogen-activated protein kinase (MEK) 1/2 inhibitor (e.g., TAK-733, trametinib or cobimetinib); and (c) a cyclin dependent kinase (CDK) 4/6 inhibitor (e.g., palbociclib); wherein the kit does not comprises a BRAF inhibitor. In some embodiments, the kit consists of (a) an epidermal growth factor receptor (EGFR) inhibitor (e.g., osimertinib or cetuximab); (b) a mitogen-activated protein kinase (MEK) 1/2 inhibitor (e.g., TAK-733, trametinib or cobimetinib); and (c) a cyclin dependent kinase (CDK) 4/6 inhibitor (e.g., palbociclib). The kits may be used for treating and delaying progression of cancer with a BRAF mutation in a method described herein. In some embodiments, the kit does not comprise a BRAF inhibitor. The kit may comprise any compositions described herein.

Also provided herein is a kit comprising osimertinib or a salt thereof, cobimetinib or a salt thereof, and palbociclib or a salt thereof. In some embodiments, the kit comprises a pharmaceutical composition comprising osimertinib or a salt thereof and a pharmaceutically acceptable carrier, excipient, binder, or diluent. In some embodiments, the kit comprises a pharmaceutical composition comprising cobimetinib or a salt thereof and a pharmaceutically acceptable carrier, excipient, binder, or diluent. In some embodiments, the kit comprises a pharmaceutical composition comprising palbociclib or a salt thereof and a pharmaceutically acceptable carrier, excipient, binder, or diluent.

In some embodiments, osimertinib or a salt thereof, cobimetinib or a salt thereof, and palbociclib or a salt thereof are formulated as one composition in the kit. In some embodiments, osimertinib or a salt thereof, cobimetinib or a salt thereof, and palbociclib or a salt thereof are formulated separately. In some embodiments, osimertinib or a salt thereof, cobimetinib or a salt thereof, and/or palbociclib or a salt thereof are formulated for oral administration. In some embodiments, osimertinib or a salt thereof, cobimetinib or a salt thereof, and palbociclib or a salt thereof are formulated in the same form, such as solid or liquid form. In some embodiments, osimertinib or a salt thereof, cobimetinib or a salt thereof, and/or palbociclib or a salt thereof are formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms.

In some embodiments, the ratios of osimertinib or a salt thereof, cobimetinib or a salt thereof, and palbociclib or a salt thereof by weight provided in the kits are about 1:1:1, 2:1:1, 3:1:1, 4:1:1:, 1:2:1, 1:1:2, 1:1:3, 1:1:4, 1:1:5, 1:1:6, 1:1:7, 1:1:8, 1:1:9, 1:1:10, 2:1:2, 2:1:3, 2:1:4, 2:1:5, 2:1:6, 2:1:7, 2:1:8, 2:1:9, 2:1:10, 3:1:1, 3:1:2, 3:1:3, 3:1:4, 3:1:5, 3:1:6, 3:1:7, 3:1:8, 3:1:9, or 3:1:10. In some embodiments, the ratio of osimertinib or a salt thereof, cobimetinib or a salt thereof, and palbociclib or a salt thereof by weight in the kits is about 2:1:4. In some embodiments, the ratio of osimertinib or a salt thereof and cobimetinib or a salt thereof by weight in the kits is in the range of about 2:3 to 4:1. In some embodiments, the ratio of osimertinib or a salt thereof and palbocicli or a salt thereof by weight in the kits is in the range of about 40:125 to 80:75. In some embodiments, the ratio of cobimetinib or a salt thereof and palbocicli or a salt thereof by weight in the kits is in the range of about 20:125 to 60:75.

Also provided herein is a kit comprising cetuximab, cobimetinib or a salt thereof, and palbociclib or a salt thereof in some embodiments, the kit comprises a pharmaceutical composition comprising cetuximab and a pharmaceutically acceptable carrier, excipient, binder, or diluent. In some embodiments, the kit comprises a pharmaceutical composition comprising cobimetinib or a salt thereof and a pharmaceutically acceptable carrier, excipient, binder, or diluent. In some embodiments, the kit comprises a pharmaceutical composition comprising palbociclib or a salt thereof and a pharmaceutically acceptable carrier, excipient, binder, or diluent.

In some embodiments, cetuximab, cobimetinib or a salt thereof, and palbociclib or a salt thereof are formulated as two or more compositions in the kit. In some embodiments, cetuximab cobimetinib or a salt thereof, and palbociclib or a salt thereof are formulated separately. In some embodiments, cobimetinib or a salt thereof, and/or palbociclib or a salt thereof are formulated for oral administration. In some embodiments, cobimetinib or a salt thereof, and palbociclib or a salt thereof are formulated in the same form, such as solid or liquid form. In some embodiments, cetuximab, cobimetinib or a salt thereof, and/or palbociclib or a salt thereof are formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. In some embodiments, cetuximab is formulated for administration via intravenous infusion. In some embodiments, cobimetinib or a salt thereof and palbociclib or a salt thereof are formulated as one composition for oral administration.

In some embodiments, the ratios of cetuximab, cobimetinib or a salt thereof, and palbociclib or a salt thereof by weight provided in the kits are about 1:1:1:, 2:1:1, 3:1:1, 4:1:1:, 1:2:1, 3:1:2, 3:1:3, 3:1:4, 3:1:5, 3:1:6, 3:1:7, 3:1:8, 3:1:9, 3:1:10, 4:1:2, 4:1:3, 4:1:4, 4:1:5, 4:1:6, 4:1:7, 4:1:8, 4:1:9, 4:1:10, 5:1:1, 5:1:2, 5:1:3, 5:1:4, 5:1:5, 5:1:6, 5:1:7, 5:1:8, 5:1:9, 5:1:10, 6:1:1, 6:1:2, 6:1:3, 6:1:4, 6:1:5, 6:1:6, 6:1:7, 6:1:8, 6:1:9, or 6:1:10. In some embodiments, the ratio of cetuximab, cobimetinib or a salt thereof, and palbociclib or a salt thereof by weight in the kits is about 20:3:6. In some embodiments, the ratio of cetuximab and cobimetinib or a salt thereof by weight in the kits is the range of about 85:60 to 85:2. In some embodiments, the ratio of cetuximab and palbociclib or a salt thereof by weight in the kits is the range of about 17:25 to 34:3. In some embodiments, the ratio of cobimetinib or a salt thereof and palbociclib or a salt thereof by weight in the kits is the range of about 20:125 to 60:75.

Also provided herein is a kit comprising cetuximab, TAK-733 or a salt thereof, and palbociclib or a salt thereof. In some embodiments, the kit comprises a pharmaceutical composition comprising cetuximab and a pharmaceutically acceptable carrier, excipient, binder, or diluent. In some embodiments, the kit comprises a pharmaceutical composition comprising TAK-733 or a salt thereof and a pharmaceutically acceptable carrier, excipient, binder, or diluent. In some embodiments, the kit comprises a pharmaceutical composition comprising palbociclib or a salt thereof and a pharmaceutically acceptable carrier, excipient, binder, or diluent.

In some embodiments, cetuximab, TAK-733 or a salt thereof, and palbociclib or a salt thereof are formulated as one composition in the kit. In some embodiments, cetuximab, TAK-733 or a salt thereof and palbociclib or a salt thereof are formulated as two or more compositions in the kit. In some embodiments, cetuximab, TAK-733 or a salt thereof and palbociclib or a salt thereof are formulated separately. In some embodiments, TAK-733 or a salt thereof and/or palbociclib or a salt thereof are formulated tor oral administration. In some embodiments, TAK-733 or a salt thereof and palbociclib or a salt thereof are formulated in the same form, such as solid or liquid form. In some embodiments, cetuximab, TAK-733 or a salt thereof and/or palbociclib or a salt thereof are formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. In some embodiments, cetuximab is formulated for administration via intravenous infusion. In some embodiments, TAK-733 or a salt thereof and palbociclib or a salt thereof are formulated as one composition for oral administration.

In some embodiments, the ratios of cetuximab, TAK-733 or a salt thereof and palbociclib or a salt thereof by weight provided in the kits are about 5:1:5:, 10:1:5, 15:1:5, 20:1:5:, 10:2:1, 10:1:2, 10:1:3, 10:1:4, 10:1:5, 10:1:6, 10:1:7, 10:1:8, 5:1:9, 10:1:10, 15:1:2, 15:1:3, 15:1:4, 15:1:5, 15:1:6, 15:1:7, 15:1:8, 15:1:9, 15:1:10, 20:1:1, 20:1:2, 20:1:3, 20:1:4, 20:1:5, 20:1:6, 20:1:7, 20:1:8, 20:1:9, or 20:1:10. In some embodiments, the ratio of cetuximab, TAK-733 or a salt thereof and palbociclib or a salt thereof by weight in the kits is about 20:1:6. In some embodiments, the ratio of cetuximab and TAK-733 or a salt thereof by weight in the kits is in the range of about 85:16 to 850:8. In some embodiments, the ratio of cetuximab and palbociclib or a salt thereof by weight in the kits is in the range of about 17:25 to 34:3. In some embodiments, the ratio of TAK-733 or a salt thereof and palbociclib or a salt thereof by weight in the kits is in the range of about 8:125 to 16:75.

Also provided herein is a kit comprising osimertinib or a salt thereof, TAK-733 or a salt thereof, and palbociclib or a salt thereof in some embodiments, the kit comprises a pharmaceutical composition comprising osimertinib or a salt thereof and a pharmaceutically acceptable carrier, excipient, binder, or diluent. In some embodiments, the kit comprises a pharmaceutical composition comprising TAK-733 or a salt thereof and a pharmaceutically acceptable carrier, excipient, binder, or diluent. In some embodiments, the kit comprises a pharmaceutical composition comprising palbociclib or a salt thereof and a pharmaceutically acceptable carrier, excipient, binder, or diluent.

In some embodiments, osimertinib or a salt thereof, TAK-733 or a salt thereof, and palbociclib or a salt thereof are formulated as one composition in the kit. In some embodiments, osimertinib or a salt thereof, TAK-733 or a salt thereof, and palbociclib or a salt thereof are formulated separately. In some embodiments, osimertinib or a salt thereof, TAK-733 or a salt thereof, and/or palbociclib or a salt thereof are formulated for oral administration. In some embodiments, osimertinib or a salt thereof, TAK-733 or a salt thereof, and palbociclib or a salt thereof are formulated in the same form, such as solid or liquid form. In some embodiments, osimertinib or a salt thereof, TAK-733 or a salt thereof, and/or palbociclib or a salt thereof are formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms.

In some embodiments, the ratios of osimertinib or a salt thereof, TAK-733 or a salt thereof, and palbociclib or a salt thereof by weight provided in the kits are about 1:1:1:, 2:1:1, 3:1:1, 4:1:1:, 1:2:1, 1:1:2, 1:1:3, 1:1:4, 1:1:5, 1:1:6, 1:1:7, 1:1:8, 1:1:9, 1:1:10, 2:1:2, 2:1:3, 2:1:4, 2:1:5, 2:1:6, 2:1:7, 2:1:8, 2:1:9, 2:1:10, 3:1:1, 3:1:2, 3:1:3, 3:1:4, 3:1:5, 3:1:6, 3:1:7, 3:1:8, 3:1:9, or 3:1:10. In some embodiments, the ratio of osimertinib or a salt thereof, TAK-733 or a salt thereof and palbociclib or a salt thereof by weight in the compositions is about 3:1:6. In some embodiments, the ratio of osimertinib or a salt thereof and TAK-733 or a salt thereof by weight in the kits is in the range of about 5:2 to 10:1. In some embodiments, the ratio of osimertinib or a salt thereof and palbociclib or a salt thereof by weight in the kits is in the range of about 40:125 to 80:75. In some embodiments, the ratio of TAK-733 or a salt thereof and palbociclib or a salt thereof by weight in the kits is in the range of about 8:125 to 16:75.

Also provided herein is a kit comprising cetuximab, trametinib or a salt thereof, and palbociclib or a salt thereof. In some embodiments, the kit comprises a pharmaceutical composition comprising cetuximab and a pharmaceutically acceptable carrier, excipient, binder, or diluent. In some embodiments, the kit comprises a pharmaceutical composition comprising trametinib or a salt thereof and a pharmaceutically acceptable carrier, excipient, binder, or diluent. In some embodiments, the kit comprises a pharmaceutical composition comprising palbociclib or a salt thereof and a pharmaceutically acceptable carrier, excipient, binder, or diluent.

In some embodiments, cetuximab, trametinib or a salt thereof, and palbociclib or a salt thereof are formulated as one composition in the kit. In some embodiments, cetuximab, trametinib or a salt thereof and palbociclib or a salt thereof are formulated as two or more compositions in the kit. In some embodiments, cetuximab, trametinib or a salt thereof and palbociclib or a salt thereof are formulated separately. In some embodiments, trametinib or a salt thereof and/or palbociclib or a salt thereof are formulated for oral administration. In some embodiments, trametinib or a salt thereof and palbociclib or a salt thereof are formulated in the same form, such as solid or liquid form. In some embodiments, cetuximab, trametinib or a salt thereof and/or palbociclib or a salt thereof are formulated as solutions, emulsions, suspensions, dispersions, or inclusion complexes such as cyclodextrins in suitable pharmaceutical solvents or earners, or as pills, tablets, lozenges, suppositories, sachets, dragees, granules, powders, powders for reconstitution, or capsules along with solid carriers according to conventional methods known in the art for preparation of various dosage forms. In some embodiments, cetuximab is formulated for administration via intravenous infusion. In some embodiments, trametinib or a salt thereof and palbociclib or a salt thereof are formulated as one composition for oral administration.

Also provided herein is a kit comprising osimertinib or a salt thereof, trametinib or a salt thereof, and palbociclib or a salt thereof. In some embodiments, the kit comprises a pharmaceutical composition comprising osimertinib or a salt thereof and a pharmaceutically acceptable carrier, excipient, binder, or diluent. In some embodiments, the kit comprises a pharmaceutical composition comprising trametinib or a salt thereof and a pharmaceutically acceptable carrier, excipient, binder, or diluent. In some embodiments, the kit comprises a pharmaceutical composition comprising palbociclib or a salt thereof and a pharmaceutically acceptable carrier, excipient, binder, or diluent.

In some embodiments, osimertinib or a salt thereof, trametinib or a salt thereof, and palbociclib or a salt thereof are formulated as one composition in the kit. In some embodiments, osimertinib or a salt thereof, trametinib or a salt thereof, and palbociclib or a salt thereof are formulated separately. In some embodiments, osimertinib or a salt thereof, trametinib or a salt thereof, and/or palbociclib or a salt thereof are formulated for oral administration. In some embodiments, osimertinib or a salt thereof, trametinib or a salt thereof, and palbociclib or a salt thereof are formulated in the same form, such as solid or liquid form. In some embodiments, osimertinib or a salt thereof, trametinib or a salt thereof, and/or palbociclib or a salt thereof are formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms.

In some embodiments, the ratios of osimertinib or a salt thereof, trametinib or a salt thereof, and palbociclib or a salt thereof by weight provided in the kits are about 15:1:10, 20:1:10, 25:1:10, 30:1:10, 35:1:10, 40:1:10, 50:1:10, 15:1:20, 20:1:20, 25:1:20, 30:1:20, 35:1:20, 40:1:20, 50:1:20, 15:1:30, 20:1:30, 25:1:30, 30:1:30, 35:1:30, 40:1:30, 50:1:30 or 40:1:50. In some embodiments, the ratio of osimertinib or a salt thereof, trametinib or a salt thereof, and palbociclib or a salt thereof by weight in the compositions is about 15:1:12. In some embodiments, the ratio of osimertinib or a salt thereof and trametinib or a salt thereof by weight in the kits is the range of about 20:1 to 160:1. In some embodiments, the ratio of osimertinib or a salt thereof and palbociclib or a salt thereof by weight in the kits is the range of about 40:125 to 80:75. In some embodiments, the ratio of trametinib or a salt thereof and palbociclib or a salt thereof by weight in the kits is the range of about 1:250 to 2:75.

In another aspect, the kit further comprises a package insert including, without limitation, appropriate instructions for preparation and administration of the formulation, side effects of the formulation, and any other relevant information. The instructions may be in any suitable format, including, but not limited to, printed matter, videotape, computer readable disk, optical disc or directions to internet-based instructions.

In another aspect, kits for treating an individual who suffers from or is susceptible to the conditions described herein are provided, comprising a first container comprising a dosage amount of a composition or formulation as disclosed herein, and a package insert for use. The container may be any of those known in the art and appropriate for storage and delivery of intravenous formulation. In certain embodiments, the kit further comprises a second container comprising a pharmaceutically acceptable carrier, diluent, adjuvant, etc. for preparation of the formulation to be administered to the individual.

In another aspect, kits may also be provided that contain sufficient dosages of the compositions described herein (including pharmaceutical compositions thereof) to provide effective treatment for an individual for an extended period, such as days, 1-5 days, a week, 2 weeks, 3, weeks, 4 weeks, 6 weeks, 8 weeks, 1 cycle, 2 cycles, 3 cycles, 4 cycles, 5 cycles, 6 cycles, 7 cycles, 8 cycles or more.

In some embodiments, the kits may also include multiple doses and may be packaged in quantities sufficient for storage and use in pharmacies, for example, hospital pharmacies and compounding pharmacies. In certain embodiments the kits may include a dosage amount of at least one composition as disclosed herein.

EXAMPLES

The following examples are offered to illustrate but not to limit the invention. One of skill in the art will recognize that the following procedures may be modified using methods known to one of ordinary skill in the art.

Example 1 Ex Vivo Drug Tests Using Conditional Reprogramming Cell Pools

Surgical specimen from colorectal cancer patients were obtained from a hospital in Beijing after receiving patient consensus. Patient-derived xenograft tumor specimens were obtained from Nod/SCID mice inoculated with surgical tumor specimen from patients.

For ex vivo drug sensitivity assays, the colorectal tumor cells (CRC) were isolated from the patient tissue sample or PDX xenograft tumor tissue. Briefly, the tumor tissues were cut into small pieces less than 1 mm in diameter using scissors. The tumor fragments were transferred into a sterile 100-ml triangle glass flask loaded with a magnet stir bar. A 10-15 ml digestion media containing 0.25 U/ml Liberase DM was added into the minced tumor tissues to start enzyme digestion. The enzyme mixture was incubated at 37° C. for 1-2 hours with moderate stirring. The digested tumor tissue was filtered through a 100-μm cell retainer. The filtrates were re-filtered through a 40-μm cell restrainer. The CRC clusters retained on the 40-μm cell restrainer was collected, wash twice with HBSS, then re-suspended in a defined growth media supplemented with several stem cell growth factors.

The CRC clusters retained on the 40-μm cell restrainer were collected, wash twice with HBSS, then re-suspended in a defined growth media supplemented with cell growth factors and small molecule inhibitors. The CRC clusters were recovered in a defined growth medium overnight. The defined growth medium was StemPro® hESC SFM (defined, serum- and feeder-free medium (SFM)) supplemented with: Nicotinamide, Wnt3A, Noggin (Bone Morphogenetic Protein (BMP) inhibitor), Rspondin-1 (Wnt/β-catenin signaling agonist), and Y27632 (Rho-associated, coiled-coil containing protein kinase (ROCK-1) inhibitor).

For conditional reprogramming, the recovered cancer tissue-originated spheroids (CTOSs) were dissociated into single cells and seeded in a feeder cell/Rock inhibitor (Y27632) co-culture system at about 3000 cells per well in cell culture plate, and grow at 37 C for 3 days.

For ex vivo drug testing, the seeded CRCs were exposed to a combination of osimertinib (mesylate salt), cobimetinib (fumarate salt) and palbociclib (fumarate salt) for 72 hours. The combination was prepared in DMSO with a final DMSO concentration of 0.1% in media. Typical compound concentrations used for ex vivo drug testing are: 0.1-0.5 μM for osimertinib, 0.025-0.2 μM for cobimetinib, and 0.125-1 μM for palbociclib.

Following exposure with drug, the CRCs were labeled with 5-ethynyl-2'-deoxyuridine (Edu) to assess the tumor cell proliferation rates. The labeling lasted 24 hours in the presence of drug exposure. In the control group, epithelial tumor cells received no drug exposure with media change, but were similarly labeled with Edu. The labeled CRCs were fixed and stained with Hoechst 33342 in blocking buffer containing 0.5% Triton X-100 and 3% BSA overnight at 4° C. The tumor cells were incubated with EpCAM antibody (1:4000) for 2 hours at room temperature and rinsed with PBST. Subsequently, the CRCs were incubated with Alexa Fluor® 647 conjugated goat-antimouse secondary antibody for 30 minutes at room temperature and rinsed with PBST.

The incorporated Edu was detected by Click-iT reaction where fixed cells were incubated with a reaction mixture containing 1×Click-iT Edu reaction buffer, $CuSO_4$, and azide-conjugated Alexa Fluor dye in the dark. The stained cells were washed with PBS two times before image acquisition and analysis.

For image acquisition and analysis, the stained tumor cells were imaged by a high-content screening (HCS) platform (Thermo Scientific CellomicsArrayScanXTi HCS reader). The 10× objective was used to collect images. Twenty-five fields were imaged for each well for the analysis. From the images three fluorescent signals were obtained from the HCS reader. Blue fluorescent signals recorded nucleus signals stained with Hoechst 33342, green fluorescent signal detected the Edu incorporated in newly synthesized DNA, and red fluorescent signal detected the EpCAM positive epithelial cells population. A representative image is shown in FIG. 1.

The MI (Maximum Inhibition Index) was calculated using the EpCAM and Edu positive readout (Table 1). MI=Edu positive cells in control/Edu positive cells in treatment. As shown in Table 1, the combination therapy has the best specificity toward CRCs with a BRAF V600E or D581V mutation.

TABLE 1

Maximum Inhibition Index (MI) for
CRCs Treated with the Combination Therapy

| CRC Patient ID | KRAS Mutation | BRAF Mutation | NRAS Mutation | MI |
|---|---|---|---|---|
| CKY041 | G12D | | | 25 |
| NYL170 | G12D | | | 39 |
| NYL-JN-025 | G12D | | | 106 |
| ZKB171 | G12D | | | 908 |
| CKY048 | G13D | | | 3898.57 |
| NYL170(NYP023) | G12D | | | 39 |
| NYL102 | | | | 309 |
| NYL109 | | | | 1085 |
| NYL161 | | | | 175 |
| NYL-GZ-076 | | | | 73.67 |
| NYL-HEB-057 | | | G12D | 894.06 |
| NYP066 | | | | 20.87 |
| NYP069 | | | | 137.86 |
| NYL132 | | V600E | | 17882 |
| ZKB197 | | V600E | | 10448 |
| ZKB040 | | D581V | | 11311 |
| NYL243 | | V600E | | 89 |

Table 2 shows selectivity of the combination therapy toward CRCs with or without BRAF mutations. Selectivity=Number of CRC with MI>=1000/Total number of CRC*100%

TABLE 2

Selectivity of Combination Therapy toward BRAF Mutations in CRC

| | Number of CRC with MI >= 1000 | Number of CRC with MI < 1000 | Selectivity (%) |
|---|---|---|---|
| CRC with BRAF mutations | 3 | 1 | 75% |
| CRC with KRAS mutations | 1 | 6 | 14% |
| CRC without mutations | 1 | 5 | 17% |

The data presented in Table 2 demonstrates that colorectal cancer cells with BRAF mutations are extremely sensitive to the drug combination, with 3 out of 4 cases having greater than 10,000-fold reduction in cell proliferation compared with no drug control. In contrast, 2 out of 11 cases of colorectal cancer cells with no BRAF mutations, or mutations in KRAS/NRAS have greater than 1,000-fold reduction in cell proliferation, and none has greater than 10,000-fold reduction.

Example 2 Test of Tumor Volume Reduction in Mice During Combination Therapy in a PDX Model with Patient NYL132

Figure 2:
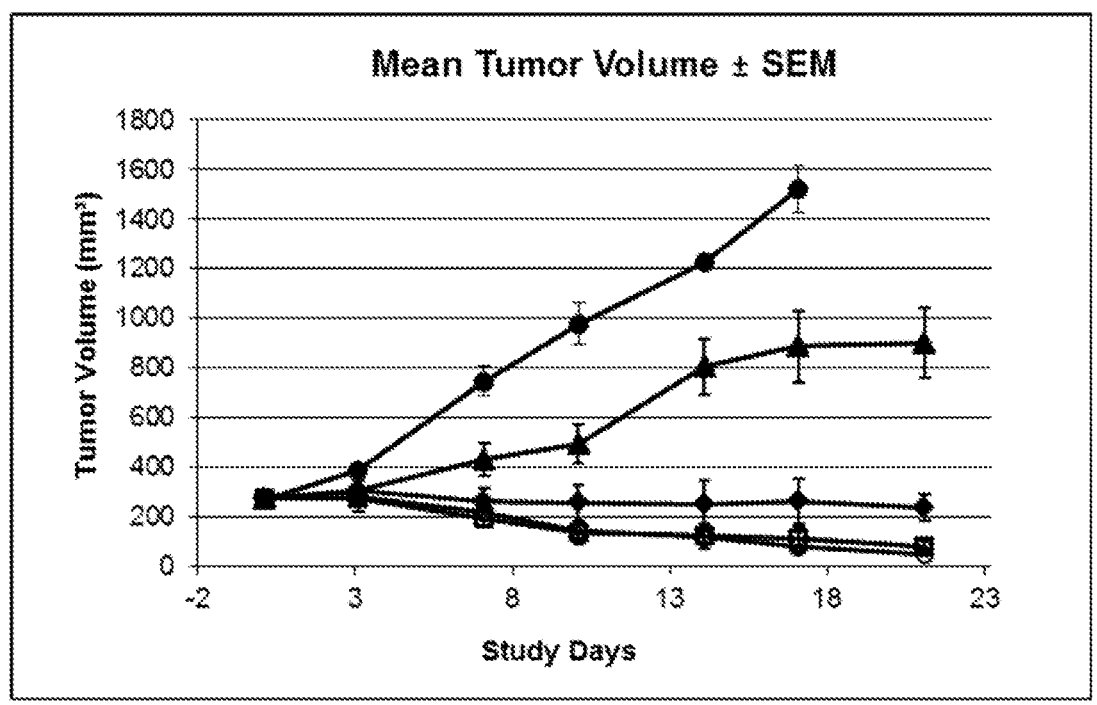
FIG. 2 depicts CRC (NYL132) volume reduction upon treatment with osimertinib, cobimetinib, and palbociclib. The graph shows the mean tumor volume change over time during the combination treatment: (solid circle)—control with no treatment; (solid triangle)—oxaliplatin 10 mg/kg and capecitabine 200 mg/kg daily (p.o.) for 3 weeks; (solid diamond)—osimertinib 5 mg/kg, cobimetinib 2.5 mg/kg, and palbociclib 10 mg/kg daily (p.o.) for 3 weeks; (open square)—osimertinib 7.5 mg/kg, cobimetinib 3.75 mg/kg, and palbociclib 15 mg/kg daily (p.o.) for 3 weeks; and (open circle)—osimertinib 10 mg/kg, cobimetinib 5 mg/kg, and palbociclib 20 mg/kg daily (p.o.) for 3 weeks. The dosage unit, mg/kg, refers to dose of the compound per kg of the mouse body weight.
Figure 3:
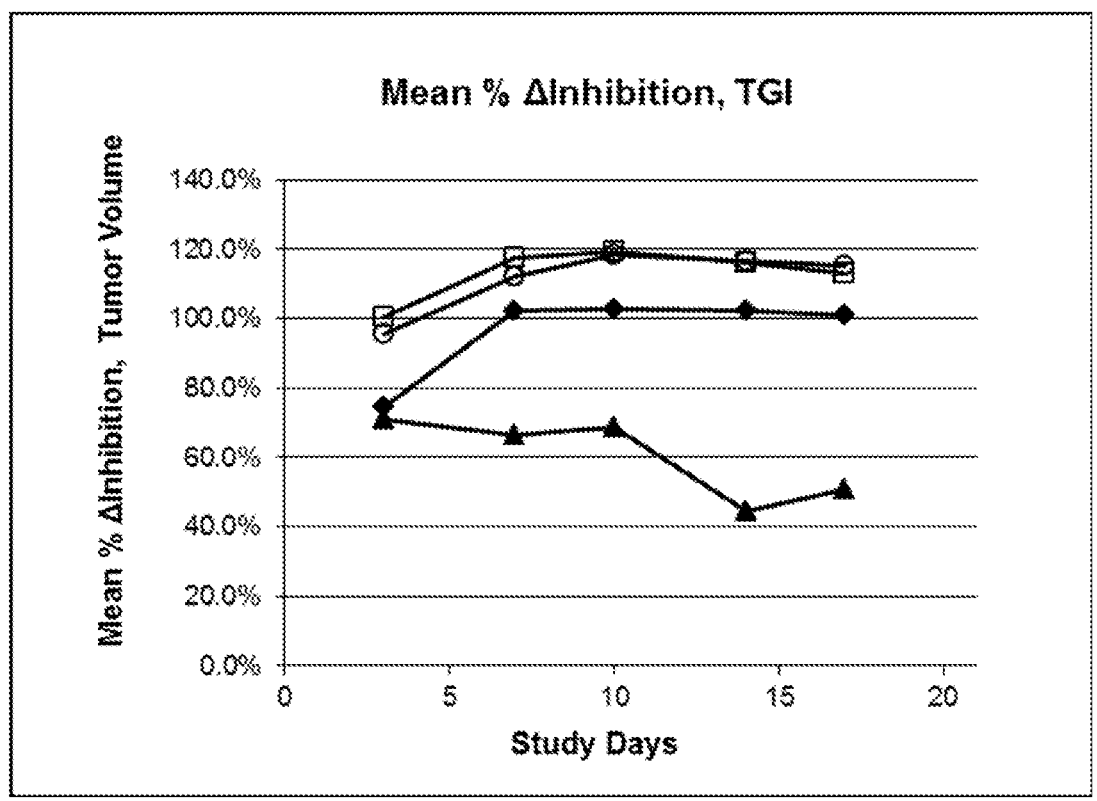
FIG. 3 depicts CRC (NYL132) volume reduction upon treatment with osimertinib, cobimetinib, and palbociclib. The graph shows tumor growth inhibition (TGI) over time during the combination treatment; (solid triangle)—oxaliplatin 10 mg/kg and capecitabine 200 mg/kg daily (p.o.) for 3 weeks; (solid diamond)—osimertinib 5 mg/kg, cobimetinib 2.5 mg/kg, and palbociclib 10 mg/kg daily (p.o.) for 3 weeks; (open square)—osimertinib 7.5 mg/kg, cobimetinib 3.75 mg/kg, and palbociclib 15 mg/kg daily (p.o.) for 3 weeks; and (open circle)—osimertinib 10 mg/kg, cobimetinib 5 mg/kg, and palbociclib 20 mg/kg daily (p.o.) for 3 weeks. The dosage unit, mg/kg, refers to dose of the compound per kg of the mouse body weight. TGI=(1−(Ti−T0)/(Vi−V0))*100%.

The study was conducted in xenograft tumor PDX model established with surgical tumor tissues from $BRAF^{V600E}$-CRC patient NYL132. Mean tumor volumes during the combination therapy are shown in Table 3 and FIG. 2. Briefly, 6-8 week-old female NOD/SCID mice were used for the studies. Tumor samples obtained from patients Tumor samples obtained from patients were immediately transferred into tissue preservation solution and sliced into small fragments. Mice were inoculated with the fragments subcutaneously at one flank to produce xenografts called passage 1 (P1). The serial xenografts of different passages were generated using the same procedure. When the average tumor size reached approximately 250-300 mm in the mice, the animals were randomly allocated into different groups, with 5 mice per group. The day of randomization was defined as study day 0. Tumor volume is expressed in $mm^3$ using the following formula: V (volume)=$(a \times b^2)/2$ where a and b are the long and short diameters of the tumor, respectively. Tumor suppression was expressed as Tumor growth inhibition (TGI), which is calculated according to the formula: TGI=(1−(Ti−T0)/(Vi−V0))*100%, where Ti is the mean tumor volume of the treatment group on the measurement day; T0 is the mean tumor volume of the treatment group at D0; Vi is the mean tumor volume of control group at the measurement day; V0 is the tumor volume of the control group at D0. TGI values for the combination therapy are shown in Table 4 and FIG. 3.

TABLE 3

Mean Tumor Volumes during Combination Therapy

| Samples | Dates/Study Days | | | |
|---|---|---|---|---|
| | 0 | 3 | 7 | 10 |
| Control | 271.30 ± 23.8 | 388.37 ± 17.19 | 746.39 ± 61.24 | 978.00 ± 83.56 |
| Oxaliplatin 10 mk/kg + capecitabine 200 mg/kg | 272.94 ± 26.3 | 306.87 ± 49.03 | 433.51 ± 65.12 | 494.07 ± 80.28 |
| Osimertinib 10 mg/kg + cobimetinib 5 mg/kg + palbociciib 20 mg/kg | 273.63 ± 20.51 | 279.06 ± 22.10 | 216.45 ± 9.17 | 143.50 ± 13.15 |
| Osimertinib 7.5 mg/kg + cobimetinib 3 75 mg/kg + palbociclib 15 mg/kg | 274.42 ± 20.33 | 274.06 ± 50.23 | 191.32 ± 28.45 | 139.03 ± 47.65 |
| Osimertinib 5 mg/kg + cobimetinib 2.5 mg/kg + palbociclib 10 mg/kg | 273.98 ± 9.17 | 304.06 ± 44.00 | 263.00 ± 54.48 | 256.45 ± 73.09 |

| Samples | Dates/Study Days | | |
|---|---|---|---|
| | 14 | 17 | 21 |
| Control | 1224.16 ± 31.18 | 1520.60 ± 93.96 | — |
| Oxaliplatin 10 mk/kg + capecitabine 200 mg/kg | 804.00 ± 112.61 | 886.58 ± 142.38 | 902.74 ± 141.36 |
| Osimertinib 10 mg/kg + cobimetinib 5 mg/kg + palbociciib 20 mg/kg | 115.25 ± 25.19 | 82.86 ± 23.39 | 49.09 ± 12.74 |

TABLE 3-continued

Mean Tumor Volumes during Combination Therapy

| | | | |
|---|---|---|---|
| Osimertinib 7.5 mg/kg + cobimetinib 3 75 mg/kg + palbociclib 15 mg/kg | 122.80 ± 49.44 | 112.69 ± 48.56 | 81.83 ± 18.85 |
| Osimertinib 5 mg/kg + cobimetinib 2.5 mg/kg + palbociclib 10 mg/kg | 252.63 ± 91.72 | 262.55 ± 93.40 | 235.79 ± 54.72 |

TABLE 4

Tumor growth inhibition during Combination Therapy

| | Dates/Study Days | | | | |
|---|---|---|---|---|---|
| Samples | 3 | 7 | 10 | 14 | 17 |
| Oxaliplatin 10 mk/kg + capecitabine 200 mg/kg | 71.02% | 66.20% | 68.71% | 44.27% | 50.88% |
| Osimertinib 10 mg/kg + cobimetinib 5 mg/kg + palbociclib 20 mg/kg | 95.36% | 112.03% | 118.41% | 116.62% | 115.27% |
| Osimertinib 7.5 mg/kg + cobimetinib 3.75 mg/kg + palbociclib 15 mg/kg | 100.31% | 117.49% | 119.16% | 115.91% | 112.95% |
| Osimertinib 5 mg/kg + cobimetinib 2.5 mg/kg + palbociclib 10 mg/kg | 74.31% | 102.31% | 102.48% | 102.24% | 100.91% |

The data presented in Table 3 and Table 4 shows that the combination therapy reduces the tumor volume in a dose-dependent manner. The data indicates the critical value of the combination therapy, demonstrating the ability to regress an established tumor (not just to slow the tumor growth rate), whereas the standard chemotherapy regimen for colorectal cancer was completely inactive in the BRAF mutant colorectal tumor model.

Example 3 Body Weight in Mice During Combination Therapy in a PDX Model with Patient NYL132

Figure 4:
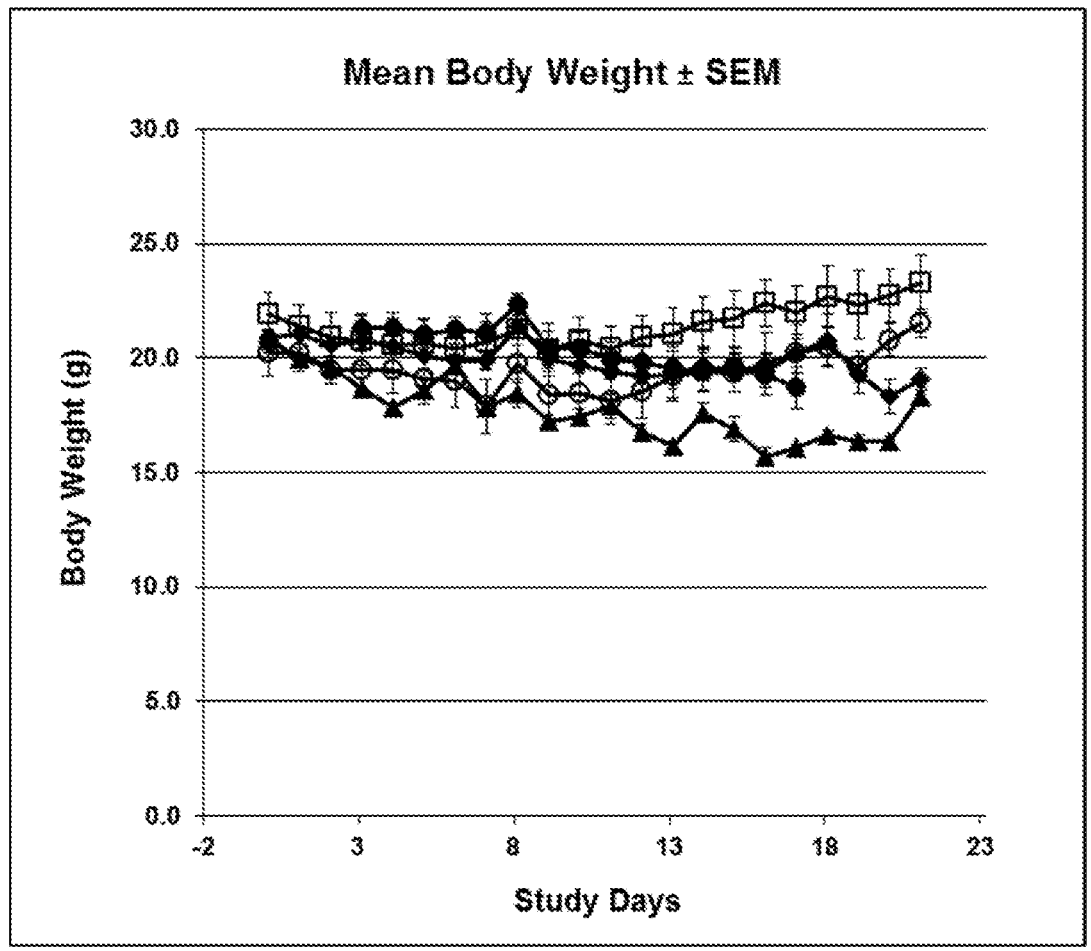
FIG. 4 depicts body weights of the mice (NYL132) during combination therapy: (solid circle)—control with no treatment; (solid triangle)—oxaliplatin 10 mg/kg and capecitabine 200 mg/kg daily (p.o.) for 3 weeks; (solid diamond)—osimertinib 5 mg/kg, cobimetinib 2.5 mg/kg, and palbociclib 10 mg/kg daily (p.o.) for 3 weeks; (open square)—osimertinib 7.5 mg/kg, cobimetinib 3.75 mg/kg, and palbociclib 15 mg/kg daily (p.o.) for 3 weeks; and (open circle)—osimertinib 10 mg/kg, cobimetinib 5 mg/kg, and palbociclib 20 mg/kg daily (p.o.) for 3 weeks.

The same procedure was followed as in Example 2 with $BRAF^{V600E}$-CRC patient NYL132. Mean body weights of mice are shown in Table 5 and FIG. 4.

TABLE 5

Body Weight of Mice during Combination Therapy

| Days | Control | Oxaliplatin 10 mk/kg + capecitabine 200 mg/kg | Osimertinib 10 mg/kg + cobimetinib 5 mg/kg + palbociclib 20 mg/kg | Osimertinib 7.5 mg/kg + cobimetinib 3.75 mg/kg + palbociclib 15 mg/kg | Osimertinib 5 mg/kg + cobimetinib 2.5 mg/kg + palbociclib 10 mg/kg |
|---|---|---|---|---|---|
| 0 | 20.7 ± 0.5 | 20.8 ± 0.4 | 20.2 ± 1.0 | 21.9 ± 1.0 | 20.9 ± 0.2 |
| 1 | | 19.9 ± 0.2 | 20.2 ± 0.8 | 21.4 ± 0.9 | 21.1 ± 1.0 |
| 2 | | 19.6 ± 0.2 | 19.5 ± 0.6 | 20.9 ± 1.1 | 20.6 ± 0.2 |
| 3 | 21.3 ± 0.5 | 18.6 ± 0.1 | 19.5 ± 0.9 | 20.8 ± 1.1 | 20.7 ± 0.3 |
| 4 | 21.3 ± 10.7 | 17.9 ± 0.1 | 19.5 ± 1.0 | 20.5 ± 1.2 | 20.5 ± 0.2 |
| 5 | 21.1 ± 0.7 | 18.6 ± 0.2 | 19.1 ± 1.1 | 20.6 ± 1.0 | 20.1 ± 0.2 |
| 6 | 21.2 ± 0.6 | 19.7 ± 0.3 | 19.0 ± 1.2 | 20.4 ± 1.1 | 19.9 ± 0.2 |
| 7 | 21.1 ± 0.5 | 17.8 ± 0.1 | 17.9 ± 1.2 | 20.7 ± 1.2 | 19.9 ± 0.4 |
| 8 | 22.3 ± 0.5 | 18.5 ± 0.6 | 19.7 ± 0.8 | 21.3 ± 1.2 | 21.4 ± 0.4 |
| 9 | 20.4 ± 0.7 | 17.2 ± 0.3 | 18.4 ± 1.0 | 20.4 ± 1.2 | 19.9 ± 0.4 |
| 10 | 20.4 ± 0.7 | 17.5 ± 0.3 | 18.4 ± 1.1 | 20.8 ± 1.0 | 19.7 ± 0.3 |
| 11 | 19.9 ± 0.8 | 17.9 ± 0.5 | 18.1 ± 1.0 | 20.4 ± 1.0 | 19.4 ± 0.4 |
| 12 | 19.8 ± 0.9 | 16.7 ± 0.4 | 18.5 ± 1.2 | 20.9 ± 0.9 | 19.2 ± 0.6 |
| 13 | 19.6 ± 0.9 | 16.2 ± 0.2 | 19.2 ± 1.1 | 21.1 ± 1.1 | 19.3 ± 1.0 |
| 14 | 19.4 ± 0.8 | 17.6 ± 0.4 | 19.4 ± 0.9 | 21.6 ± 1.1 | 19.7 ± 0.7 |
| 15 | 19.7 ± 0.7 | 16.9 ± 0.5 | 19.3 ± 0.8 | 21.7 ± 1.2 | 19.4 ± 0.9 |
| 16 | 19.3 ± 0.9 | 15.7 ± 0.4 | 19.4 ± 0.7 | 22.4 ± 1.0 | 19.8 ± 1.3 |
| 17 | 18.7 ± 0.9 | 16.1 ± 0.2 | 20.2 ± 0.9 | 22.0 ± 1.2 | 20.2 ± 1.2 |

TABLE 5-continued

Body Weight of Mice during Combination Therapy

| Days | Control | Oxaliplatin 10 mk/kg + capecitabine 200 mg/kg | Osimertinib 10 mg/kg + cobimetinib 5 mg/kg + palbociclib 20 mg/kg | Osimertinib 7.5 mg/kg + cobimetinib 3.75 mg/kg + palbociclib 15 mg/kg | Osimertinib 5 mg/kg + cobimetinib 2.5 mg/kg + palbociclib 10 mg/kg |
|---|---|---|---|---|---|
| 18 | | 16.6 ± 0.3 | 20.5 ± 0.8 | 22.7 ± 1.3 | 20.8 ± 1.1 |
| 19 | | 16.4 ± 0.3 | 19.6 ± 0.7 | 22.3 ± 1.5 | 19.3 ± 0.8 |
| 20 | | 16.4 ± 0.2 | 20.8 ± 0.7 | 22.7 ± 1.1 | 18.3 ± 0.7 |
| 21 | | 18.3 ± 0.4 | 21.5 ± 0.6 | 23.3 ± 1.3 | 19.1 ± 0.5 |

The data presented in Table 4 shows the combination therapy is tolerable in animals, especially at dosage levels which showed clear in vivo efficacy.

Example 4, Tests of Tumor Volume Reduction and Body Weight Changes in Mice During Combination Therapy in a PDX Model with Patient NYL-GZ-082

Figure 5:
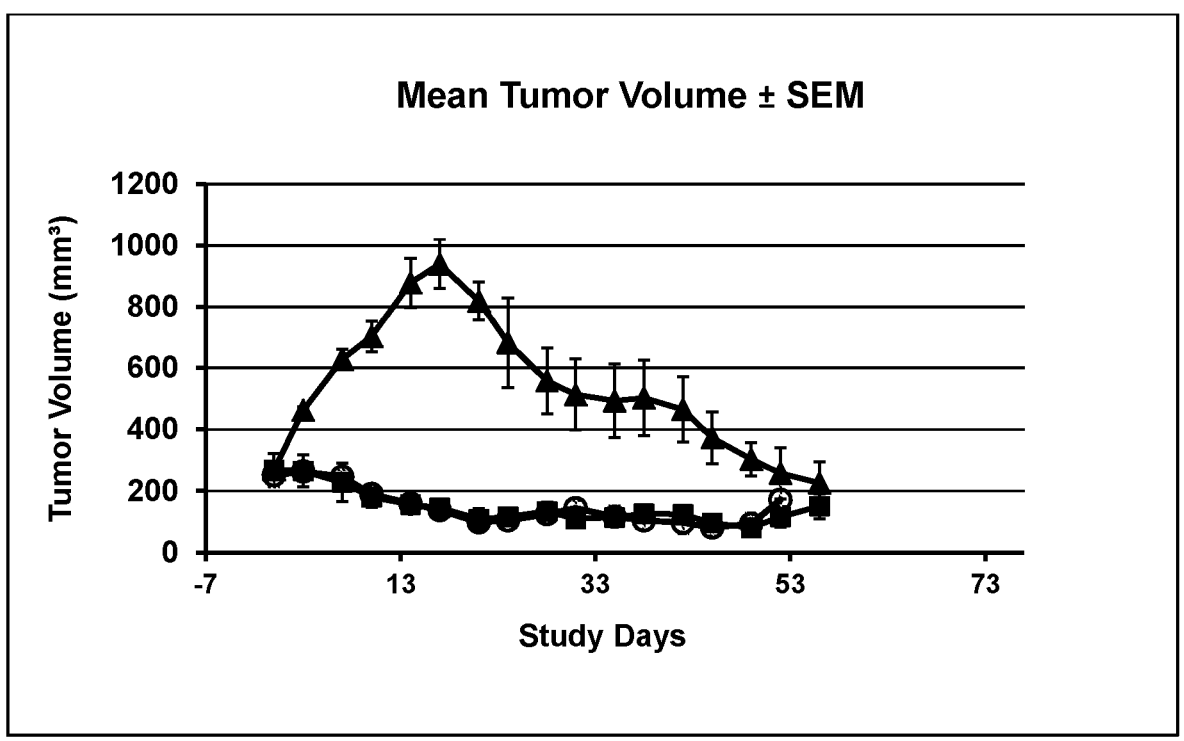
FIG. 5 depicts CRC (NYL-GZ-082) volume reduction upon treatment with combination therapy. The graph shows the mean tumor volume change over time during the combination treatment: (solid triangle)—control with no treatment for 14 days, cetuximab 1 mg per week (i.p.), cobimetinib 5 mg/kg and palbociclib 20 mg/kg daily (p.o.) for 21 days followed by no treatment for 1 week; starting second cycle from day 43 (for the same treatment as the first cycle (first 4 weeks)); (solid square)—osimertinib 10 mg/kg, cobimetinib 5 mg/kg, and palbociclib 2.0 mg/kg daily (p.o.) for 3 weeks followed by no treatment for 1 week; days 28-56 second cycle for the same treatment as the first cycle (first 4 weeks); (open circle)—cetuximab mg per week (i.p.), cobimetinib 5 mg/kg and palbociclib 20 mg/kg daily (p.o.) for 21 days followed by no treatment for 1 week; from days 28-56 starting second cycle for the same treatment as the first cycle (first 4 weeks). The dosage unit, mg/kg, refers to dose of the compound per kg of the mouse body weight.
Figure 6:
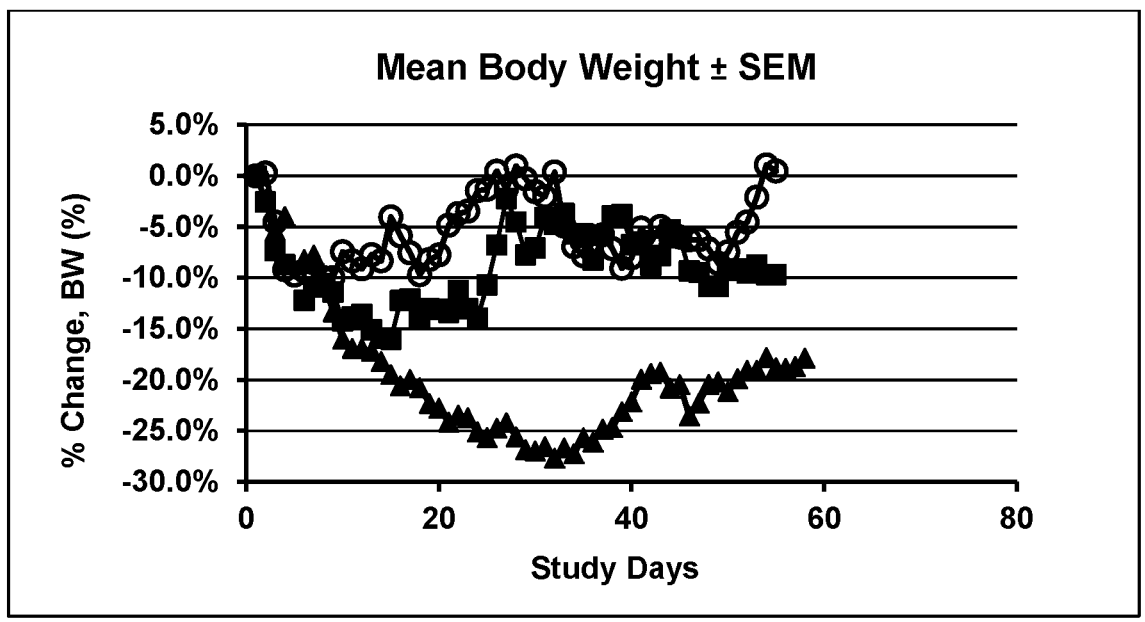
FIG. 6, depicts body weight changes (%) of the mice (NYL-GZ-082) during combination therapy: (solid triangle)—control with no treatment for 14 days, cetuximab 1 mg per week (i.p.), cobimetinib 5 mg/kg and palbociclib 20 mg/kg daily (p.o.) for 21 days followed by no treatment for 1 week; starting second cycle from day 43 (for the same treatment as the first cycle (first 4 weeks)); (solid square)—osimertinib 10 mg/kg, cobimetinib 5 mg/kg, and palbociclib 20 mg/kg daily (p.o.) for 3 weeks followed by no treatment for 1 week; from days 28-56 second cycle for the same treatment as the first cycle (first 4 weeks); (open circle)—cetuximab 1 mg per week (i.p.), cobimetinib 5 mg/kg and palbociclib 20 mg/kg daily (p.o.) for 21 days followed by no treatment for 1 week; days 28-56 second cycle for the same treatment as the first cycle (first 4 weeks).

The same procedures were followed as in Examples 2 and 3 with BRAF$^{V600E}$-CRC patient NYL-GZ-082 using various combinations, Tumor volume values and body weight changes are shown in FIGS. 5 and 6. Both combination therapies: osimertinib cobimetinib palbociclib and cetuximab+cobimetinib+palbociclib reduced tumor volumes. Furthermore, in the control group (FIG. 5, triangle), after 14 days without treatment, the tumor volume increased to >900 mm$^3$. Beginning on Day 15, combination therapy (cetuximab+cobimetinib+palbociclib) was administered and the tumor volume rapidly decreased even after the tumor had grown to a large size. Furthermore, throughout 2 treatment cycles, the tumor regression was maintained.

Example 5. Comparison of Maximum Inhibition Index (MI) and Tumor Growth Inhibition (TGI) for BRAF$^{V600E}$-CRC Treated with Solo and Combination Therapies in a PDX Model with Patient NYL132

The same procedure was followed as in Example 2 with BRAF$^{V600E}$-CRC patient NYL132. The MI (Maximum Inhibition Index) was calculated using the EpCAM and Edu positive readout (Table 6). MI=Edu positive cells in control/Edu positive cells in treatment. And Tumor growth inhibition (TGI) is calculated according to the formula: TGI=(1−(Ti−T0)/(Vi−V0))*100%, where Ti is the mean tumor volume of the treatment group on the measurement day; T0 is the mean tumor volume of the treatment group at D0; Vi is the mean tumor volume of control group at the measurement day; V0 is the tumor volume of the control group at D0.

TABLE 6

MI and TGI Values for BRAF$^{V600E}$-CRCs Treated with Solo and Combination Therapies in a PDX Model with Patient NYL132

| Samples | Concentration (uM) | MI | % TGI |
|---|---|---|---|
| osmertinib | 0.5 | 1.05 | 4.7639% |
| osmertinib | 0.25 | 1.05 | 5.2029% |
| cobimetinib | 0.4 | 26.50 | 96.2260% |
| cobimetinib | 0.2 | 4.99 | 79.9408% |
| palbociclib | 0.15 | 1.65 | 39.3239% |
| palbociclib | 0.075 | 1.42 | 29.7212% |
| osmertinib + cobimetinib | 0.5 + 0.4 | 160.78 | 99.3780% |
| osmertinib + cobimetinib | 0.25 + 0.2 | 252.79 | 99.6044% |
| osmertinib + palbociclib | 0.5 + 0.15 | 2.09 | 52.2064% |
| osmertinib + palbociclib | 0.25 + 0.075 | 1.73 | 42.0732% |
| cobimetinib + palbociclib | 0.4 + 0.15 | 52.48 | 98.0944% |
| cobimetinib + palbociclib | 0.2 + 0.075 | 11.88 | 91.5825% |
| osmertinib + cobimetinib + palbociclib | 0.5 + 0.2 + 1 | 5588.20 | 99.9821% |
| osmertinib + cobimetinib + palbociclib | 0.5 + 0.2 + 1 | 3748.89 | 99.9733% |
| osmertinib + cobimetinib + palbociclib | 0.5 + 0.4 + 0.15 | 15107 | 99.9932% |
| osmertinib + cobimetinib + palbociclib | 0.5 + 0.4*2/3 + 0.15 | 4382.90 | 99.9772% |
| osmertinib + cobimetinib + palbociclib | 0.5 + 0.4*1/3 + 0.15 | 764.85 | 99.8693% |
| osmertinib + cobimetinib + palbociclib | 0.5 + 0.4 + 0.15*4/5 | 4768.59 | 99.9790% |
| osmertinib + cobimetinib + palbociclib | 0.5 + 0.4 + 0.15*3/5 | 13246.10 | 99.9925% |
| pyrotinib | 0.15 | 1.04 | 3.5672% |
| pyrotinib | 0.075 | 1.16 | 13.9749% |
| dabrafenib + trametinib | 0.5 + 0.025 | 3.38 | 70.3800% |
| dabrafenib + trametinib | 0.25 + 0.0125 | 1.34 | 25.1084% |
| dabrafenib + palbociclib | 0.5 + 0.15 | 2.71 | 63.0789% |
| dabrafenib + palbociclib | 0.25 + 0.075 | 1.49 | 32.7757% |
| osmertinib + dabrafenib + trametinib | 0.5 + 0.5 + 0.025 | 134.56 | 99.2569% |
| osmertinib + dabrafenib + trametinib | 0.75 + 0.25 + 0.0125 | 7.84 | 87.2417% |
| dabrafenib | 0.5 | 1.41 | 29.1247% |
| dabrafenib | 0.25 | 1.16 | 13.8183% |
| lynparza | 10 | 1.00 | 0% |
| lynparza | 5 | 1.08 | 7.6251% |
| crizotinib | 0.25 | 1.22 | 17.9798% |
| crizotinib | 0.125 | 1.08 | 7.1772% |

Figure 7:
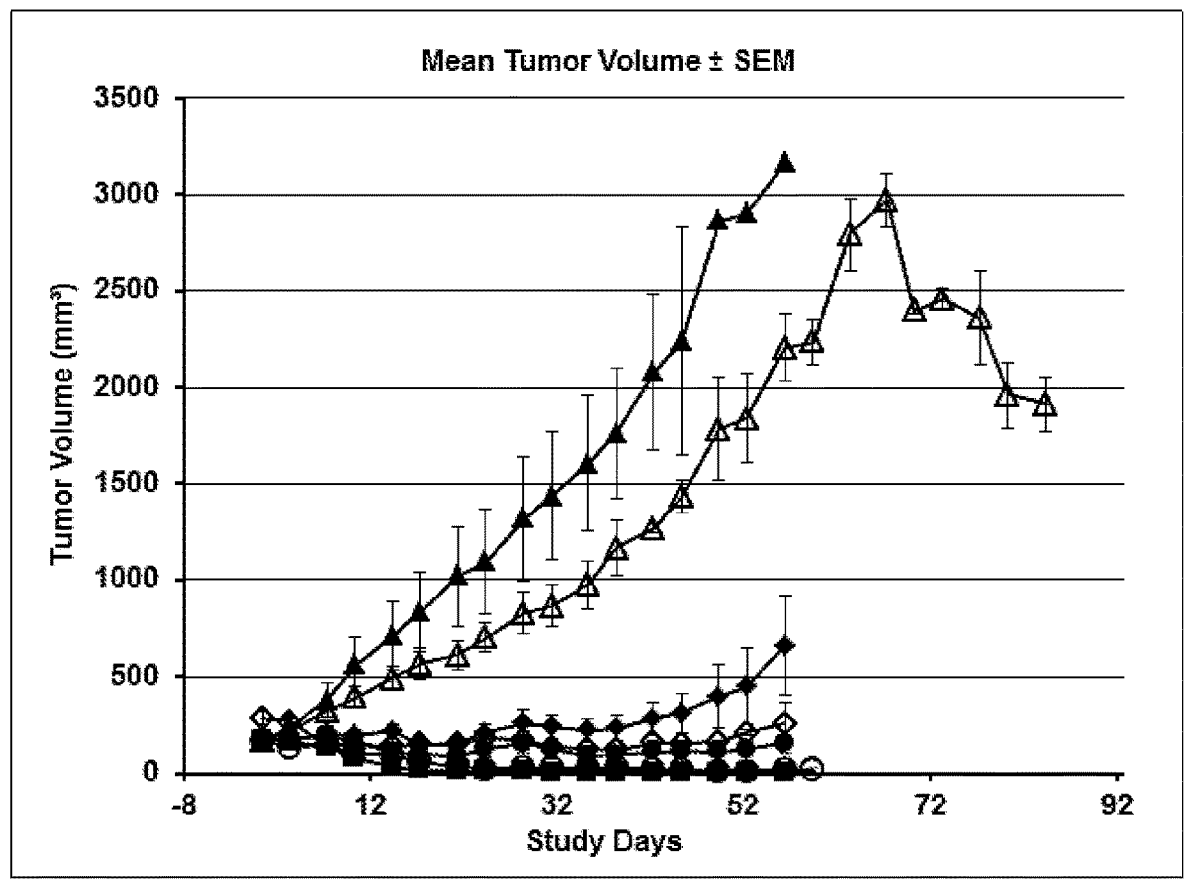
FIG. 7. depicts CRC (NYL132) volume reduction upon treatment with combination therapy. The graph shows the mean tumor volume change over time during the combination treatment: (solid triangle)—control with no treatment; (solid square)—cetuximab 1 mg per week (i.p.), cobimetinib 5 mg/kg and palbociclib 20 mg/kg daily (p.o.) for 21 days, no treatment for 7 days followed by the second cycle for the same treatment as the first cycle (first 4 weeks); (solid circle)—osimertinib 10 mg/kg, TAK-733 3 mg/kg, and palbociclib 20 mg/kg daily (p.o.) for 21 days, no treatment for 7 days followed by the second cycle for the same treatment as the first cycle; (solid diamond)—cetuximab 1 mg per week (i.p.), TAK-733 3 mg/kg and palbociclib 20 mg/kg daily (p.o.) for 21 days, no treatment for 7 days followed by the second cycle for the same treatment as the first cycle; (open triangle)—cetuximab 1 mg per week (i.p.) for 21 days, no treatment for 7 days, cetuximab 1 mg per week (i.p.) from days 28-49, no treatment for another 7 days followed by cetuximab 1 mg per week (i.p.), cobimetinib 5 mg/kg and palbociclib 20 mg/kg daily (p.o.) for another 21 days; (open circle)—cetuximab 1 mg per week (i.p.), TAK-733 10 mg/kg and palbociclib 20 mg/kg daily (p.o.) for 21 days, no treatment for 7 days followed by the second cycle for the same treatment as the first cycle; (open diamond)—osimertinib 10 mg/kg, TAK-733 10 mg/kg, and palbociclib 20 mg/kg daily (p.o.) for 21 days, no treatment for 7 days followed by the second cycle for the same treatment as the first cycle.

FIG. 7 shows the tumor volume changes during the treatment of various solo and combination therapies in a PDX model with patient NYL132. All three combinations tested (1) cetuximab+cobimetinib+palbociclib, (2) osimertinib TAK-733+palbociclib and (3) cetuximab+TAK-733 palbociclib, reduced tumor volumes for >85% in the first treatment cycle (21 days) (see also Table 7). The singlet cetuximab treatment only slightly inhibited the tumor growth (open triangle, 2-cycle treatment from start to Day 56) and singlet cetuximab treated tumor was sensitive to the treatment of the combination of cetuximab 1 mg per week (i.p.), cobimetinib 5 mg/kg and palbociclib 20 mg/kg daily (p.o.) for 2.1 days.

TABLE 7

Tumor Growth Inhibition of a PDX Model Derived
From BRAF$^{V600E}$-CRC Patient NYL132

| Treatment combination | Day | Average tumor growth inhibition % (3 animals) |
|---|---|---|
| 1$^{st}$ cycle of treatment: cetuximab, 1 mg/kg, once weekly, i.p., palbociclib, 20 mg/kg, QD, p.o., cobimetinib, 5 mg/kg, QD, p.o. for 3 weeks, followed by 1 week off treatment. Continue to the 2$^{nd}$ cycle for the treatment as the 1$^{st}$ cycle. | 42 | 99.86% |
| 1$^{st}$ cycle of treatment: osimertinib, 10 mg/kg, QD, p.o., palbociclib, 20 mg/kg, QD, p.o., TAK-733, 3 mg/kg, QD, p.o, for 3 weeks, followed by 1 week of no treatment Continue to the 2$^{nd}$ cycle for the treatment as the 1$^{st}$ cycle. | 42 | 94.58% |
| 1$^{st}$ cycle of treatment: cetuximab, 1 mg/kg, once weekly, i.p., palbociclib, 20 mg/kg, QD, p.o., TAK-733, 3 mg/kg, QD, p.o. for 3 weeks, followed by 1 week off treatment. Continue to the 2$^{nd}$ cycle for the treatment as the 1$^{st}$ cycle. | 42 | 86.29% |
| 1$^{st}$ cycle of treatment: cetuximab, 1 mg/kg, once weekly for 3 weeks, followed by 1 week off treatment. Continue to the 2$^{nd}$ cycle for the treatment as the 1$^{st}$ cycle. | 42 | 39.08% |
| 1$^{st}$ cycle of treatment: osimertinib, 10 mg/kg, QD, p.o., palbociclib, 20 mg/kg, QD, p.o., TAK-733, 10 mg/kg, QD, p.o, for 3 weeks, followed by 1 week of no treatment Continue to the 2$^{nd}$ cycle for the treatment as the 1$^{st}$ cycle. | 42 | 92.36% |
| 1$^{st}$ cycle of treatment: cetuximab, 1 mg/kg, once weekly, i.p., palbociclib, 20 mg/kg, QD, p.o., TAK-733, 10 mg/kg, QD, p.o. for 3 weeks, followed by 1 week off treatment. Continue to the 2$^{nd}$ cycle for the treatment as the 1$^{st}$ cycle. | 42 | 98.85% |

Example 6. Comparison of Maximum Inhibition Index (MI) and Tumor Growth Inhibition (TGI) for BRAF$^{V600E}$-CRC Treated with Solo and Combination Therapies in a CDX Model with Cell Line HT-29

A cell line HT-29 derived xenograft (CDX) in vivo efficacy study was conducted. The experimental procedures are briefly outlined as follows. Sufficient donor cells (HT-29) were cultured and prepared for inoculation. A minimum of 3×10$^6$ cells suspended in Matrigel were injected dorsal side of female nude mice. When the tumor volume of the mice grew to 100-300 mm$^3$, the mice with irregular tumor shape and poor condition were excluded according to the weight and tumor growth of the mice, and the remaining mice were randomly divided into groups, typically 3-5 mice per group. The day of randomization was defined as study day 0. Tumor volume is expressed in mm$^3$ using the following formula: V (volume)=(a×b$^2$)/2 where a and b are the long and short diameters of the tumor, respectively. Tumor suppression was expressed as Tumor growth inhibition (TGI), which is calculated according to the formula: TGI=(1−(Ti−T0)/(Vi−V0))*100%, where Ti is the mean tumor volume of the treatment group on the measurement day; T0 is the mean tumor volume of the treatment group at D0; Vi is the mean tumor volume of control group at the measurement day; V0 is the tumor volume of the control group at D0.

The MI (Maximum Inhibition Index) was calculated using the EpCAM and Edu positive readout (Table 8). MI=Edu positive cells in control/Edu positive cells in treatment. And Tumor growth inhibition (TGI) is calculated according to the formula: TGI=(1−(Ti−T0)/(Vi−V0))*100%, where Ti is the mean tumor volume of the treatment group on the measurement day; T0 is the mean tumor volume of the treatment group at D0; Vi is the mean tumor volume of control group at the measurement day; V0 is the tumor volume of the control group at D0.

TABLE 8

MI and TGI Values for BRAF$^{V600E}$-CRCs Treated with Solo and Combination Therapies in a CDX Model with Cell Line HT-29

| Samples | Concentration (uM) | MI | % TGI |
|---|---|---|---|
| osmertinib | 0.5 | 1.20 | 16.9639% |
| afatinib | 0.2 | 1.24 | 19.2409% |
| cobimetinib | 0.4 | 331.41 | 99.6983% |
| trametinib | 0.02 | 17.16 | 94.1714% |
| palbociclib | 0.15 | 4.64 | 78.4714% |
| ribociclib | 5 | 11.24 | 91.1053% |
| osmertinib + cobimetinib + palbociclib | 0.5 + 0.4 + 0.15 | 23332.49 | 99.9957% |
| osmertinib + cobimetinib + ribociclib | 0.5 + 0.4 + 5 | 12790.35 | 99.9922% |
| osmertinib + trametinib + palbociclib | 0.5 + 0.02 + 0.15 | 24849.10 | 99.9960% |
| osmertinib + trametinib + ribociclib | 0.5 + 0.02 + 5 | 24849.10 | 99.9960% |
| afatinib + cobimetinib + palbociclib | 0.2 + 0.4 + 0.15 | 24849.10 | 99.9960% |
| afatinib + cobimetinib + ribociclib | 0.2 + 0.4 + 5 | 24849.10 | 99.9960% |
| afatinib + trametinib + palbociclib | 0.2 + 0.02 + 0.15 | 6598.97 | 99.9848% |
| afatinib + trametinib + ribociclib | 0.2 + 0.02 + 5 | 24849.10 | 99.9960% |

Figure 8:
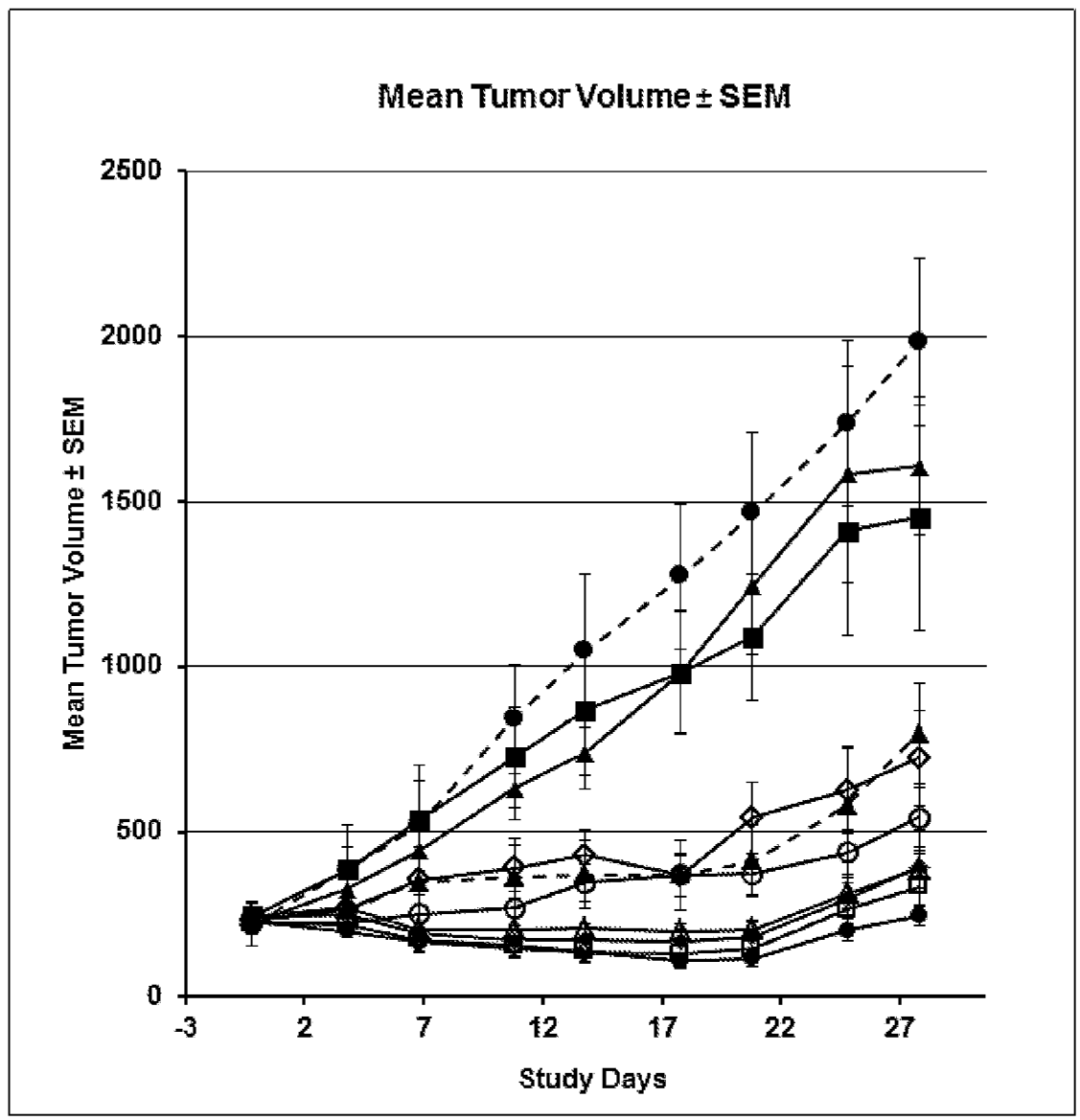
FIG. 8. depicts CRC (HT-29) volume reduction upon treatment with combination therapy. The graph shows the mean tumor volume change over time during the combination treatment: (solid triangle)—control with no treatment for 28 days; (solid square) capecitabine 200 mg/kg daily (p.o.) for 21 days; (solid circle)—cetuximab 1 mg per week (i.p.), cobimetinib 5 mg/kg and palbociclib 20 mg/kg daily (p.o.) for 21 days; (solid diamond)—cetuximab 1 mg per week (i.p.), cobimetinib 5 mg/kg and palbociclib 13.3 mg/kg daily (p.o.) for 21 days; (open triangle)—cetuximab 1 mg per week (i.p.), cobimetinib 5 mg/kg and palbociclib 6.6 mg/kg daily (p.o.) for 21 days; (open square)—osimertinib 10 mg/kg, cobimetinib 5 mg/kg, and palbociclib 20 mg/kg daily (p.o.) for 21 days; (open circle)—osimertinib 10 mg/kg and cobimetinib 5 mg/kg daily (p.o.) for 21 days; (open diamond)—cobimetinib 5 mg/kg daily (p.o.) for 21 days; (dash line solid triangle)—cobimetinib 5 mg/kg, and palbociclib 20 mg/kg daily (p.o.) for 21 days; (dash line solid circle)—5-FU 40 mg/kg per week for 3 weeks. On Day 21, all treatments stopped followed by 1 week of observation.
Figure 9:
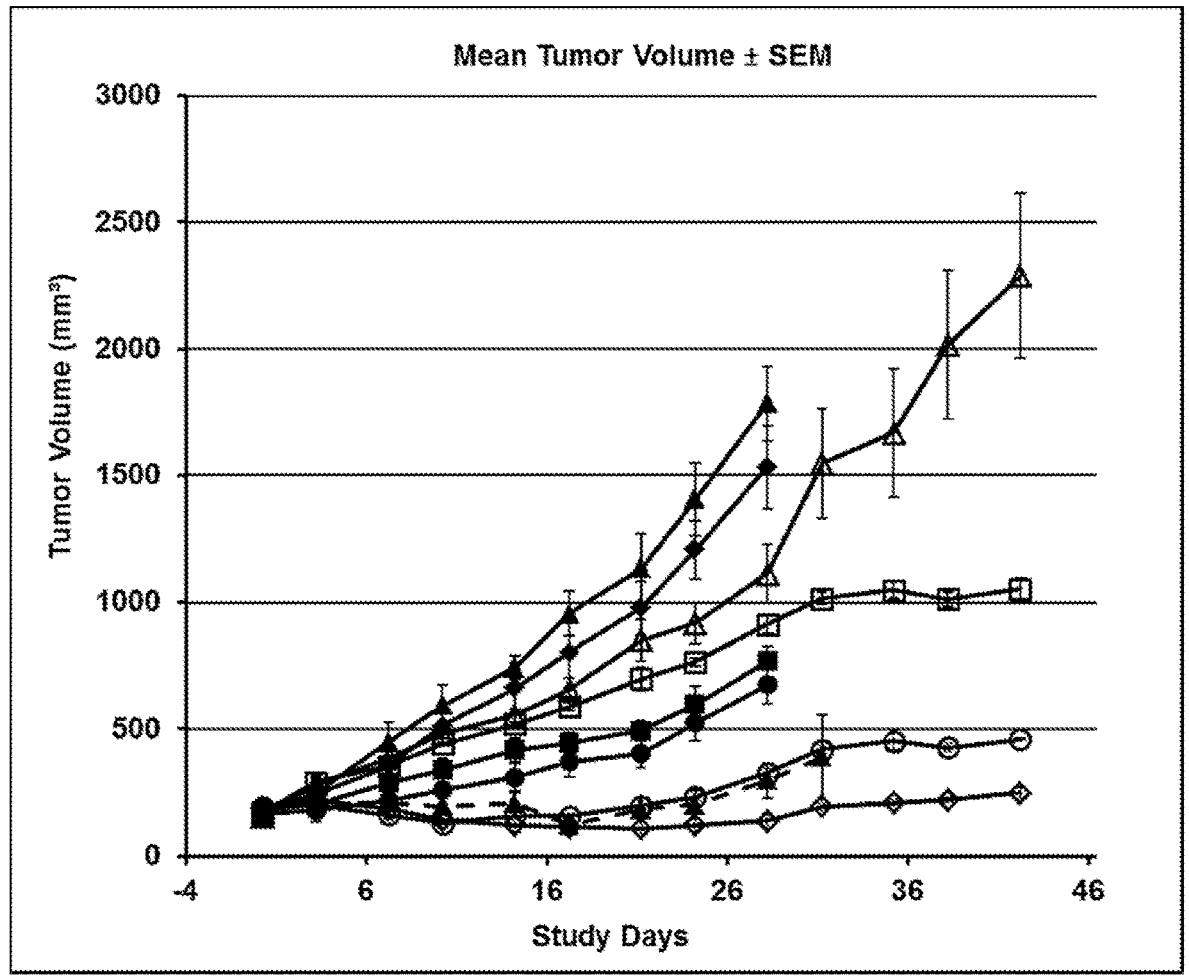
FIG. 9. depicts CRC (HT-29) volume reduction upon treatment with combination therapy. The graph shows the mean tumor volume change over time during the combination treatment: (solid triangle)—control with no treatment for 21 days; (solid square)—TAK-733 10 mg/kg daily (p.o.) for 21 days; (solid circle)—TAK-733 30 mg/kg for day 1, then 3 mg/kg for daily (p.o.) for 20 days; (solid diamond)—palbociclib 20 mg/kg daily (p.o.) for 21 days; (open triangle) cetuximab 1 mg per week (i.p.) for 21 days, then 7 days off treatment, followed by 1 mg per week (i.p) for another 14 days; (open square)—capecitabine 200 mg/kg daily (p.o.) and oxaliplatin 10 mg/kg per week (i.p.) for 21 days, then 7 days off treatment; after day 28, cetuximab 1 mg per week (i.p.), cobimetinib 5 mg/kg and palbociclib 20 mg/kg daily (p.o.) for 14 days; (open circle) osimertinib 10 mg/kg, TAK-733 10 mg/kg, and palbociclib 20 mg/kg daily (p.o.) for 2.1 days, then 7 days off treatment, followed by the same dosages for 14 days; (open diamond)—cetuximab 1 mg per week (i.p.), TAK-733 10 mg/kg and palbociclib 20 mg/kg daily (p.o.) for 21 days, then 7 days off treatment, followed by the same dosages for 14 days; (dash line solid triangle)—TAK-733 10 mg/kg and palbociclib 20 mg/kg daily (p.o.) for 21 days.

FIGS. 8 and 9 show the tumor volume changes during the treatment of various singlet agent, and doublet and triplet combination therapies in a CDX model with cell line HT-29. All four combinations tested (1) osimertinib+cobimetinib+palbociclib, (2) cetuximab+cobimetinib+palbociclib, (3) osimertinib+TAK-733+palbociclib, and (4) cetuximab+TAK-733+palbociclib reduced tumor volumes for >50% in the first treatment cycle (21 days). The chemotherapeutic agents of capecitabine (square) and 5-FU (dash circle) showed no efficacy and the tumor growth trend was similar to that of the vehicle control (triangle). The triplet combination of cetuximab, cobimetinib and palbociclib, as well as the triplet combination of osimertinib, cobimetinib and palbociclib, showed superior tumor growth inhibition than the singlet treatment (cobimetinib), and the doublet combinations of cobimetinib and osimertinib, as well as cobimetinib and palbociclib (see also Table 9).

TABLE 9

Tumor Growth Inhibition of a CDX model with cell line HT-29

| Treatment combination | Day | Combination | Average tumor growth inhibition % |
|---|---|---|---|
| control with no treatment for 28 days | 28 | | |
| capecitabine 200 mg/kg daily (p.o.) for 21 days | 28 | capecitabine | 12.7% |
| cobimetinib 5 mg/kg daily (p.o.) for 21 days | 28 | cobimetinib | 64.4% |
| osimertinib 10 mg/kg and cobimetinib 5 mg/kg daily (p.o.) for 21 days | 28 | osimertinib + cobimetinib | 76.8% |
| cobimetinib 5 mg/kg, and palbociclib 20 mg/kg daily (p.o.) for 21 days | 28 | cobimetinib + palbociclib | 60.5% |
| cetuximab 1 mg per week (i.p.), cobimetinib 5 mg/kg and palbociclib 20 mg/kg daily (p.o.) for 21 days | 78 | cetuximab + cobimetinib + palbociclib | 98.9% |
| cetuximab 1 mg per week (i.p.), cobimetinib 5 mg/kg and palbociclib 13.3 mg/kg daily (p.o.) for 21 days | 28 | cetuximab + cobimetinib + palbociclib | 88.8% |
| cetuximab 1 mg per week (i.p.), cobimetinib 5 mg/kg and palbociclib 6.6 mg/kg daily (p.o.) for 21 days | 28 | cetuximab + cobimetinib + palbociclib | 89.8% |
| osimertinib 10 mg/kg, cobimetinib 5 mg/kg, and palbociclib 20 mg/kg daily (p.o.) for 21 days | 28 | osimertinib + cobimetinib + palbociclib | 91.9% |

Example 7. Clinical Study of Combination Therapies

A Phase 2, open label clinical study in patients having advanced colorectal cancers with either a BRAF$^{V600E}$ mutation is conducted. The study is designed to evaluate the safety and efficacy of the combination therapy (cetuximab+cobimetinib+palbociclib) in patients with advanced colorectal cancers. The study subject population includes adult males and females 18-75 years old having a diagnosis of advanced colorectal cancers with either a BRAF$^{V600E}$ mutation and having an expected survival period of longer than 12 months.

Subjects are given (1) cetuximab in 400 mg/m$^2$ infused for 120 minutes with a maximum infusion rate of 10 mg/min for 1 week, followed by 250 mg/m$^2$ once weekly; (2) cobimetinib 20-60 mg orally per day; and (3) palcociclib 75-125 mg orally per day. Vital signs, clinical laboratory measurements, resting ECG measurements, adverse events and serious adverse events are monitored and assessed. Overall Response Rate, Disease Control Rate, overall survival, duration of response and quality of life are also monitored and assessed. The study parameters are summarized in Table 10.

TABLE 10

| | |
|---|---|
| Study Title | A single-center, open label study to evaluate he safety and efficacy of the combination therapy with cetuximab, cobimetinib and palcociclib in patients having advanced colorectal cancers with either a BRAF$^{V600E}$ mutation. |
| Development Phase | Phase 1b/2 |
| Study Objectives | Primary Objective:<br>To evaluate the safety and efficacy of the combination therapy with cetuximab, cobimetinib and palcociclib in patients having advanced colorectal cancers with either a BRAF$^{V600E}$ mutation.<br>Secondary Objectives:<br>To evaluate patients' survival rates<br>To evaluate patients' quality of life |
| Study Population | This study is conducted in adult males and females, aged 18-75 years with having advanced colorectal cancers with either a BRAF$^{V600E}$ mutation and having gone through an unsuccessful treatment with other methods. The subjects have an expected survival period of longer than 12 months. The subjects have not received any treatment involving EGFR inhibitors.<br>Cohort 1: patients with the BRAF$^{V600E}$ mutation |
| Investigational Product | Combination of cetuximab, cobimetinib and palcociclib |
| Dosage and Frequency | Cetuximab: 400 mg/m$^2$, intravenous infusion, every two weeks; loading infusion time of 120 minutes, followed by maintenance 250 mg/m$^2$ with infusion time of 60 mins, maximum infusion rate of 10 mg/min;<br>Cobimetinib: 40 mg orally per day for 21 days (28 days per cycle); if tolerated well by patient, dosage increases to 60 mg orally per day for the next cycle (28 days); if not tolerated well by patient after one cycle, dosage decreases to 20 mg orally per day for the next cycle (28 days);<br>Palbociclib: 100 mg orally per day for 21 days (28 days per cycle); if tolerated well by patient, dosage increases to 125 mg orally per day for the next cycle (28 days); if not tolerated well by patient after one cycle, dosage decreases to 75 mg orally per day for the next cycle (28 days).eb; normal |

TABLE 10-continued

| | |
|---|---|
| Efficacy Evaluation Criteria | Efficacy is assessed by Overall Response Rate, Disease Control Rate, overall survival, duration of response and quality of life. |
| Safety Evaluation Criteria | Safety is assessed by vital signs, clinical laboratory measurements, resting ECG measurements, adverse events and adverse events, |

What is claimed is:

1. A method of treating or delaying progression of cancer in a subject comprising administering to the subject an affective amount of
    (a) an epidermal growth factor receptor (EGFR) inhibitor;
    (b) a mitogen-activated protein kinase (MEK) 1/2 inhibitor; and
    (c) a cyclin dependent kinase (CDK) 4/6 inhibitor;
    wherein the EGFR inhibitor is cetuximab, the MEK 1/2 inhibitor is cobimetinib or a salt thereof and the CDK 4/6 inhibitor is palbociclib or a salt thereof; wherein the subject has cancer or is at risk of developing cancer that has a BRAF mutation; and wherein a BRAF inhibitor is not administered to the subject.

2. The method of claim 1, wherein the cancer has a BRAF V600 mutation or a BRAF D581V mutation.

3. The method of claim 2, wherein the BRAF V600 mutation is V600E, V600D, or V600K.

4. The method of claim 1, wherein the cancer is a malignant epithelial tumor or carcinoma.

5. The method of claim 4, wherein the carcinoma is selected from one or more of an adenocarcinoma, a squamous cell carcinoma, an adenosquamous carcinoma, an anaplastic carcinoma, a large cell carcinoma, a small cell carcinoma, an epithelial neoplasm, a squamous cell neoplasm, a basal cell neoplasm, a transitional cell carcinoma, an adenocarcinoma, an adnexal or skin appendage neoplasm, a mucoepidermoid neoplasm, a cystic, mucinous, or Serous neoplasm, a ductal, lobular, or medullary neoplasm, an acinar cell neoplasm, and a complex epithelial neoplasm.

6. The method of claim 1, wherein the cancer is a carcinoma selected from one or more of a colon cancer, a gastric cancer, a lung cancer, a breast cancer, a pancreatic cancer, an oral cancer, a prostate cancer, a germline cancer, a rectal cancer, a liver cancer, a kidney cancer, a papillary thyroid cancer, and an ovarian cancer.

7. The method of claim 1, wherein the cancer is a colorectal cancer.

8. The method of claim 7, wherein the cancer is stage IV colorectal cancer.

9. The method of claim 8, wherein the colorectal cancer has a BRAF V600E or D581V mutation.

10. The method of claim 1, wherein the method reduces mean tumor volume by about 20-95%.

11. The method of claim 1, wherein cobimetinib or a salt thereof is administered to the subject in a daily dose of about 0.25-1 mg/kg.

12. The method of claim 1, wherein palbociclib or a salt thereof is administered to the subject in a daily dose of about 1-2.5 mg/kg.

13. The method of claim 1, wherein cetuximab, cobimetinib or a salt thereof, and palbociclib or a salt thereof are administered in one composition.

14. The method of claim 1, wherein cetuximab, cobimetinib or a salt thereof, and palbociclib or a salt thereof are administered simultaneously to the subject.

15. The method of claim 1, wherein cetuximab, cobimetinib or a salt thereof, and palbociclib or a salt thereof are administered intermittently to the subject.

16. The method of claim 1, wherein cetuximab is administered to the subject in a weekly dose of about 400 mg/m$^2$ infused over 120 minutes followed by weekly dose of 250 mg/m$^2$ infused over 60 minutes.

17. The method of claim 1, wherein cetuximab is administered to the subject in a weekly dose of about 400 mg/m$^2$ infused over 120 minutes with a maximum infusion rate of 10 mg/min, followed by weekly dose of 250 mg/m$^2$ infused over 60 minutes with a maximum infusion rate of 10 mg/min.

18. The method of claim 1, wherein the method reduces cancer cell growth and/or increase cancer cell-killing by about 20-99% more than administration of cetuximab, cobimetinib or a salt thereof, or palbociclib or a salt thereof alone.

19. The method of claim 1, wherein cobimetinib or a salt thereof and palbociclib or a salt thereof are orally administered to the subject.

20. The method of claim 2, wherein the cancer is a colorectal cancer, and wherein the BRAF V600 mutation is V600E, V600D, or V600K.

21. The method of claim 1, wherein cobimetinib or a salt thereof is administered to the subject in a daily dose of about 20-60 mg.

22. The method of claim 1, wherein palbociclib or a salt thereof is administered to the subject in a daily dose of about 75-125 mg.

23. The method of claim 1, wherein the subject is a human.

* * * * *